(12) United States Patent
Carlson et al.

(10) Patent No.: US 6,939,515 B2
(45) Date of Patent: Sep. 6, 2005

(54) APPARATUSES AND METHODS FOR CREATING AND TESTING PRE-FORMULATIONS AND SYSTEMS FOR SAME

(75) Inventors: Eric D. Carlson, Cupertino, CA (US); Peijun Cong, San Jose, CA (US); William H. Chandler, Jr., Milpitas, CA (US); Peter J. Desrosiers, Santa Clara, CA (US); J. Christopher Freitag, Santa Clara, CA (US); John F. Varni, Los Gatos, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/156,245

(22) Filed: May 24, 2002

(65) Prior Publication Data

US 2003/0116497 A1 Jun. 26, 2003

Related U.S. Application Data

(60) Provisional application No. 60/311,332, filed on Aug. 10, 2001.

(51) Int. Cl.$^7$ ............................................... B01L 11/00
(52) U.S. Cl. .................... 422/101; 422/102; 210/321.6; 210/321.75; 435/305.2; 435/305.3; 435/305.4
(58) Field of Search ............................. 210/323.1, 455, 210/649, 650, 767, 295, 321.6, 321.64, 321.72, 321.75, 321.84; 422/101, 102

(56) References Cited

U.S. PATENT DOCUMENTS

| | | | |
|---|---|---|---|
| 3,673,290 A | 6/1972 | Brubaker et al. | 264/43 |
| 4,185,468 A | 1/1980 | Adams, Jr. | 63/123 |
| 4,263,010 A | 4/1981 | Randolph | 23/230 A |
| 4,390,722 A | 6/1983 | Lahav et al. | 562/402 |
| 4,399,687 A | 8/1983 | Collins | 73/23 |

(Continued)

FOREIGN PATENT DOCUMENTS

| | | | |
|---|---|---|---|
| EP | 0 882 500 | 12/1998 | B01J/19/00 |
| WO | WO 96/11878 | 4/1996 | C01G/51/04 |
| WO | WO 97/10221 | 3/1997 | C07D/239/88 |

(Continued)

OTHER PUBLICATIONS

Gerald Gold and James A. Campbell, "Effects of selected U.S.P. talcs and acetylsalicylic acid stability in tablets," Journal of Pharmaceutical Sciences, vol. 53, No. 1, pp. 52–54, Jan. 1964.

(Continued)

*Primary Examiner*—W. L. Walker
*Assistant Examiner*—Krishanan S Memon

(57) ABSTRACT

The invention provides methods, apparatus, and systems for performing high-throughput preparation and screening of salts and polymorphs of drug candidates. The invention is directed towards enhancing the pre-formulation discovery process used for drug development. In particular, processes that determine suitable salts and processes that discover substantially every polymorph that can form from a particular drug candidate are provided. The processes are performed using several apparatuses that are specifically configured to carry-out various steps in a high-throughput characterization process. One such apparatus is configured for synthesizing a plurality of library members based on, for example, a library model generated by a computer system. Another apparatus may filter the synthesized solution to provide a substantially pure mixture that can be subjected to salt or polymorph testing. Yet another apparatus may be used to crystallize mixtures on a substrate such that the crystallized mixture can be screened by one or more screening devices.

16 Claims, 41 Drawing Sheets

U.S. PATENT DOCUMENTS

| | | | |
|---|---|---|---|
| 4,489,133 A | 12/1984 | Kornberg | 428/408 |
| 4,755,363 A | 7/1988 | Fujita et al. | 422/245 |
| 4,859,538 A | 8/1989 | Ribi | 428/474.4 |
| 4,990,216 A | 2/1991 | Fujita et al. | 156/600 |
| 5,087,952 A | 2/1992 | Ribi | 357/25 |
| 5,118,840 A | 6/1992 | Kano et al. | 562/443 |
| 5,141,718 A * | 8/1992 | Clark | 422/99 |
| 5,256,241 A | 10/1993 | Noever | 156/600 |
| 5,324,483 A | 6/1994 | Cody et al. | 422/131 |
| 5,328,549 A | 7/1994 | Bozler et al. | 437/226 |
| 5,365,456 A | 11/1994 | Subbiah | 364/499 |
| 5,430,194 A | 7/1995 | Barner et al. | 568/429 |
| 5,516,490 A | 5/1996 | Sanadi | 422/101 |
| 5,540,891 A | 7/1996 | Portmann et al. | 422/102 |
| 5,641,681 A | 6/1997 | Carter | 436/4 |
| 5,714,127 A | 2/1998 | DeWitt et al. | 422/131 |
| 5,871,781 A | 2/1999 | Myers et al. | 425/9 |
| 5,961,926 A | 10/1999 | Kolb et al. | 422/101 |
| 5,961,934 A | 10/1999 | Arnowitz et al. | 422/245.1 |
| 5,962,250 A * | 10/1999 | Gavin et al. | 435/29 |
| 5,972,694 A * | 10/1999 | Mathus | 435/288.4 |
| 5,985,214 A | 11/1999 | Stylli et al. | 422/65 |
| 6,017,390 A | 1/2000 | Charych et al. | 117/68 |
| 6,027,565 A | 2/2000 | Bugg et al. | 117/202 |
| 6,027,694 A | 2/2000 | Boulton et al. | 422/102 |
| 6,031,082 A | 2/2000 | Nielsson et al. | 530/413 |
| 6,039,804 A | 3/2000 | Kim et al. | 117/206 |
| 6,125,235 A | 9/2000 | Padilla et al. | 395/500.32 |
| 6,129,828 A | 10/2000 | Sheldon, III et al. | 204/518 |
| 6,174,365 B1 | 1/2001 | Sanjoh | 117/68 |
| 6,245,508 B1 | 6/2001 | Heller et al. | 435/6 |
| 6,306,658 B1 * | 10/2001 | Turner et al. | 436/37 |
| 6,507,636 B1 | 1/2003 | Lehmann | 378/79 |
| 6,548,026 B1 * | 4/2003 | Dales et al. | 422/138 |
| 6,759,014 B2 * | 7/2004 | Dales et al. | 422/130 |
| 2002/0192119 A1 * | 12/2002 | DeSilets et al. | 422/101 |

FOREIGN PATENT DOCUMENTS

| | | | | |
|---|---|---|---|---|
| WO | WO 98/52614 | 11/1998 | | A61K/47/48 |
| WO | WO 99/06814 | 2/1999 | | G01N/1/10 |
| WO | WO 99/59716 | 11/1999 | | B01J/19/00 |
| WO | WO 00/23921 | 4/2000 | | G06F/17/50 |
| WO | WO 00/24511 | 5/2000 | | B01L/3/00 |
| WO | WO 00/53282 | 9/2000 | | B01D/9/00 |
| WO | WO 00/59627 | 10/2000 | | B01J/19/00 |
| WO | WO 00/60345 | 10/2000 | | G01N/31/00 |
| WO | WO 00/67086 | 11/2000 | | G05B/19/414 |
| WO | WO 00/78445 A1 | 12/2000 | | B01J/19/00 |
| WO | WO 01/09391 A1 | 2/2001 | | C12Q/3/00 |
| WO | WO 01/36087 A1 | 5/2001 | | B01J/19/00 |
| WO | WO 01/51919 A2 | 7/2001 | | G01N/30/00 |
| WO | WO 01/82659 A1 | 11/2001 | | H05H/15/00 |

OTHER PUBLICATIONS

P. A. Martin et al., "Automation of microtiter plate–chromogenic substrate LAL endotoxin assay method by use of a modified cetus pro/pette express system," Journal of Parenteral Science & Technology, vol. 40, No. 2, pp. 61–66, Mar.–Apr. 1986.

Charles W. Carter, Jr. and Charles W. Carter, "Protein Crystallization Using Incomplete Factorial Experiments," The Journal of Biological Chemistry, vol. 254, No. 23, Dec. 10, 1979, pp. 12219–12223.

Egidijus E. Uzgiris and Roger D. Kornberg, "Two–dimensional crystallization technique for imaging macromolecules, with application to antigen–antibody–complement complexes," Nature, vol. 301, pp. 125–129, Jan. 13, 1983.

R. J. Eckstein et al., "Unattended, Robotic Drug–Release Testing of Enterically Coated Asprin," Analytical Chemistry, vol. 58, pp. 2316–2320, 1986.

Charles W. Carter et al., "Statistical Design of Experiments for Protein Crystal Growth and the Use of Precrystallization Assay," Journal of Crystal Growth, vol. 90, pp. 60–73, 1988.

Andreas Hotzenburg, "Preparation of Two–dimensional arrays of soluble proteins as demonstrated for bacterial D–Ribulose–1,5–bisphosphate carboxylase/oxygenase", Methods in Microbiology, vol. 26, 1988.

R. J. Guttendorf, et al. "Rapid screening for polymorphisms in dextromethorphan and mephenytoin metabolism," British Journal of Clinical Pharmacology, vol. 29, pp. 373–380, Apr. 1990.

M. B. Garber et al., "Purification and crystallization of components of the protein–synthesizing system from *Thermus thermophilus*," Journal of Crystal Growth, vol. 110, pp. 228–236, 1991.

Alexander McPherson, "Two approaches to the rapid screening of crystallization conditions," Journal of Crystal Growth, vol. 122, pp. 161–167, 1992.

Sergio E. Martinez and Janet L. Smith, "Crystallization and Preliminary Characterization of Mitogilin, a Ribosomal Ribonuclease from *Aspergillus restrictus*," Journal of Molecular Biology, vol. 218, pp. 489–492, 1991.

Andreas Paul, et al. "Two–dimensional crystallization of a bacterial surface protein on lipid vesicles under controlled conditions," Biophysical Journal © Biophysical Society, vol. 61, pp. 172–188, Jan. 1992.

Jennifer A. Doudna et al., "Cryatallization of ribozymes and small RNA motifs by a sparse matrix approach," Proc. Natl. Acad. Sci., vol. 90, pp. 7829–7833, Aug. 1993.

Mark A. Gallop et al., "Applications of combinatorial technologies to drug discovery. 1. Background and peptide combinatorial libraries," Journal of Medicinal Chemistry, vol. 37, No. 9, pp. 1233–1251, Apr. 19, 1994.

Eric M. Gordon et al., "Applications of combinatorial technologies to drug discovery. 2. Combinatorial organis synthesis, library screening strategies, and future directions," Journal of Medicinal Chemistry, vol. 37, No. 10, pp. 23–25, May 13, 1994.

"High throughput screening: drug discovery through automation," Pharmaceutical News, vol. 2, No. 3, pp. 23–25, 1995.

Thomas Carell et al., "New promise in combinatorial chemistry: synthesis, characterization, and screening of small–molecule libraries in solution," Chemistry & Biology, vol. 2, No. 3, pp. 171–183, Mar. 1995.

J. Michael Ramsey et al., "Microfabricated chemical measurement systems," Nature Medicine, vol. 1, No. 10, pp. 1093–1096, Oct. 1995.

Peng–Liang Zhao et al., "Sample size determination in combinatorial chemistry," Proc. Natl. Acad. Sci. USA, vol. 92, pp. 10212–10216, Oct. 1995.

M. Akong et al., "High–throughput measurement of intracellular $Ca^{2+}$ by fluorescence imaging of a 96–well microtiter plate," Society For Neuroscience Abstracts, vol. 21, part 1, p. 577, Nov. 13, 1995.

Sheila H. DeWitt and Anthony W. Czarnik, "Automated synthesis and combinatorial chemistry," Current Opinion in Biotechnology, vol. 6, No. 6, pp. 640–645, Dec. 1995.

Janet M. Kolb et al., "Use of a novel homogeneous fluorescent technology in high throughput screening," Journal of Biomolecular Screening, vol. 1, No. 4, pp. 203–210, 1996.

William P. Janzen, "High throughput screening as a discovery tool in the pharmaceutical industry," Laboratory Robotics and Automation, vol. 8, No. 5, pp. 261–265, 1996.

Melvin Reichman et al., "Approaches to automation for high–throughput screening," Laboratory robotics and automation, vol. 8, No. 5, pp. 267–276, 1996.

Kirk S. Schroeder and Brad D. Neagle, "FLIPR: A new instrument for accurate, high throughput optical screening," Journal of Biomolecular Screening, vol. 1, No. 2, pp. 75–80, 1996.

Lorin A. Thompson and Jonathan A. Ellman, "Synthesis and Applications of Small Molecule Libraries," Chemistry Review, vol. 96, No. 1, pp. 555–600, 1996.

Donald F. Phillips, "Making new drugs via combinatorial chemistry," Journal of the American Medical Association, vol. 275, No. 21, pp. 1624–1626, Jun. 5, 1996.

Derek Hook, "Ultra high–throughput screening—a journey into Nanoland with Gulliver and Alice," Drug Discovery, vol. 1, No. 7, pp. 267–268, Jul. 1996.

John P. Manfredi et al., "Yeast ∝ mating factor structure–Activity relationships derived from genetically selected peptide agonist and antagonist of Ste2p," Molecular and cellular biology, vol. 16, No. 9, pp. 4700–4709, Sep. 1996.

James R. Broach and Jeremy Thorner, "High–throughput screening for drug discovery," Nature, vol. 384, supplement to issue No. 6604, pp. 14–16, Nov. 7, 1996.

Handbook of Instrumental Techniques for Analytical Chemistry, Chapter 16: Raman Spectroscopy, pp. 285–307, Jun. 4, 1997.

Dejan Bojanic et al., "Factors for the successful integration of assays, equipment, robotics, and software," *High Throughput Screening The Discovery of Bioactive Substances*, pp. 493–508, 1997.

John C. W. Comley et al., "A 384–HTS for human factor VIIa: Comparison with 96– and 864– well formats," Journal of Biomolecular Screening, vol. 2, No. 3, pp. 171–178, 1997.

Jill H. Hardin and Frank R. Smietana, "Automating combinatorial chemistry: challenges and pitfalls," *High Throughput Screening The Discovery of Bioactive Substances*, pp. 251–261, 1997.

Alfred J. Kolb et al., "Homogeneous, Time–resolved fluorescence method for drug discovery," *High Throughput Screening The Discovery of Bioactive Substances*, pp. 345–360, 1997.

Alfred J. Kolb and Kenneth Neumann, "Beyond the 96–well microplate: instruments and assay methods for the 384–well format," Journal of Biomolecular Screening, vol. 2, No. 2, pp. 103–109, 1997.

C. X. Song et al., "Controlled release of U–86983 from double–layer biodegradable matrices: effect of additives on release mechanisms and kinetics," Journal of Controlled Release, vol. 45, pp. 177–192, 1997.

David Brown, "Future pathways for combinatorial chemistry," Molecular Diversity, vol. 2, No. 4, Apr. pp. 217–222, 1997.

Jonathan J. Burbaum et al., "New technologies for high–throughput screening," Current Opinion in Chemical Biology, vol. 1, issue 1, pp. 72–78, Jun. 1997.

Curt Suplee, The Detroit News, "Chemister: Low–tech idea speeds research", (Jun. 16, 1997), Available at http://det-news.com/1997/discover/9706/16/0610026.htm.

John G. Houston and Martyn Banks, "The chemical–biological interface: development in automated and miniaturised screening technology," Current Opinion in Biotechnology, vol. 8, No. 6, pp. 734–740 Dec. 1997.

Robert L. Rice et al., "A targeted library of small–molecule, tyrosine, and dual–specificity phosphatase inhibitors derived from a rational core design and random side chain," Biochemistry, vol. 36, No. 50, pp. 15965–15974, Dec. 16, 1997.

Melissa E. Lenczewski and LaFonna L. Kananen, "Automated Screening Method for Determining Optimum Preservation Systems for Personal and Home Care Products," Journal of AOAC International, vol. 81, No. 3, pp. 534–539, 1998.

Nathanael S. Gray, "Exploiting Chemical Libraries, Structure, and Genomics in the Search for Kinase Inhibitors," Science, vol. 281, No. 5376, pp. 533–538, Jul. 24, 1998.

Scott Braxton and Tod Bedilion, "The integration of microarray information in the drug development process," Current Opinion in Biotechnology, vol. 9, No. 6, pp. 643–649, Dec. 1998.

Jesus E. Gonzalez and Paul A. Negulescu, "Intracellular detection assays for high–throughput screening," Current Opinion in Biotechnology, vol. 9, No. 6, Dec. 1998.

X. D. Xiang, "Combinatorial Materials Synthesis and High–Throughput Screening: An Integrated Materials Chip Approach to Mapping Phase Diagrams and Discovery and Optimization of Functional Materials," Biotechnology and Bioengineering—Combinatorial Chemistry, vol. 61, No. 4, 1998/1999.

Eric W. McFarland and W. Henry Weinberg, "Combinatorial approaches to materials discovery," Biotechnology, vol. 17, No. 3, pp. 107–115, Mar. 1999.

L. Van Hijfte et al., "Combinatorial chemistry, automation and molecular diversity: new trends in the pharmaceutical industry," Journal of Chromatography, vol. 725, No. 1, pp. 3–15, Apr. 2, 1999.

Trish Appleton, "Combinatorial chemistry and HTS—feeding a voracious process," Drug Discovery Today, vol. 4, No. 9, pp. 398–400, Sep. 1999.

Jesus E. Gonzalez et al., "Cell–based assays and instrumentation for screening ion–channel targets," Drug Discovery today, vol. 4, No. 9, pp. 431–439, Sep. 1999.

Nick Evens, "The use of automation in process development," Automated Synthetic Methods for Specialty Chemicals, pp. 68–82, 2–day Symposium New Century House, Manchester, UK Sep. 28–29, 1999.

Richard J. Bastin et al., "Salt selection and optimisation procedures for pharmaceutical new chemical entities," Organic Process Research & Development, vol. 4, No. 5, pp. 427–435, 2000.

Richard A. Houghten, "Parallel array and mixture–based synthetic combinatorial chemistry: tools for the next millennium," Annual Review of Pharmacology and Toxicology, vol. 40, pp. 273–282, 2000.

John S. Lazo and Peter Wipf, "Combinatorial Chemistry and Contemporary Pharmacology," The Journal of Pharmacology and Experimental Therapeutics, vol. 293, No. 3, 2000.

Javier Perez–Ramirez et al., "The six–flow reactor technology A review on fast catalyst screening and kinetic studies," Catalysis Today, vol. 60, pp. 93–109, Elsevier Science, 2000.

B. Yu. Shekunov and P. York, "Crystallization processes in pharmaceutical technology and drug delivery design," Journal of Crystal Growth, vol. 211, pp. 122–136, 2000.

Terry Threlfall, "Crystallization of polymorphs: thermodynamic insight into the role of solvent," Organic Process Research & Development, vol. 4, No. 5, pp. 384–390, 2000.

Fang Wang et al., "An investigation of solvent–mediated polymorphic transformation of progesterone using in situ Raman spectroscopy," Organic Process Research & Development, vol. 4, No. 5, pp. 391–395, 2000.

K. Westesen, "Novel lipid–based colloidal dispersions as potential drug administration sytems—expectations and reality," Colloid Polymer Science, vol. 278, pp. 608–618, 2000.

Linda L. Pearce et al., "Role of metallothionein in nitric oxide signaling as revealed by a green fluorescent fusion protein," Proceedings of the National Academy of Sciences of the United States of America, vol. 97, No. 1, pp. 477–488, Jan. 4, 2000.

Norman Lewis, "Shedding some light on crystallization issues: lecture transcript from the first international symposium on aspects of polymorphism and crystallization—chemical development issues," Organic Process Research & Development, vol. 4, No. 5, pp. 407–412, Mar. 24, 2000.

Recent Patents in combinatorial chemistry, Nature Biotechnology, vol. 18, p. 463, Apr. 2000.

Robert Spruijtenburg, "Example of selective preparation of a desired crystal modification by an appropriate choice of operating parameters," Organic Process Research & Development, vol. 4, No. 5, pp. 403–406, May 13, 2000.

Sanjay R. Chemburkar et al., "Dealing with the impact of Ritonavir polymorphs on the late stages of bulk drug process development," Organic Process Research & Development, vol. 4, No. 5, pp. 413–417, Jun. 21, 2000.

Richard J. Bastin et al., "Salt selection and optimisation procedures for pharmaceutical new chemical entities," Organic Process Research & Development, vol. 4, No. 5, pp. 427–435, Jul. 19, 2000.

Nick Hird, "Isn't combinatorial chemistry just chemistry?" Drug Discovery Today, vol. 5, No. 8, pp. 307–308, Aug. 2000.

Lian Yu et al., "Crystallization and Polymorphism of Conformationally Flexible Molecules: Problems, Patterns, and Strategies," Organic Process Research & Development, vol. 4, No. 5, pp. 396–402, Aug. 5, 2000.

Trevor Laird, "Special feature selection: polymorphism and crystallization," Organic Process Research & Development, vol. 4, No. 5, pp. 370–371, Aug. 24, 2000.

Martin Woods et al., "A scaleable combined resolution and improved dosage form for etodolac with recycle of the off–isomer," Organic Process Research & Development, vol. 4, No. 5, pp. 418–426, Aug. 24, 2000.

Wolfgang Beckmann, "Seeding the desired polymorph: background, possibilities, limitations, and case studies," Organic Process Research & Development, vol. 4, No. 5, pp. 372–383, Aug. 26, 2000.

Roberta Bursi and Marinus B. Groen, "Application of (quantitative) structure–activity relationships to progestagens: from serendipity to structure–based design," European Journal of Medicinal Chemistry, vol. 35, No. 9, pp. 787–796, Sep. 2000.

Torbjörn Lundstedt et al., "A combinatorial approach to lead finding and lead optimisation based on multivariate methods," Available at http://www.pharm.uni–duesseldorf.de/QSAR/126.htm, retrieved on Sep. 23, 2000.

Uwe Mueller et al., "Development of a technology for automation and miniaturization of protein crystallization," Journal of Biotechnology, vol. 85, pp. 7–14, 2001.

Uwe D. Neue et al., "Design of rapid gradient methods for the analysis of combinatorial chemistry libraries and preparation of pure compounds," Advances in Chromatography, vol. 41, pp. 93–136, 2001.

Michael W. Pantoliano et al., "High–density miniaturized thermal shift assays as a general strategy for drug discovery," Journal of Biomolecular Screening, vol. 6, No. 6, pp. 429–440, 2001.

Guido Koch, et al., "Selective synthesis of a new ascomycin rearrangement product (SDZ ASD732) on a pilot plant scale," Organic Process Research & Development, vol. 5, No. 3, pp. 211–215, Mar. 20, 2001.

Lance Stewart and Sara Moran, "Advances in high–throughput crystallization," CHIMICA OGGI/chemistry today, pp. 15–17, May 2001.

Helma Wennemers, "Combinatorial Chemistry: A Tool for the Discovery of New Catalysts," Combinatorial Chemistry & High Throughput Screening, vol. 4, No. 3, pp. 273–285, May 2001.

Horiba Group, "Pharmaceutical applications," Available at www.isainc.com, retrieved on Jun. 21, 2001, 6 pages.

Information relating to Raman spectroscopy and apparatus for performing Raman spectroscopy available from Avalon Instruments, Available at www.avaloninst.com, retrieved on Jun. 21, 2001, 10 pages.

Andrei Blasko, et al., "Revisiting the solubility concept of pharmaceutical compounds," Monatshefte fur Chemie Chemical Monthly, vol. 132, No. 7, pp. 789–798, Jul. 2001.

Patrick Jimonet et al., "High throughput organic synthesis, crystallography and early adme integration applied to the discovery of potent and orally bioavailable chromane and benzoxazine farnesyltransferae inhibitors," Abstracts of Papers for the 222nd American Chemical Society, Chicago, Illinois, Aug. 26–30, 2001.

Holger Elckhoff et al., "An automated platform for miniaturized protein crystallization," Greiner Bio–One.

John E. Koundourellis et al., "X–ray powder diffraction data for 12 drugs in current use," Journal of Chemical and Engineering Data,.

ABSTRACTS.

Mohammed Skouri, et al., "Dynamic light scattering stuides of the aggregation of lysozyme under Crystallization conditions," FEBS Lett., 1991, Abstract.

Stefan Fabry et al., "Expression of the glyceraldehyde–3–phosphate dehydrogenase gene from the extremely thermophilic archaebacterium *Methanothermus fervidus* in *E. coli*. Enzyme purification, Crystallization, and preliminary crystal data," FEBS Lett., 1988, Abstract.

J. A. Littlechild et al., "Phosphoglycerate kinase from the extreme thermophile *Thermus thermophilus*. Crystallization and preliminary x–ray data," FEBS Lett., 1987, Abstract.

Kit Fun Lau et al., "Chapter 23. Pharmacogenomics," Annu. Rep. Med. Chem., 2000, Abstract.

Michele Cargill et al., "Mining for SNPs: putting the common variants–common disease hypothesis to the test," Pharmacogenomics, 2000, Abstract.

Jicun Ren, "High–throughput screening genetic mutations/polymorphisms by capillary electrophoresis," Comb. Chem. High Throughput Screening, 2000, Abstract.

Michael Shi et al., "Technologies for detecting genetic polymorphisms in pharmacogenomics," Mol. Diagn. 1999, Abstract.

Rocio Moreira–Ludewig et al., "A rapid microtiter plate method for the detection of lysozyme release from human neutrophils," Journal Pharmocaol. Toxicol. Methods, 1992, Abstract.

Henk A. Kelders et al., "Automated protein crystallization and a new crystal form of a subtilisin: eglin complex," Protein Engineering, vol. 1, No. 4, pp. 301–303, 1987.

D. Maclean et al., Glossary of terms used in combinatorial chemistry, Journal of Combinatorial Chemistry, vol. 2, pp. 562–578, 2000.

Uni–Filters™ Available at http://www.whatman.com/poly/products/unifilters.html, retrieved on May 26, 2000.

Aleksey V. Soldatov et al., "Adjustment of transfer tools for the production of micro– and macroarrays," Biotechniques: The Journal of Laboratory Technology for Bioresearch, vol. 31, No. 4, pp. 848–854, Oct. 2001.

3$^{rd}$ International Symposium: Aspects of Polymorphism and Crystallisation—Chemical Development Issues, 2 day Symposium & Exhibition, Programme, 12$^{th}$ & 13$^{th}$ Nov. 2001.

Ronald C. George et al., "Automated dissolution testing of sustained release tablets," American Laboratory, vol. 20, No. 2, pp. 106, 100–112, 1988.

Titan™ Specialist Micro Titer Plates, Available at http://www.radleys.co.uk, date of receipt unknown.

ARES Pressure Reactors for Combinatorial Chemistry, Advanced ChemTech Automation, Available at www.advancedchemtech.com, date of receipt unknown.

John E. Koundourellis et al., "X–ray powder diffraction data for 12 drugs in current use," Journal of Chemical and Engineering Data, vol. 45, No. 6, pp. 1001–1006, Sep. 27, 2000.

DIFFRAC$^{plus}$ EVA Specification Sheet available from Bruker–AXS, Inc., available at www.bruker–axs.de, Specification Sheet was printed on Jan. 13, 2003.

* cited by examiner

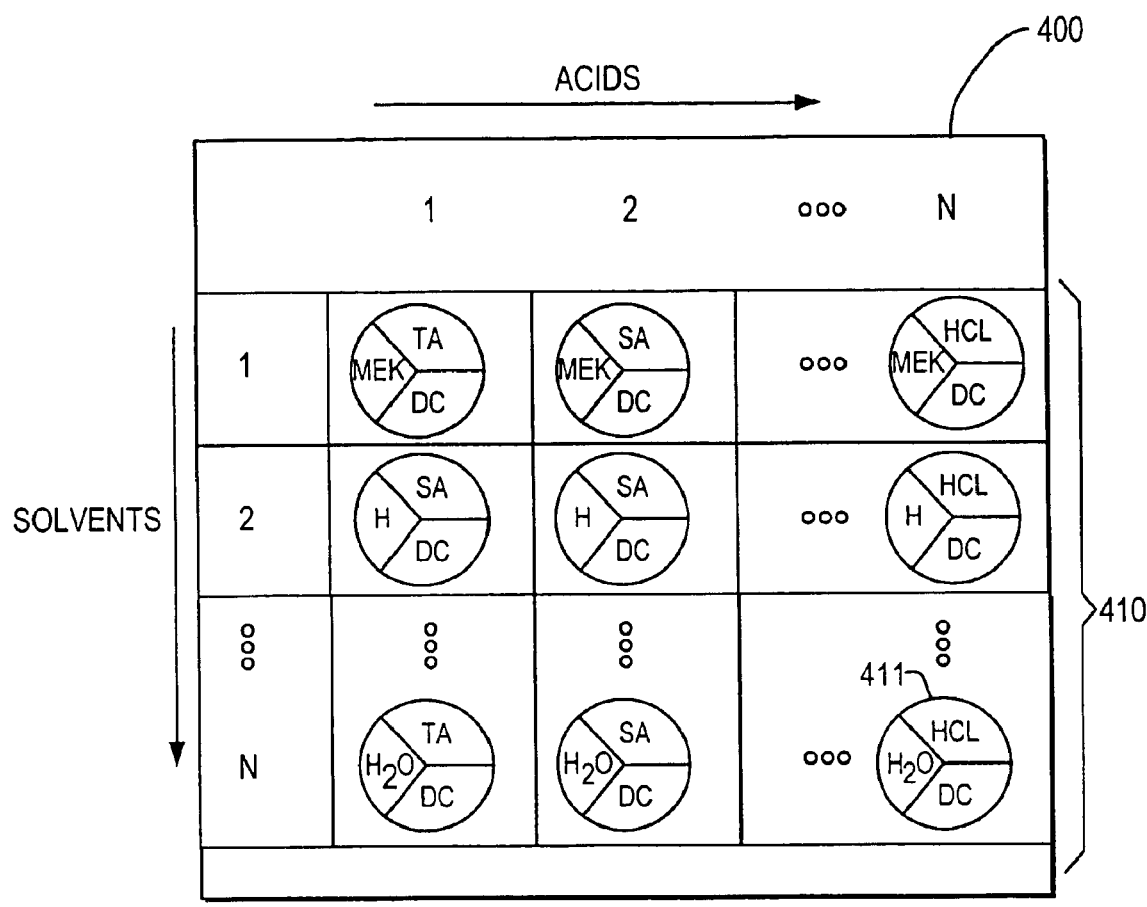
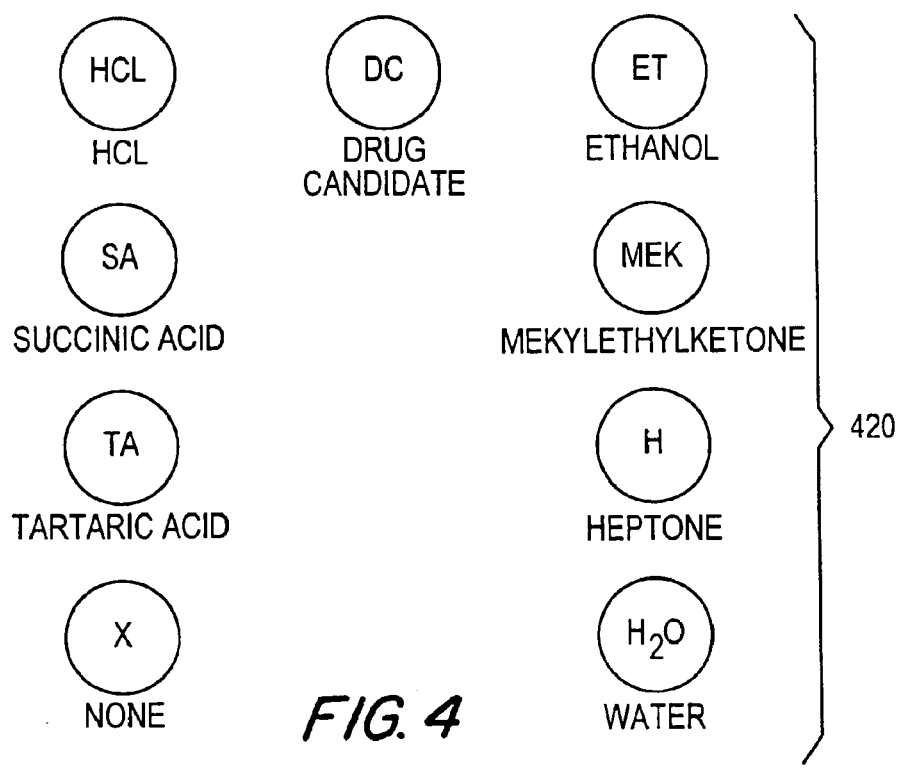
FIG. 4

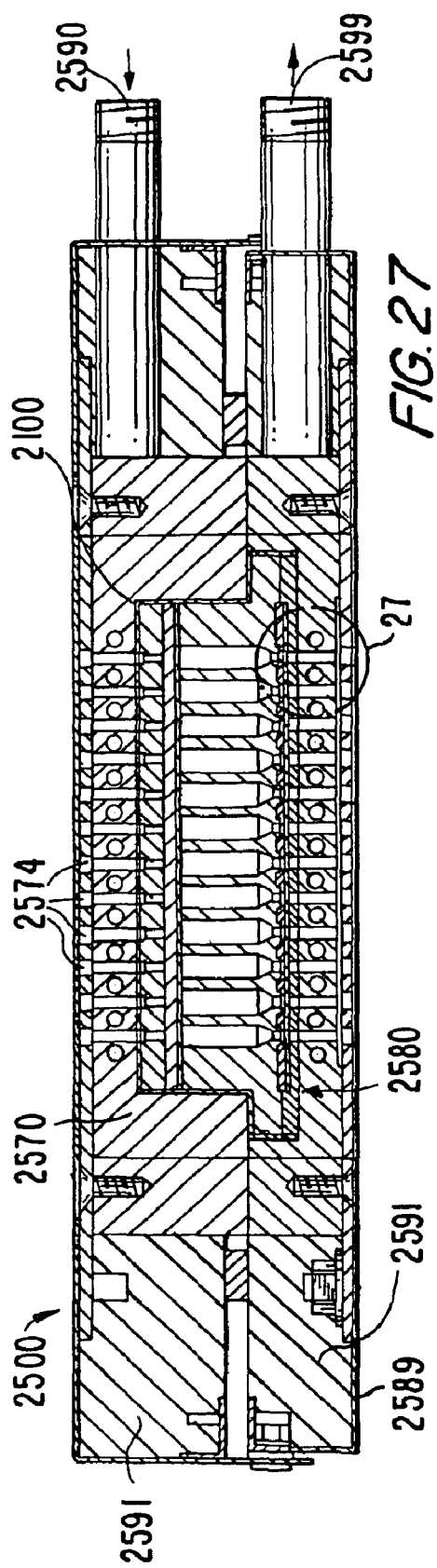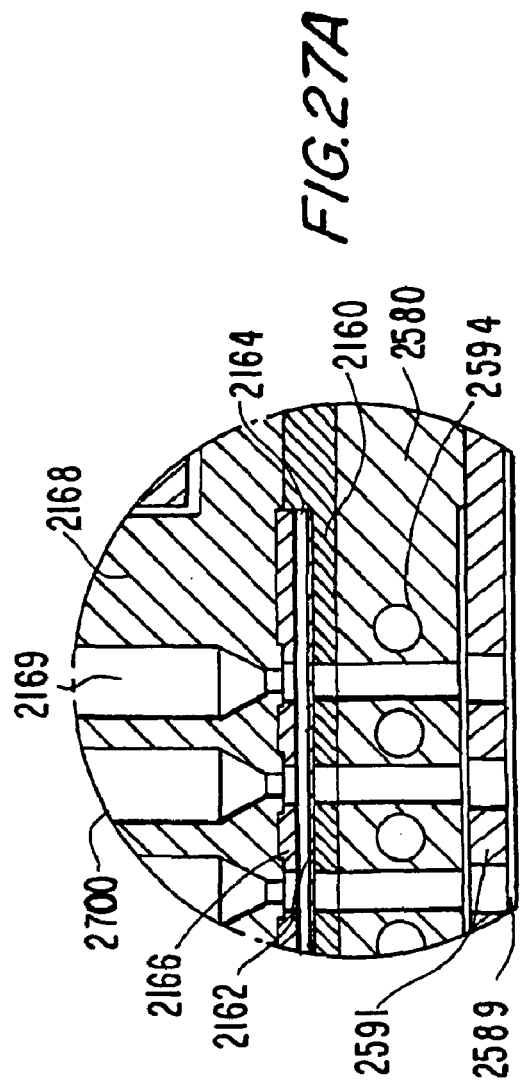

FIG.29A

| SOLVENT | CLASS | # | MW | n | $V_m$ | MP | BP | $\Delta H_{vap}$ | $\delta$ | $\mu$ | logS | logP | pKa | $\varepsilon$ | IE | $pK_{a+}$ |
|---|---|---|---|---|---|---|---|---|---|---|---|---|---|---|---|---|
| TRIFLUOROACETIC ACID | ACID | 1 | 114.02 | 1.48 | 77.0 | -15 | 72 | 41 | 10.93 | 2.28 | 8.00 | 0.5 | 0.23 | 39 | 11.5 | -8 |
| FORMIC ACID | ACID | 1 | 46.03 | 1.22 | 37.7 | 8 | 100 | 46.3 | 16.66 | 1.41 | 8.00 | -0.540 | 3.75 | 51.1 | 11.33 | -6 |
| ACETIC ACID | ACID | 1 | 60.05 | 1.04 | 57.7 | 15 | 115 | 51.6 | 14.26 | 1.74 | 8.00 | -0.17 | 4.756 | 6.15 | 10.65 | -6 |
| PROPIONIC ACID | ACID | 1 | 74.08 | 0.993 | 74.6 | -20.7 | 141 | 55 | 12.97 | 1.75 | 8.00 | 0.33 | 4.88 | 3.3 | 10.44 | -6 |
| METHANOL | ALCHOHOL | 2 | 32.04 | 0.791 | 40.5 | -98 | 64.7 | 37.83 | 14.44 | 1.70 | 8.00 | -0.77 | 15.5 | 32.63 | 10.84 | -205 |
| ETHANOL | ALCHOHOL | 2 | 46.07 | 0.816 | 56.5 | -114 | 78 | 42.46 | 13.01 | 1.69 | 8.00 | -0.31 | 15.9 | 24.30 | 10.48 | -2 |
| TRIFLUOROETHANOL | ALCHOHOL | 2 | 100.4 | 1.373 | 73.1 | -43 | 78 | 43.97 | 11.65 | 1.9 | 8.00 | 0.41 | 12.4 | 26.5 | 11.49 | -4 |
| 2-PROPANOL | ALCHOHOL | 2 | 60.1 | 0.785 | 76.6 | -89.5 | 82.4 | 45.48 | 11.59 | 1.66 | 8.00 | 0.05 | 18.0 | 18.3 | 10.17 | -2 |
| T-BUTANOL | ALCHOHOL | 2 | 74.12 | 0.775 | 95.6 | 25 | 83 | 46.74 | 10.52 | 1.64 | 8.00 | 0.35 | 19.0 | 17.7 | 9.9 | -2 |
| 1-PROPANOL | ALCHOHOL | 2 | 60.10 | 0.804 | 74.8 | -127 | 97 | 47.5 | 12.00 | 1.68 | 8.00 | 0.25 | 16.1 | 20.1 | 10.22 | -2 |
| 2-BUTANOL | ALCHOHOL | 2 | 74.12 | 0.808 | 91.7 | -115 | 98 | 49.86 | 11.11 | 1.70 | 2.258 | 0.61 | 17.6 | 16.56 | 9.88 | -2 |
| 1-BUTANOL | ALCHOHOL | 2 | 74.12 | 0.810 | 91.5 | -90 | 117.7 | 52.42 | 11.42 | 1.66 | 1.801 | 0.88 | 16.1 | 17.8 | 9.99 | -2 |
| 2-METHOXYETHANOL | ALCHOHOL | 2 | 76.09 | 0.965 | 78.8 | -85 | 124 | 45.2 | 11.38 | 2.20 | 8.00 | -0.77 | 14.8 | 17.2 | 10.13 | -3 |
| 3-METHYL-1-BUTANOL | ALCHOHOL | 2 | 88.15 | 0.809 | 109.0 | -117 | 130 | 55.63 | 10.80 | 1.82 | 1.427 | 1.16 | 16.1 | 14.7 | 10 | -2 |
| 2-ETHOXYTHETHANOL | ALCHOHOL | 2 | 90.12 | 0.93 | 96.9 | -90 | 135 | 48.23 | 10.62 | 2.08 | 8.00 | -0.32 | 14.8 | 29.6 | 9.6 | -2 |
| 1-PENTANOL | ALCHOHOL | 2 | 88.15 | 0.811 | 108.7 | -78 | 137 | 57.04 | 10.95 | 1.80 | 1.342 | 1.51 | 16.1 | 13.6 | 10.0 | -2 |
| 1-OCTANOL | ALCHOHOL | 2 | 130.23 | 0.827 | 157.5 | -15 | 196 | 70.98 | 10.20 | 1.76 | -0.268 | 2.97 | 16.1 | 10.3 | 10 | -2 |
| ETHYLENE GLYCOL | ALCHOHOL | 2 | 62.07 | 1.113 | 55.8 | -13 | 197 | 65.6 | 16.45 | 2.28 | 8.00 | -1.360 | 15.1 | 37.3 | 10.55 | -3 |
| WATER | WATER | 3 | 18.105 | 1.000 | 18.1 | 0 | 100 | 43.98 | 23.41 | 1.85 | 8.00 | -1.38 | 15.74 | 80.37 | 12.621 | -1.74 |
| FORMAMIDE | AMIDE | 4 | 45.04 | 1.134 | 39.7 | 2 | 210 | 60.15 | 18.63 | 3.70 | 8.00 | -1.510 | 13.7 | 110 | 10.16 | -0.48 |
| N,N-DIMETHYLFOMAMIDE | ALKYLAMIDE | 5 | 73.09 | 0.944 | 77.4 | -61 | 153 | 47.45 | 11.78 | 3.82 | 8.00 | -1.01 | 50.2 | 36.7 | 9.13 | -0.3 |
| N,N-DIMETHYLACETAMIDE | ALKYLAMIDE | 5 | 87.12 | 0.937 | 93.0 | -20 | 165 | 45.6 | 10.53 | 3.81 | 8.00 | -0.770 | 25.8 | 37.78 | 9.2 | -0.19 |
| BUTYL AMINE | AMINE | 6 | 73.14 | 0.740 | 98.8 | -49 | 78 | 35.84 | 8.98 | 1.0 | 8.00 | 0.97 | 35 | 5.4 | 8.73 | 10.77 |
| DIISOPROPYL AMINE | AMINE | 6 | 101.19 | 0.722 | 140.2 | -61 | 84 | 34.72 | 7.42 | 1.13 | 2.041 | 1.40 | 37.3 | 4.0 | 7.59 | 11.13 |
| TRIETHYL AMINE | AMINE | 6 | 101.19 | 0.726 | 139.4 | -115 | 88.8 | 34.96 | 7.46 | 0.66 | 1.867 | 1.45 | 51 | 2.42 | 7.53 | 11.01 |
| PYRIDINE | AMINE | 6 | 79.10 | 0.978 | 80.9 | -42 | 115 | 40.21 | 10.56 | 2.19 | 8.00 | 0.65 | 38.3 | 12.3 | 9.26 | 5.21 |
| ETHYLENE DIAMINE | AMINE | 6 | 60.01 | 0.899 | 66.8 | 9 | 118 | 45.01 | 12.34 | 1.99 | 8.00 | -2.04 | 35 | 14.2 | 8.6 | 9.92 |
| MORPHOLINE | AMINE | 6 | 87.12 | 0.999 | 87.2 | -6 | 129 | 42.40 | 10.46 | 1.5 | 8.00 | -086 | 35 | 7.33 | 8.88 | 8.33 |
| NITROMETNANE | NITRO | 7 | 61.04 | 1.127 | 54.2 | -29 | 101 | 38.36 | 12.58 | 3.46 | 2.061 | -0.35 | 10.2 | 39.4 | 11.08 | -12 |
| NITROETHANE | NITRO | 7 | 75.07 | 1.045 | 71.8 | -90 | 114 | 41.6 | 11.41 | 3.65 | 1.672 | 0.18 | 10.9 | 28.0 | 10.92 | -12 |
| 2-NITROPROPANE | NITRO | 7 | 89.09 | 0.992 | 89.8 | -93 | 120 | 41.3 | 10.16 | 3.73 | 1.230 | 0.93 | 11.4 | 26.74 | 10.74 | -12 |
| 1-NITROPROPANE | NITRO | 7 | 89.09 | 0.998 | 89.3 | -108 | 132 | 43.39 | 10.47 | 3.66 | 1.176 | 0.87 | 8.5 | 24.70 | 10.78 | -12 |
| NITROBENZENE | NITRO | 8 | 123.11 | 1.196 | 102.9 | 5 | 210 | 56.10 | 11.16 | 4.22 | 0.320 | 1.85 | 20 | 34.82 | 9.94 | -10.7 |
| ACETONE | KETONE | 9 | 58.08 | 0.791 | 73.4 | -94 | 56 | 31.27 | 9.68 | 2.88 | 8.00 | -0.24 | 20 | 20.7 | 9.703 | -7.2 |
| 2-BUTANONE | KETONE | 9 | 72.11 | 0.805 | 89.6 | -87 | 80 | 34.92 | 9.30 | 2.50 | 2.348 | 0.29 | 20.3 | 18.5 | 9.52 | -7 |
| METHYLISOPROPYL KETONE | KETONE | 9 | 86.13 | 0.805 | 107.0 | -92 | 94 | 36.87 | 8.77 | 2.8 | 1.778 | 0.84 | 21.5 | 10.37 | 9.31 | -7 |
| 3-PENTANONE | KETONE | 9 | 86.13 | 0.813 | 105.9 | -40 | 102 | 38.68 | 9.04 | 2.82 | 1.682 | 0.99 | 20.3 | 17.0 | 9.31 | -7 |
| 2-PENTANONE | KETONE | 9 | 86.13 | 0.802 | 107.4 | -78 | 105 | 38.46 | 8.95 | 2.70 | 1.637 | 0.91 | 21 | 15.4 | 9.38 | -7 |
| METHYLISOBUTYL KETONE | KETONE | 9 | 100.16 | 0.801 | 125.0 | -80 | 117 | 40.65 | 8.54 | 2.7 | 1.279 | 1.31 | 21 | 13.11 | 9.3 | -7 |
| CYCLOPENTANONE | KETONE | 9 | 84.12 | 0.951 | 88.5 | -51 | 130 | 42.77 | 10.43 | 3.13 | 0.963 | 0.63 | 19.4 | 13.58 | 9.26 | -7 |
| CYCLOHEXANONE | KETONE | 9 | 98.15 | 0.947 | 103.6 | -47 | 155 | 45.09 | 9.91 | 3.24 | 0.398 | 0.81 | 20.1 | 18.2 | 9.16 | -7 |
| ETHYLFORMATE | ESTER | 10 | 74.08 | 0.917 | 80.8 | -80 | 53 | 32.11 | 9.36 | 1.93 | 1.945 | 0.230 | 53 | 7.2 | 10.61 | -6.5 |
| METHYL ACETATE | ESTER | 10 | 74.08 | 0.932 | 79.5 | -98 | 58 | 32.5 | 9.50 | 1.72 | 2.386 | 0.18 | 23.3 | 6.68 | 10.25 | -6.5 |

FIG.29B

| SOLVENT | CLASS | # | MW | n | $V_m$ | MP | BP | $\Delta H_{vap}$ | $\delta$ | $\mu$ | logS | logP | pKa | $\varepsilon$ | IE | $pK_{a+}$ |
|---|---|---|---|---|---|---|---|---|---|---|---|---|---|---|---|---|
| ETHYL ACETATE | ESTER | 10 | 88.11 | 0.902 | 97.7 | -84 | 77 | 35.69 | 9.01 | 1.78 | 1.903 | 0.73 | 24.5 | 6.02 | 10.01 | -6.5 |
| ISOPROPYL ACETATE | ESTER | 10 | 102.13 | 0.872 | 117.1 | -73 | 89 | 37.2 | 8.42 | 1.8 | 1.490 | 1.02 | 23.3 | 6.3 | 9.99 | -6.5 |
| PROPYL ACETATE | ESTER | 10 | 102.13 | 0.888 | 115.0 | -95 | 102 | 39.77 | 8.80 | 1.78 | 1.276 | 1.24 | 22.8 | 6.002 | 10.04 | -6.5 |
| ISOBUTYL ACETATE | ESTER | 10 | 116.16 | 0.868 | 133.8 | -99 | 116 | 35.9 | 7.73 | 1.86 | 0.799 | 1.780 | 24 | 5.07 | 9.97 | -6.5 |
| BUTYL ACETATE | ESTER | 10 | 115.16 | 0.882 | 131.7 | -78 | 125 | 43.89 | 8.67 | 1.87 | 0.924 | 1.78 | 22.4 | 5.01 | 9.92 | -6.5 |
| ACETONITRILE | NITRILE | 11 | 41.05 | 0.786 | 52.2 | -48 | 81 | 33.4 | 11.90 | 3.92 | 8.00 | -0.34 | 25 | 37.5 | 12.2 | -11 |
| PROPIONITRILE | NITRILE | 11 | 55.08 | 0.772 | 71.3 | -93 | 97 | 36.19 | 10.63 | 4.02 | 8.00 | 0.16 | 25.2 | 29.7 | 11.85 | -11 |
| BUTYRONITRILE | NITRILE | 11 | 69.11 | 0.794 | 87.0 | -112 | 116 | 39.41 | 10.07 | 3.82 | 0.519 | 0.53 | 25 | 20.7 | 11.2 | -11 |
| BENZONITRILE | NITRILE | 12 | 103.12 | 1.01 | 102.1 | -13 | 191 | 55.48 | 11.14 | 4.18 | 0.301 | 1.56 | 37.5 | 26.0 | 9.73 | -10 |
| DIMETHYL SULFOXIDE | SULFOXIDE | 13 | 78.13 | 1.101 | 71.0 | 18 | 189 | 52.89 | 13.03 | 3.96 | 8.00 | -1.35 | 24.5 | 46.45 | 9.1 | -0.65 |
| DIETHYL ETHER | ETHER | 14 | 74.12 | 0.715 | 103.7 | -116 | 34.6 | 27.37 | 7.58 | 1.15 | 1.781 | 0.89 | 53 | 4.335 | 9.51 | -2.39 |
| METHYL-T-BUTYL ETHER | ETHER | 14 | 88.15 | 0.740 | 119.1 | -109 | 56 | 30.04 | 7.44 | 1.2 | 1.708 | 1.24 | 53 | 5 | 9.48 | -3.5 |
| DIMETHOXYMETHANE | ETHER | 14 | 76.09 | 0.852 | 89.3 | -105 | 64 | 28.89 | 8.41 | 0.74 | 8.00 | 0.22 | 53 | 2.7 | 9.7 | -3.5 |
| TETRAHYDROFURAN | ETHER | 14 | 72.11 | 0.889 | 81.1 | -108 | 66 | 32.16 | 9.35 | 1.63 | 8.00 | 0.46 | 53 | 7.58 | 9.4 | -2.08 |
| ISOPROPLY ETHER | ETHER | 14 | 102.17 | 0.725 | 140.9 | -85.5 | 68 | 32.26 | 7.11 | 1.13 | 0.944 | 1.488 | 53 | 3.88 | 9.20 | -3.5 |
| 1,2-DIMETHOXYETHANE | ETHER | 14 | 90.12 | 0.867 | 103.9 | -58 | 85 | 36.47 | 8.84 | 2.08 | 8.00 | -0.21 | 53 | 7.3 | 9.3 | -3.5 |
| PROPYL ETHER | ETHER | 14 | 102.18 | 0.736 | 138.8 | -123 | 89 | 35.79 | 7.57 | 1.21 | 0.690 | 2.03 | 53 | 3.3 | 9.3 | -3.5 |
| 1,4-DIOXANE | ETHER | 14 | 88.11 | 1.034 | 85.2 | 11.8 | 101 | 38.66 | 10.07 | 0.00 | 8.00 | -0.27 | 53 | 2.209 | 9.19 | -2.92 |
| 1,2-DIETHOXYETHANE | ETHER | 14 | 118.18 | 0.842 | 140.4 | -74 | 121 | 43.27 | 8.33 | 0.00 | 1.923 | 0.66 | 53 | 3.90 | 9.2 | -3.5 |
| BUTYL ETHER | ETHER | 14 | 130.23 | 0.764 | 170.5 | -98 | 142 | 45.0 | 7.72 | 1.17 | -0.523 | 3.21 | 53 | 3.08 | 9.28 | -3.5 |
| BENZENE | AROMATIC | 15 | 78.12 | 0.874 | 89.4 | 5.5 | 80 | 33.93 | 9.17 | 0.00 | 0.253 | 2.13 | 40 | 2.284 | 9.244 | -16 |
| TOLUENE | AROMATIC | 15 | 92.14 | 0.865 | 106.5 | -93 | 110.6 | 38.06 | 8.94 | 0.36 | -0.279 | 2.73 | 37 | 2.379 | 8.828 | -14 |
| O-XYLENE | AROMATIC | 15 | 106.17 | 0.860 | 123.5 | -24 | 140 | 43.45 | 8.91 | 0.62 | -0.750 | 3.12 | 38 | 2.568 | 8.56 | -13 |
| CUMENE | AROMATIC | 15 | 120.19 | 0.864 | 139.1 | -96 | 153 | 45.15 | 8.56 | 0.79 | -1.215 | 3.66 | 38 | 2.38 | 8.73 | -14 |
| ANISOLE | AROMATIC | 15 | 108.14 | 0.995 | 108.7 | -37.5 | 154 | 46.91 | 9.88 | 1.38 | 0.017 | 2.11 | 46.0 | 4.33 | 8.2 | -6.2 |
| MESITYLENE | AROMATIC | 15 | 120.19 | 0.864 | 139.1 | -45 | 163 | 47.51 | 8.80 | 0.00 | -1.317 | 3.42 | 40 | 3.4 | 8.4 | -10 |
| TETRALIN | AROMATIC | 15 | 132.2 | 0.973 | 135.9 | -35 | 207 | 55.23 | 9.63 | 0.60 | -1.328 | 3.49 | 38 | 2.76 | 8.46 | -13 |
| PENTANES | HC | 16 | 72.15 | 0.626 | 115.3 | -130 | 36 | 26.75 | 7.09 | 0.00 | -1.420 | 3.39 | 50 | 1.844 | 10.28 | -20 |
| HEXANES | HC | 16 | 86.18 | 0.659 | 130.8 | -95 | 69 | 31.73 | 7.31 | 0.00 | -2.022 | 3.9 | 50 | 1.890 | 10.13 | -20 |
| CYCLOHEXANE | HC | 16 | 84.16 | 0.779 | 108.0 | 6.5 | 80.7 | 33.12 | 8.23 | 0.00 | -1.260 | 3.44 | 52 | 2.023 | 9.88 | -20 |
| HEPTANE | HC | 16 | 100.20 | 0.684 | 146.5 | -91 | 98 | 36.66 | 7.47 | 0.00 | -2.469 | 4.397 | 50 | 1.925 | 9.93 | -20 |
| ISOOCTANE | HC | 16 | 114.23 | 0.692 | 165.1 | -107 | 98 | 35.24 | 6.89 | 0.1 | -2.613 | 4.09 | 50 | 1.94 | 9.89 | -20 |
| METHYLCYCLOHEXANE | HC | 16 | 98.19 | 0.77 | 127.5 | -126 | 101 | 35.44 | 7.86 | 0.1 | -1.854 | 3.61 | 50 | 2.02 | 9.64 | -20 |
| OCTANE | HC | 16 | 114.23 | 0.703 | 162.5 | -57 | 126 | 41.53 | 7.58 | 0.00 | -3.180 | 5.18 | 50 | 1.95 | 9.8 | -20 |
| DECANE | HC | 16 | 142.29 | 0.73 | 194.9 | -30 | 174 | 51.9 | 7.78 | 0.00 | -4.284 | 5.01 | 50 | 1.99 | 9.65 | -20 |
| DECALIN | HC | 16 | 132.21 | 0896 | 147.6 | -125 | 190 | 49.4 | 8.72 | 0.00 | -3.051 | 4.20 | 50 | 2.18 | 9.35 | -20 |
| HEXAFLUOROBENZENE | ARYL HALIDE | 17 | 186.06 | 1.612 | 115.4 | -4 | 80 | 35.82 | 8.31 | 0.00 | -0.469 | 2.55 | 60 | 2.03 | 9.89 | -22 |
| FLUOROBENZENE | ARYL HALIDE | 17 | 96.10 | 1.024 | 93.8 | -42 | 85 | 34.68 | 9.06 | 1.60 | 0.188 | 2.27 | 39 | 5.42 | 9.2 | -16 |
| A,A,A-TRIFLUOROTOLUENE | ARYL HALIDE | 17 | 146.11 | 1.199 | 121.9 | -29 | 102 | 37.67 | 8.31 | 2.86 | -0.854 | 3.01 | 34.1 | 9.2 | 9.685 | -17 |
| OCTAFLUOROTOLUENE | ARYL HALIDE | 17 | 236.06 | 1.666 | 141.7 | -66 | 104 | 41.6 | 8.12 | 0.2 | -1.921 | 3.96 | 60 | 2.1 | 10.2 | -23 |
| CHLOROBENZENE | ARYL HALIDE | 17 | 112.56 | 1.107 | 101.7 | -45 | 132 | 41.0 | 9.52 | 1.69 | -0.303 | 2.84 | 37.5 | 5.708 | 9.07 | -16 |
| BROMOBENZENE | ARYL HALIDE | 17 | 157.01 | 1.491 | 105.3 | -31 | 156 | 44.54 | 9.77 | 1.70 | -0.351 | 2.99 | 34.3 | 5.4 | 9.00 | -15 |
| 1,2-DICHLOROBENZENE | ARYL HALIDE | 17 | 147.00 | 1.306 | 112.6 | -17 | 180 | 50.21 | 10.07 | 2.50 | -0.807 | 3.43 | 32 | 7.75 | 9.06 | -17 |

| SOLVENT | CLASS | # | MW | n | $V_m$ | MP | BP | $\Delta H_{vap}$ | $\delta$ | $\mu$ | logS | logP | pKa | $\varepsilon$ | IE | $pK_{a+}$ |
|---|---|---|---|---|---|---|---|---|---|---|---|---|---|---|---|---|
| 1,1-DICHLOROETHENE | CHC | 18 | 94.93 | 1.213 | 78.3 | -122 | 31 | 26.74 | 8.61 | 1.34 | 0.352 | 2.13 | 38 | 4.6 | 9.81 | -22 |
| DICHLOROMETHANE | CHC | 18 | 84.93 | 1.325 | 64.1 | -97 | 40 | 29 | 9.94 | 1.60 | 1.115 | 1.25 | 30 | 9.08 | 11.33 | -22 |
| CHLOROFORM | CHC | 18 | 119.38 | 1.492 | 80.0 | -63 | 61 | 31.4 | 9.29 | 1.01 | 0.900 | 1.97 | 18 | 4.806 | 11.37 | -22 |
| 1,1,1-TRICHLOROETHANE | CHC | 18 | 133.40 | 1.338 | 99.7 | -35 | 75 | 32.62 | 8.50 | 1.78 | 0.173 | 2.48 | 41 | 7.252 | 11 | -22 |
| 1,2-DICHLOROETHANE | CHC | 18 | 98.96 | 1.256 | 78.8 | -35 | 83 | 35.22 | 9.97 | 0.00 | 0.930 | 1.48 | 35 | 10.3 | 11.07 | -22 |
| TRICHLOROETHENE | CHC | 18 | 131.39 | 1.463 | 89.8 | -85 | 87 | 34.52 | 9.25 | 0.77 | 0.041 | 2.42 | 26 | 3.42 | 9.46 | -22 |
| 1,1,2-TRICHLOROETHANE | CHC | 18 | 133.40 | 1.435 | 93.0 | -37 | 112 | 40.28 | 9.86 | 1.25 | 0.645 | 1.89 | 23 | 9.4 | 11.0 | -22 |
| 1,1,2,2-TETRACHLOROETHANE | CHC | 18 | 167.85 | 1.586 | 105.8 | -43 | 147 | 45.72 | 9.88 | 0.00 | 0.471 | 2.39 | 20 | 8.5 | 11.1 | -22 |
| CARBON TETRACHLORIDE | PCC | 19 | 153.82 | 1.594 | 96.5 | -23 | 76 | 32.54 | 8.63 | 0.00 | -0.101 | 2.83 | 60 | 2.238 | 11.47 | -22 |
| TETRACHLOROETHYLENE | PCC | 19 | 165.82 | 1.623 | 102.2 | -22 | 121 | 39.72 | 9.33 | 0.00 | -0.699 | 3.4 | 60 | 2.5 | 9.326 | -22 |
| PERFLUOROHEXANE | PFC | 20 | 338.05 | 1.669 | 202.5 | -87 | 59 | 31.02 | 5.80 | 0.00 | -5.000 | 6.02 | 60 | 1.75 | 13.0 | -25 |
| PERFLUOROHEPTANE | PFC | 20 | 388.05 | 1.745 | 222.4 | -78 | 83 | 36.34 | 6.03 | 0.00 | -6.000 | 6.99 | 50 | 1.8 | 12.9 | -25 |
| PERFLUOROOCTANE | PFC | 20 | 438.06 | 1.766 | 248.1 | -25 | 103 | 41.16 | 6.11 | 0.00 | -7 | 7.95 | 60 | 1.8 | 12.8 | -25 |
| PERFLUORODECALIN | PFC | 20 | 462.08 | 1.908 | 242.2 | -10 | 142 | 44.51 | 6.44 | 0.00 | -7 | 7.80 | 60 | 1.9 | 12.4 | -25 |

FIG. 29C

APPARATUSES AND METHODS FOR CREATING AND TESTING PRE-FORMULATIONS AND SYSTEMS FOR SAME

CROSS-REFERENCE TO A RELATED PATENT APPLICATION

This application claims the benefit of U.S. Provisional Application No. 60/311,332, filed Aug. 10, 2001, the disclosure of which is hereby incorporated by reference in its entirety.

TECHNICAL FIELD OF THE INVENTION

The present invention relates to the field of research for pre-formulations or polymorphs. More particularly, the present invention is directed toward apparatus and methods for performing parallel synthesis and screening of salts and polymorphic forms of drug candidates.

BACKGROUND OF THE INVENTION

Combinatorial chemistry has revolutionized the process of drug discovery. See, for example, 29 Ace. Chem. Res. 1–170 (1996); 97 Chem. Rev. 349–509 (1997); S. Borman, Chem. Eng. News 43–62 (Feb. 24, 1997); A. M. Thayer, Chem. Eng. News 57–64 (Feb. 12, 1996); N. Terret, 1 Drug Discovery Today 402 (1996)). Although combinatorial chemistry has to a great extent eliminated the bottleneck in drug discovery, other bottlenecks have emerged in getting a drug to market. One such bottleneck is the selection of salts of active pharmaceutical ingredients in such drugs. Another is the identification of polymorphs and pseudo-polymorphs of drug candidates.

A salt of a compound often has characteristics that are desirable for a drug candidate, including increased water solubility and a higher melting point than the compound itself. Further, different salts of a drug candidate may have disparate and discrete physical properties from one another. For instance, different salts of a compound may have different melting points or solubilities, or may crystallize in different forms and/or under different conditions. Traditional salt selection for a drug candidate requires mixing (e.g., sometimes referred to as synthesizing or formulating) a number of different salts of a compound, recrystallizing the salts under a number of different conditions to generate a crystalline form, and then characterizing the salt. This process is time consuming because it has to be reiterated a number of times to identify salts with desirable characteristics.

Not only do different salts of a drug candidate have different properties, different polymorphs of the salt or of the neutral compound may also have different physical characteristics. As is known in the pharmaceutical industry, the polymorphic state of an active pharmaceutical ingredient can change the biological profile of the drug. An industry journal published an entire special issue on this topic, Organic Process Research & Development (Vol. 4, No. 5, 2000 and in particular pp. 370–435), with the issue pointing out, inter alia, that polymorphism and crystallization issues affect many industries as well as pharmaceutical compounds, including explosives, color chemicals and food additives.

Traditional polymorph characterization requires recrystallizing a neutral drug candidate or a drug candidate salt, characterizing the crystals, and comparing the crystals to known forms to identify polymorphs. These steps must be reiterated a large number of times in order to identify all of the polymorphs of a given neutral compound or drug candidate salt. Thus, although characterization of polymorphs is advantageous and, in some cases, necessary, the traditional methods of identifying and isolating polymorphs can be tedious. Crystallizing new polymorphs often requires hundreds to thousands of experiments that analyze the effects of varying critical parameters such as temperature, solvent and solvent mixtures, mixing time, cooling rates, stirring rates, and concentrations and methods and process for precipitation, cooling, evaporation, slurry, and thermocycling.

One reference in the special issue of Organic Process Research & Development discloses the use of a certain technique for the screening of potential salts of pharmaceutically active compounds. Bastin et al. "Salt Selection and Optimisation Procedures for Pharmaceutical New Chemical Entities", Organic Process Research & Development 2000, 4, 427–435, incorporated herein by reference. The paper discloses a library design for an array of different salts in different solvents. While this reference discloses a start at speeding up the pre-formulation process, it fails to follow through with screening in parallel or with high throughput research into crystallographic polymorphs.

In addition, several published patent applications in the area of high throughput or combinatorial materials science disclose a process in which the materials created in the process can be screened on the same plate in which they are synthesized. For example, WO 99/59716 discloses and claims creating solids on a removable reactor base plate and then performing X-RAY analysis of the solids. WO 01/34290 and WO 01/34291 reportedly relate to a "work station" that employs an array that can be transferred between preparing, screening and characterization stations without requiring sample handling, preparation or transfer steps. WO 96/11878 also discloses parallel crystallization and screening of materials on a substrate.

WO 01/51919 also reportedly relates to a high throughput method for formation, identification and analysis of diverse solid-forms; however, the methods in this application are extremely broad and vague, such that the publication serves merely to identify many problems without providing a solution beyond suggesting high throughput methods. Other publications reportedly disclose methods of analyzing polymorphs. For instance, WO 01/82659 reports a method of using X-ray diffraction to screen polymorphs. The publication reports that one can compare the X-ray diffraction pattern acquired for a polymorph and compare it with the X-ray diffraction patterns of known polymorphs of a compound. However, the publication does not disclose methods for rapidly generating the polymorph samples or for using the polymorph comparisons in drug discovery.

Given the rapid process of drug discovery in the pharmaceutical industry through combinatorial chemistry, a need generally exists in industry for a combinatorial or high throughput method and apparatus for the research, discovery and development of polymorphs formed by drug candidates. However, despite the cited work, a process for the systematic high throughput research of pre-formulations has not been directly disclosed.

SUMMARY OF THE INVENTION

The present invention addresses this problem by providing a universal system that addresses the need to characterize drug candidates. The system provides, inter alia, generation of libraries, salt selection, polymorph characterization, and other high throughput methods for identifying and characterizing physical properties of drug candidates, using a variety of reacting and screening options.

Specifically, the invention provides methods, systems and apparatus for performing combinatorial or high throughput preparing, screening and characterization of drug candidate salts and/or crystalline structures (e.g., polymorphs) of drug candidates. These methods, systems and apparatus decrease the time needed to find a suitable form of active ingredient for formulation and allow for additional forms of active pharmaceutical ingredients to be discovered, which may allow for additional patent coverage, a decreased risk of unwanted polymorphs appearing in later stages of pharmaceutical development or of competitors discovering a related form. In addition, the novel apparatus and methods disclosed herein allow for multiple different drug candidates to be formulated, crystallized and characterized in parallel, thereby creating a high throughput methodology for pharmaceutical research organizations and others.

In one aspect, the invention provides a workflow that enhances the process of identifying and characterizing potential active pharmaceutical ingredients (API) from a drug candidate. In one embodiment of the invention, salts of a drug candidate of interest are formulated using high throughput and/or combinatorial methods. The drug candidate salts are then screened to determine a variety of parameters or properties, which may include, without limitation, solubility, partition coefficient (log P), crystallinity, hygroscopicity, Raman spectral pattern, X-ray diffraction (XRD) pattern and melting point. The data obtained from the screening are then analyzed to identify suitable drug candidate salts. In a preferred embodiment, the formulation, screening and analysis are automated. Further, the workflow may be performed using the apparatus described herein. In another embodiment, the analysis is performed as the data are generated so that suitable salts may be rapidly identified. The workflow may be terminated after a suitable salt is selected. In a preferred embodiment, the suitable salt is then subjected to polymorph formulation, characterization and analysis.

In another aspect, the invention uses high throughput and combinatorial methods to crystallize, characterize and analyze polymorphs and/or pseudo-polymorphs of a drug candidate of interest. Generating and analyzing polymorphs may follow directly after salt selection or may be performed using an existing drug candidate. The drug candidate may be a neutral, acidic or basic compound, or may be a drug candidate salt. In one embodiment, the drug candidate is recrystallized under a variety of conditions using high throughput and/or combinatorial methods. The drug candidate crystals are then screened to determine a number of characteristics of the crystal, including, without limitation, solubility, log P, crystallinity, melting point, hygroscopicity, crystal morphology and birefringence, as well as X-ray diffraction, infrared (IR), Near IR and Raman spectroscopy, among others. The data obtained from the screening are then analyzed to identify the crystalline structures of the recrystallized drug candidate. Polymorphs of a recrystallized drug candidate may then be categorized according to the crystalline structure of the polymorph. In a preferred embodiment, polymorph recrystallization, screening and analysis are automated, and may be performed with the apparatus described herein. In another preferred embodiment, the analysis is performed as the data are generated so that different polymorphs and the conditions that produced them may be rapidly identified.

The invention further provides a method for selecting solvents for salt selection or polymorph generation. The invention further provides apparatus for high throughput salt preparation, recrystallization, solubility analysis, Raman and X-ray diffraction spectral analysis, and melting point determinations. The invention also provides hardware and software for controlling the salt selection and polymorph characterization methods of the invention and provides systems for automated high throughput operation of these methods.

Thus, one aspect of the invention is directed toward a high throughput method for preparing and characterizing different salts of a drug candidate. In one embodiment, a library is provided having a plurality of library members, wherein each library member comprises at least one drug candidate, and reacting in parallel each of the library members with an acid, base or salt to form different salts (e.g., complex salts or neutrals) of at least one drug candidate. In one embodiment, each library member may further comprise a solvent. In a preferred embodiment, the first library is comprised of at least eight members in regions on a first substrate, wherein the at least eight members comprises at least one drug candidate in an amount of between 0.05 and 50 mg of sample, reacting in parallel each of the at least eight members with an acid, base or salt to form different salts of at least one drug candidate. In another preferred embodiment, the drug candidate is present in an amount of less than 10 mg. In a further embodiment, the salts are produced as crystals in glass microtiter plates by cooling, evaporation, precipitation, slurry, or solvent gradients of aliquots of hot solutions.

In one embodiment, the drug candidate salts form crystalline structures. The drug candidate salt crystals and the supernatant or mother liquor may be left together or may be separated from each other after the salt reaction step, such that the crystals reside on the substrate, typically in regions so that the crystals can be screened individually. The method further provides for screening the crystals to identify new forms while said crystals reside on the substrate, as well as screening the supernatant or mother liquor for solubility of one or more drug candidate salts in each of the different solvents or solvent mixtures.

In general, salts are screened for at least two properties using various tests such as, for example, birefringence, melting point, solubility, hygroscopicity, Raman spectroscopy pattern, crystal morphology, X-ray powder diffraction pattern, infrared, near infrared or any other suitable test. In another embodiment, the salts are screened for at least three properties, four properties or five properties. In one embodiment, the salts are screened for at least birefringence, melting point, solubility, Raman spectroscopy pattern and X-ray powder diffraction pattern.

Another aspect of the invention is polymorph identification and/or characterization of a selected drug candidate. The drug candidate may be a neutral, acidic or basic compound or may be a salt of a drug candidate. In one embodiment, a library is provided and may include a plurality of members that each contain at least one drug candidate and at least one solvent. The library members are subjected to crystallizing conditions in parallel for each of the plurality of members on a substrate in different solvents or solvent mixtures. Each of the members are then screened to identify and/or characterize different crystalline structures of at least one drug candidate. In one embodiment, the library comprises at least eight members in an amount from 0.05 to 50 mg each, preferably less than 20 mg each. In a further embodiment, the polymorphs are produced in glass microtiter plates or other optically transmissive substrate by cooling, evaporation, precipitation by an anti-solvent, slurry, or solvent gradients of aliquots of hot solutions. In another embodiment, the polymorph characterization may be performed with a drug candidate or drug candidate salt without previously having performed salt selection.

In a further embodiment, the crystalline structures comprising the crystals and the supernatant or mother liquor is separated from each other after the recrystallization step such that the crystals reside on a substrate, typically in regions so that the crystals can be screened individually or in parallel. The method further provides for screening the crystals for at least crystallinity while the crystals reside on the substrate, as well as screening the supernatant or mother liquor for solubility of the one or more drug candidates in the different solvents or solvent mixtures. Other screening tests can be selected from a variety of tests, but a sufficient number of tests are performed to make a determination of the number of polymorphs and/or to identify polymorphs or salts thereof that may be suitable for drug formulation.

The crystals may be screened for any physical property that would help identify a polymorph. In general, at least two properties are screened. The properties may be birefringence, melting point, solubility, hygroscopicity, IR spectroscopy, Near IR spectroscopy, Raman spectroscopy, crystal morphology, X-Ray powder diffraction pattern or any other suitable screening method. In another embodiment, the crystals are screened for at least three properties, four properties or five properties to identify and characterize polymorphs. In one embodiment, the crystals are screened for at least birefringence, melting point, solubility, Raman pattern and X-ray powder diffraction pattern.

In one embodiment, crystals may be screened to identify and characterize polymorphs by optically imaging glass microtiter plates or another optically transmissive substrate that contains crystals of drug candidates or salts thereof. Two different optical scanning techniques can be used: transmission and reflection. Optical transmission occurs when an optical signal passes through an array of material samples. Optical reflection occurs when the optical signal is reflected by the material sample. Either one of these scanning techniques determine whether there are crystalline solids as well as determine the characteristics (size or habit) of any crystals. In one embodiment, the crystals may be optically imaged between polarization filters to measure birefringence, (e.g., to assess crystallinity).

In another embodiment, the crystals are analyzed by birefringence measurements before and after removal of a supernatant or mother liquor to detect unstable solvates or hydrates of drug candidates or salts thereof. In a further embodiment, individual wells or regions of the optically transmissive substrate may be imaged under magnification (with and without crossed polarization plates) to determine crystal habit and size. In yet another embodiment, scattered light measurements can be used to determine if there is a crystalline structure. In another embodiment, the crystalline structures may be characterized by their spectral properties, including, without limitation, Raman, IR, Near IR or X-ray diffraction spectroscopy to characterize the crystals formed on glass microtiter plates or other substrate. Preferred embodiments include Raman and/or X-ray diffraction spectroscopy. The invention also provides methods of using software to analyze the spectral data to identify polymorphs and/or solvates or hydrates contained in the arrays. In one embodiment, the optical imaging measurements (e.g., birefringence or crystal morphology), and the spectral measurements (e.g., Raman and X-ray diffraction) are made on the same samples without transfer of material from the substrate.

In another embodiment, the crystalline structures are formed on a glass substrate and/or in an apparatus that has an optical pathway to the regions or vessels so that optical measurements can be made while the crystalline structure is formed (sometimes referred to herein "in situ" measurements). The crystalline structures may be characterized by their optical or spectral properties, including, without limitation, birefringence, Raman spectral pattern, IR pattern, Near IR pattern, and/or light scattering. In some embodiments, the apparatus described herein can be used for these in situ measurements.

In another aspect, the melting temperature of the crystals may be determined. The method involves the steps of heating glass microtiter plates or other substrate comprising drug candidates crystallized under different crystallization conditions while making birefringence, scattering, other optical measurements to determine melting points, and/or other phase transitions including but not limited to loss of molecules of solvent or water from solvated crystals. In a preferred embodiment, the melting point of the crystals is determined using a parallel melting point apparatus.

In another aspect, the invention is directed toward making multiple copies of the arrays by "daughtering" from a parent set of solutions. Thus, in one embodiment, the invention is directed toward a method for testing drug candidates using daughter libraries, comprising forming a library comprised of a plurality members in regions on a first substrate, wherein each of the members comprises at least one drug candidate and a different solvent or solvent mixture, daughtering the members to a plurality of second substrates to form a plurality of daughter libraries; and subjecting the daughter libraries to different crystallization conditions, such as different crystallization methods (e.g., solvent evaporation and precipitation) and/or different crystallization parameters (e.g., different temperatures or different rates of cooling). In another embodiment, daughter libraries are constructed so that sets of identical crystals can be used in destructive measurements (e.g., melting point, hygroscopicity). In another embodiment, daughter libraries are constructed to archive libraries.

The various assemblies and computer software of this invention may be combined into a flexible workflow to identify and characterize polymorphs. Similarly, the invention also provides a flexible workflow to identify and characterize different drug candidate salts.

In another aspect, this invention is directed toward a solvent array, wherein the solvent array is chosen to achieve a degree of diversity based on an analysis of solvent parameters. Physical and chemical properties or other characteristics of the solvents are used to group the solvents into sets based upon similarities of their physical properties or characteristics. The number of physical or chemical properties or characteristics and the number of groups into which the solvents and solvent mixtures are clustered determines the type and degree of diversity in the solvent array for a given experiment or assay. The diverse solvent arrays may be used in the salt selection and polymorph generation methods described herein. The invention is also directed toward software to implement the use of solvent arrays in the methods and systems of the invention.

In another aspect, the invention is directed toward an apparatus that may be used for preparing an array of salts or crystals for screening. The apparatus comprises at least two different assemblies, but preferably three different assemblies, preferably with interchangeable parts between the different assemblies. In one embodiment, the apparatus comprises at least two assemblies, one for solubilizing drug candidates for recrystallization and/or synthesizing salts of drug candidates (the reactor assembly) and one for crystallizing the compounds (the crystallization assembly). In another embodiment, the apparatus comprises three assemblies, including a reactor assembly, a filtering assembly and a crystallizing assembly. Futher, one or more of the assemblies are provided separately (e.g., the filtering assembly).

In one aspect, the reactor assembly may include a reactor base having an array of a plurality of receptacles. Each of the receptacles may be isolated from each other to prevent cross-communication of materials contained therein. In one embodiment, the reactor base comprises thermal sensors embedded in the reactor base and a thermal block that surrounds the reactor base. The temperature of the thermal block may be computer controlled. The reactor assembly may be used in conjunction with a dispensing assembly that dispenses at least one object (e.g., ball or stirring flea) into a plurality of receptacles located in the reactor base.

In another aspect, the filtering assembly includes a reactor base comprising an array of a plurality of receptacles and a filtration subassembly. The filtration subassembly includes a plurality of pairs of holes, where each pair of holes is associated with a receptacle in the reactor base. One hole may be used for filtering a liquid before it is deposited into the associated receptacle. The other hole may be used to provide access to the associated receptacle without having to pass through a filter. Each pair of holes may isolated from each other to prevent cross-communication of fluid or vapor among other pairs of holes. Isolation may be accomplished using o-rings that are provided in the filtration subassembly. In particular, the o-rings may be constructed to include a large o-ring and a small o-ring. The large o-ring may surround each pair of holes to provide inter-pair isolation. The small o-ring may surround one of the holes in the pair to provide inter-hole isolation.

In another aspect, the crystallization assembly includes a reactor that comprises an optically transmissive substrate. The reactor may include a plurality of through-holes that correspond to regions on the substrate. The through-holes may be sealed such that each through-hole is isolated. In one embodiment, after the crystals form on the substrate, the substrate can be removed and subjected to screening test.

In another aspect, the invention is directed toward an apparatus that can determine the melting point of a crystal or other solid. In one embodiment, the melting point apparatus includes a thermal chamber and an image scanning device. An optically transmissive substrate supporting an array of materials (e.g., crystals) may be contained within the thermal chamber. The thermal chamber may heat the substrate at a predetermined rate (e.g., 1° C. per minute) to gradually heat the crystals on the substrate. As the substrate heats up, the image scanning device provides an optical signal to each material sample on the substrate and determines whether the crystal, if any, melts or changes phase, or whether the crystal changes composition (i.e., loss of water or solvent molecules).

The image scanning device may use birefringence imaging, light scattering, or other optical scanning techniques to determine when a crystal on the substrate melts. Birefringence imaging may be accomplished using an array of light emitters, polarizer filters and light detectors. In a preferred embodiment, the image scanning device is computer controlled. In addition, the computer may also control the rate in which the temperature of the thermal chamber is increased. Thus, the combination of temperature and birefringence imaging enables the resent invention to accurately detect the temperature at which each crystal melts or changes phase, or whether the crystal changes composition.

In another aspect, the invention is directed toward hardware and software for controlling various apparatuses associated with the invention. The hardware and software may control the dispensing of liquid into the reactor assembly, filtering assembly and/or crystallization assembly. For example, the present invention may be able to control an automated pipette system to dispense materials into a reactor assembly. In one embodiment, the hardware and software can be integrated with library design software.

Moreover, this invention is directed toward hardware and software for characterizing and analyzing one or more physical properties of the crystals obtained during the polymorph characterization or salt selection methods of the invention. In one embodiment, the software groups the crystals into families of compounds based upon similarities in one or more of their physical properties. The physical properties that are used to group the crystals into families may be defined by the user and/or may be obtained from previous characterization experiments. Further, the different polymorphs or salts may be grouped into families based upon their similarity to one another for one or more physical properties of interest within a user-defined deviation. Different families may be defined by the user based on the same or on different deviations. The software enables quick analysis of data obtained from screening experiments and provides for a high throughput methods.

Physical properties that may be used to sort polymorphs into families include, without limitation, crystal shape, melting point and spectral properties of crystals. In a preferred embodiment, the physical property that is used to sort polymorphs into families is a spectrum of the crystals obtained during the polymorph characterization. In one embodiment, the spectra may be obtained by Raman, infrared (IR), near-IR or X-ray diffraction spectroscopy, wherein the software sorts spectra into polymorph families, and in some embodiments this sorting is based on pattern matching. Thus, different polymorphs are grouped into families based upon their spectral similarities to one another within a user-defined variation, with different families being defined by the user.

In another aspect, the invention is directed toward a system for making and characterizing salts from at least one drug candidate. In one embodiment, the system may include a computer that controls dispensing, heating, and screening of the materials. The computer may control robotic equipment to dispense the drug candidate and one or more acids or bases into the receptacles to provide the mixture. Once the mixture is in a reactor assembly, a temperature-controlled housing that houses the reactor assembly may subject the reactor assembly to a predetermined temperature to promote dissolution of the drug candidate contained within the mixture.

Another aspect this invention is directed toward a system that tests a drug candidate in high throughput mode to make and characterize polymorphs. In one embodiment, the system includes a reactor assembly configured to contain a plurality of mixtures. The system may also include a crystallization assembly that is configured to contain crystallized compounds on a substrate. In addition, the system may include a temperature-controlled housing that is configured to contain an assembly such as, for example, a reactor assembly, filtration assembly, or a crystallization assembly and subject the assembly to a predetermined temperature. The system may also include a computer that controls the temperature-controlled housing and obtains data from the screening devices. The computer analyzes the data to determine if any polymorphs have formed and categorizes the polymorph into the appropriate family.

A further understanding of the nature and advantages of the present invention may be realized by reference to the remaining portions of the specification and the drawings.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 4 shows an illustrative library that can be modeled in accordance with the principles of the present invention;

FIG. 27 shows a cross-sectional view of the temperature-controlled housing that includes a crystallization assembly contained within the housing in accordance with the principles of the present invention;

FIG. 27A shows a detailed cross-sectional view of the temperature-controlled housing taken along circle 27 of FIG. 27 in accordance with the principles of the present invention;

FIGS. 29A, 29B and 29C show Table 3, which lists solvents useful for a process of this invention, including certain physical properties of the solvents that may be used in solvent selection that is in accordance with the principles of the present invention;

DETAILED DESCRIPTION OF THE INVENTION

Figure 1:
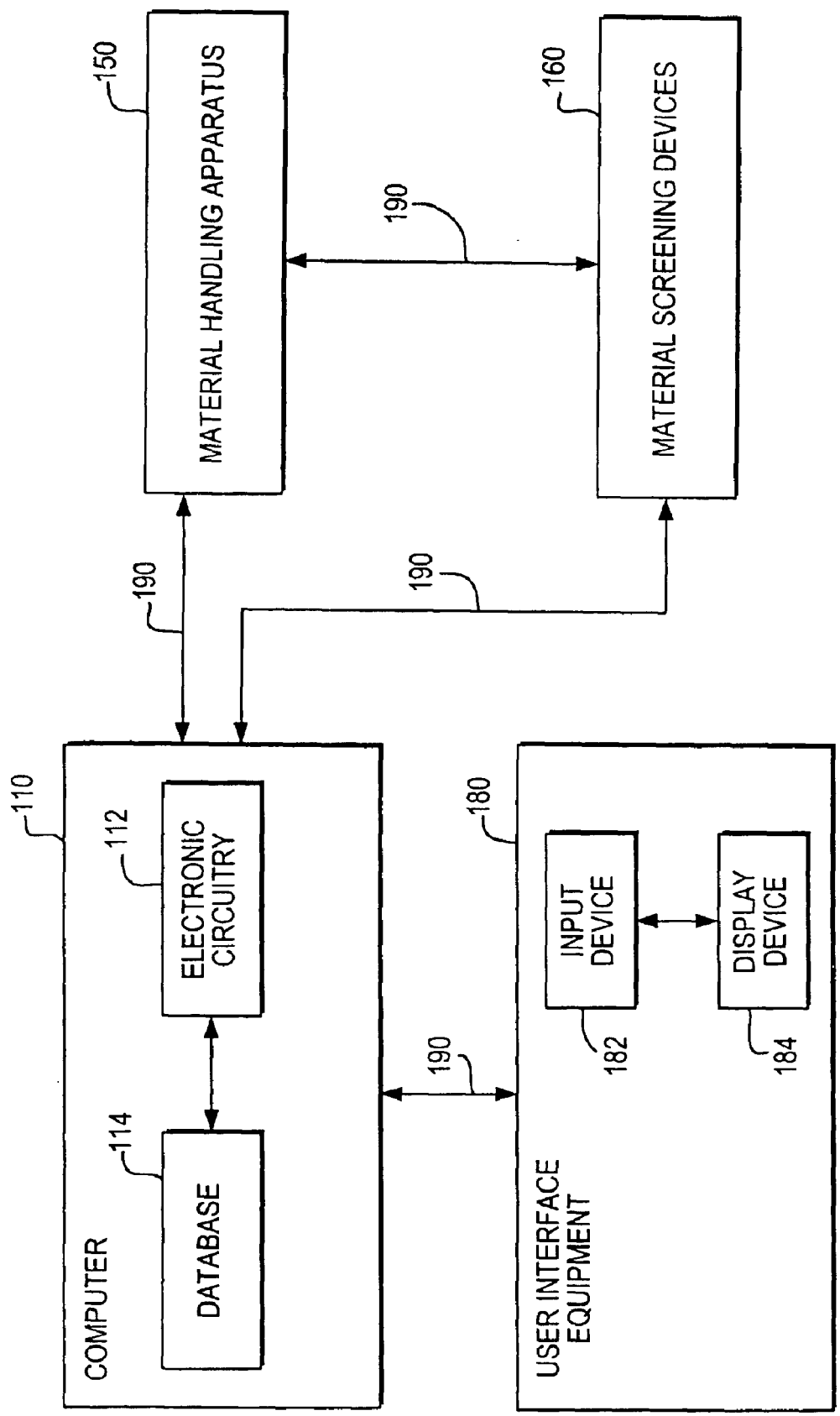
FIG. 1 shows an illustrative pre-formulation discovery tool system that is in accordance with the principles of the present invention.

Scientific and technical terms used in connection with the present invention shall have the meanings that are commonly understood by those of ordinary skill in the art with the supplemental definitions found herein, which are not intended to be contrary to the generally accepted definitions. Further, unless otherwise required by context, singular terms shall include pluralities and plural terms shall include the singular.

As discussed herein, an active pharmaceutical ingredient (API) is a specific compound (a salt or a neutral compound) that has been approved by the government for use in a pharmaceutical, e.g., it is safe and effective for a particular indication.

A drug candidate is a precursor to an API. A drug candidate may have shown efficacy under various assays for activity or safety under various toxicity assays. As used herein, a drug candidate is any compound of interest for which pre-formulation testing is desired to determine which form of the compound can or should be prepared. Pre-formulation testing can include salt selection and/or polymorph characterization and analysis. The methodology or process described in this patent application may be performed on API's and drug candidates. And, as those of skill in the art will appreciate, the exact API or drug candidate is not critical to this invention, but is typically a small molecule (as opposed to a protein) or a salt thereof. The term drug candidate, as used herein, refers to a neutral compound or a salt thereof, unless otherwise specified.

A polymorph of a compound, as used herein, is a crystal of a compound that is able to crystallize in more than one form. Thus, polymorphs of a compound refer to different crystalline forms of the compound. A polymorph may also be a pseudo-polymorph, which is a crystal of a compound that contains solvent or water molecules (i.e., solvates and hydrates, respectively) and thus differs from a crystal lacking solvent or water molecules. As used herein, the term polymorph refers to both polymorphs or pseudo-polymorphs, unless otherwise specified.

A "crystalline structure," as used herein, comprises a crystal and a supernatant (or mother liquor) formed when a solution crystallizes.

The term "solvent" refers to a liquid that is used to dissolve a drug candidate in the methods described herein. The term "solvent" is also intended to include mixtures of solvents (i.e., two or more different liquids that may or may not be miscible).

The term "salt reactant" refers to acids, bases and salts that are used to produce drug candidate salts. A "salt reactant" may be defined functionally as a substance that provides an ion (either a cation or an anion) that forms a salt with a drug candidate. Generally, a "salt reactant" is added in stoichiometric amounts to drug candidate, e.g., an approximately equal number of salt ions of the salt reactant are added as there are acidic or basic moieties on the compound of interest.

A "salt" is defined as a compound comprising anions and cations; that is, there is a proton transfer between the drug candidate and the acid or base. As used herein, a salt complex is a co-crystal of a drug candidate and a acid or base; that is, there is no proton transfer between the drug candidate and the acid or base. Unless indicated otherwise, the term "salt" as used herein includes both salts and salt complexes.

The term "crystallization" or "crystallize" refers to the process by which crystals form from a liquid solvent, generating a supernatant (sometimes referred to as a mother liquor) above the crystals. Crystallization also refers to a process in which crystals form from melts or sublimation. As used herein, a "crystal" is a solid in which the molecules are held together in a regular repeating internal arrangement.

As used herein, the term "precipitation" or "precipitate" refers to a process by which a solid is generated by addition of an anti-solvent to a drug candidate mixture. The solid may be in either crystalline or amorphous form.

The terms "recrystallization" and "recrystallize" are intended to mean crystallization of the drug candidate compounds from a solution, without intending to mean that the drug candidate compounds were crystals prior to being dissolved, unless otherwise indicated.

The term "library" as used herein refers to a plurality of experiments, samples or members, wherein the experiments, samples or members may or may not be physically associated. Thus, a library refers to members on a single substrate, on multiple substrates or on a portion of a substrate. In general, each member will have some data associated with it, which may include, e.g., drug candidate, salt form, solvent identity, spectral data, melting point, solubility, etc.

For purposes of the present invention, the term drug candidate is used generically to represent material compounds that are being developed and tested in a process. Further, as used herein, the terms "drug candidate" or "drug candidate compound" are synonymous with the term "compound", unless otherwise indicated.

The present invention systematically enhances the efficiency of the pre-formulation process of drug development. In particular, the pre-formulation process is implemented as a process that generates, characterizes and analyzes material compositions. This process can be performed in accordance with the present invention by using illustrative pre-formulation discovery tool system 100 shown in FIG. 1. Pre-formulation system 100 may include computer 110, material handling apparatus 150, material screening device 160, and user interface equipment 180. Pre-formulation system 100 may include multiple material handling apparatuses 150 and multiple material screening devices 160. Only one each of material handling device 150 and material screening device 160, however, is illustrated in FIG. 1 to avoid complicating the drawing. Computer 110 is illustrated to be connected to apparatus 150, device 160, and user interface equipment via communication paths 190. In addition, apparatus 150 and device 160 are also connected by communication path 190.

Computer 110 controls a process that is implemented to perform the pre-formulation process in accordance with the principles of the present invention. Several processes can be implemented in pre-formulation system 100. For example, a process may be used for creating, analyzing and selecting salts for a particular drug product. Other processes may be implemented to generate, characterize and analyze different crystalline structures (e.g., polymorphs) of a compound. Comprehensive processes may involve a process that starts with library design of solvents and ends with identification of a suitable active pharmaceutical ingredient. Such a comprehensive process may, for example, combine a salt selection process with a polymorph process to pre-formulate a desired ingredient. While there are several possible processes that can be developed and used with pre-formulation system 110, the present invention illustrates two such embodiments in FIGS. 2 and 3.

Computer 110 may include electronic circuitry 112 (e.g., hard-drive, processing memory communications buses, etc.) that handles transmission of data to, from, and/or between apparatus 150, device 160, and user interface equipment 180. Electronic circuitry 112 may enable computer 110 to perform processes by controlling, for example, apparatus 150 and device 160. Computer 110 may initiate processes by responding to user input from user interface equipment 180. Computer 110 may also provide information to the user at user interface equipment 180 with respect to data acquired during operation of the process.

Electronic circuitry 112 may store, retrieve, and distribute information from database 114. Database 114 stores information that enables a process to be created and also provides a basis for performing analysis on a material composition. For example, database 114 may store information such as method steps, library designs, results of prior processes, results of processes in progress, publicly available data, library compositions, record sets, polymorph family data, and other suitable pre-formulation data. Database 114 can also store information on material properties of drug candidates and solvents, such as molecular weight, density, boiling point, etc. other stored information can include recipe files, reagents, solvents, compounds, salts, crystals, polymorphs, all known characteristics and properties of such materials and any other information suitable for a pre-formulation process. Database 114 may be updated with new information. The new information may be derived from data obtained from a currently active process or by downloading data via user interface equipment 180.

Computer 110 can run software programs that assist control and operation of a process. Software programs may be used to automate pre-determined portions of the process. For example, software may automate control apparatus 150 in preparing library compositions. An illustrative example of such software is Impressionist™ software sold by Symyx Technology, Inc. of Santa Clara, Calif. Impressionist™ is described in WO 00/67086, published Nov. 9, 2000, which hereby incorporated by reference in its entirety. Other software programs may provide a comprehensive computer generated library that provide the process with a template for preparing various material compositions. A computer generated library advantageously eliminates the time consuming task of manually determining all the permutations and combinations of materials that can be compared under a given set of constraints. An illustrative example of library design software is sold as Library Studio® of Symyx Technologies, Inc. of Santa Clara, Calif. Library Studio® is described in WO 00/23921, published Apr. 27, 2000, which hereby incorporated by reference in its entirety. Persons skilled in the art will appreciate that several software programs may be implemented on computer 110. For example, Epoch™ software sold by Symyx Technologies, Inc. of Santa Clara, Calif., may be used to control and acquire data from instruments such as apparatus 150 and screening device 160. Epoch™ is described in WO 01/79949, published Oct. 25, 2001, which hereby incorporated by reference in its entirety.

Material handling apparatus 150 may provide assemblies that prepare, filter, and/or crystalize salts or polymorphs of a particular drug candidate in accordance with the principles of the present invention. Material handling apparatus 150 may be controlled by computer 110 to automatically mix specific quantities of material (e.g., drug candidates, reagents, etc.) to form a material composition. The materials may be mixed in accordance with library designs produced by computer 110 (e.g., with library design software). When the materials are mixed, they may be analyzed by material screening device 160 to determine various properties such as solubility, crystallinity, melting point temperature, etc.

If desired, material handling apparatus 150 may also be controlled by computer 110 to automate a crystallization process. For example, computer 110 may instruct apparatus 150 to subject its resident material compositions to a precipitation process that causes crystallization. After the crystallization process is complete, the material compositions are tested for at least for crystallinity by screening device 160. It should be noted that above apparatus 150 discussion is not intended to be exhaustive, rather a detailed discussion of material handling apparatus 150 is discussed below in conjunction with FIGS. 13–30.

Automatic control of material handling apparatus 150 enables the present invention to prepare several libraries or members. Moreover, automated control reduces possible errors that can be caused by manual control. In addition, automated control may enable the present invention to prepare relatively small sample sizes (e.g., ranging between nanoliter to milliliter sizes). This advantageously provides high throughput preparation and testing of the material compositions.

Material screening device 160 analyzes materials provided on material handling apparatus 150 and provides data to computer 110 based on that analysis. The analysis of material compositions may also be automated and controlled by computer 110. Material screening device 160 may include a station such as, for example, a solubility testing station, a birefringence station, spectroscopy stations (e.g., Raman, infrared, X-ray), a melting point station, an electromagnetic signal absorption (e.g., UV-Vis absorption) station, partition coefficient (log P) station, hygroscopicity station, and other suitable devices. One or more of these stations may provide data that enables computer 110 to determine the quality and characteristics of a specific material. For example, computer 110 may determine the quality of a salt produced based on the characteristics measured by material screening device 160. In another example, material screening device 160 may provide data on the crystal structure of a material to computer 110. A detailed description of several material screening devices 160 is described below.

User interface equipment 180 enables a user to input commands to computer 180 via input device 182. Input device 182 may be any suitable device such as, for example, a conventional keyboard, a wireless keyboard, a mouse, a touch pad, a trackball, a voice activated console, or any combination of such devices. Input device 182 may enable a user to enter commands to perform drug selection, library building, screening, etc. If desired, input device 182 may enable a user to control material handling apparatus 150 and material screening device 160. Using input device 182, for example, a user may calibrate apparatus 150 prior to use in a process. In another example, a user may manually control material screening device 160 to measure materials formulated in material handling apparatus 150. A user may monitor processes operating on pre-formulation system 100 on display device 184. Display device 184 may be a computer monitor, a television, a flat panel display, a liquid crystal display, a cathode-ray tube (CRT), or any other suitable display device.

Communication paths 190 may be any suitable communications path such as, for example, a cable link, a hard-wired link, a fiber-optic link, an infrared link, a ribbon-wire link, a blue-tooth link, an analog communications link, a digital communications link, or any combination of such links. Communications paths 190 are configured to enable data transfer between computer 110, apparatus 150, device 160, and user interface equipment 180. Communications path 190 may also enable data transfer between apparatus 150 and device 160.

Various processes can be implemented on pre-formulation system 100. Processes may include several steps or stages to achieve a desired result (e.g., salt selection, polymorph testing).

Many neutral pharmaceutically active compounds contain functional groups such as amines or carboxylic acids that can react with acids or bases to form salts. In general, salts tend to be more water soluble and have higher melting points than the corresponding neutral compounds. Salt selection for a drug candidate is not necessary if the neutral compound has suitable properties. However, salts of drug candidates often have desirable properties that are useful for formulation or bioavailability. Desirable properties of a salt compared to a neutral compound may include the ability of the salt to form crystals that are produced more easily or cheaply, crystals that are more stable, more filterable, less hygroscopic, more soluble in water, or have a higher melting point or a more favorable log P for administration. For instance, for pharmaceutical compounds listed in the Physicians' Desk Reference (2000) that are salts, more than 50% of the neutral compounds of the salts are insoluble in water (they have a solubility of less than 1 mg/mL). In contrast, less than 20% of the corresponding salts, i.e., the listed pharmaceutical compounds, are similarly insoluble. Further, more than 30% of neutral bases listed in the Physicians' Desk Reference (2000) have a melting point below 120° C., while under 10% of their corresponding salts have a melting point below 120° C. Having a higher melting point is often desirable for easier formulation.

The selection of a salt for a drug candidate of interest is largely limited to the number of experiments that can reasonably be performed in the time allotted. Since the counter-ion affects the physical property of the drug candidate salt, different salts of the same drug candidate will crystallize under different conditions and will have different physical properties. Thus, it is necessary to perform a number of different recrystallization experiments to generate crystals for different drug candidate salts. By having a number of different drug candidate salts, one can identify those salts that are likely to be the most useful for drug formulation and administration.

Table 1, below, lists common anions for salts and Table 2, below, lists common cations for salts.

TABLE 1

| Anion | Count | % of Total | Cumulative % of Total | Cumulative %: No. of Compds |
|---|---|---|---|---|
| Cl | 156 | 60.9 | 60.9 | |
| $SO_4$ | 26 | 10.2 | 71.1 | 71%: 2 |
| Mesylate | 11 | 4.3 | 75.4 | |
| Br | 10 | 3.9 | 79.3 | 79%: 4 |
| Tartrate | 9 | 3.5 | 82.8 | |
| Citrate | 8 | 3.1 | 85.9 | |
| Maleate | 7 | 2.7 | 88.7 | |
| Acetate | 4 | 1.6 | 90.2 | 90%: 8 |
| Besylate | 4 | 1.6 | 91.8 | |
| NO3 | 3 | 1.2 | 93.0 | |
| PO4 | 3 | 1.2 | 94.1 | |
| Fumerate | 3 | 1.2 | 95.3 | 95%: 12 |
| Succinate | 3 | 1.2 | 96.5 | |
| Benzoate | 1 | 0.4 | 96.9 | |
| Gluconate | 1 | 0.4 | 97.3 | |
| Glucoronate | 1 | 0.4 | 97.7 | |
| Lactate | 1 | 0.4 | 98.0 | |
| methylsulfate | 1 | 0.4 | 98.4 | |
| Oleate | 1 | 0.4 | 98.8 | |
| Napsylate | 1 | 0.4 | 99.2 | 99%: 20 |
| Tannate | 1 | 0.4 | 99.6 | |
| Xinafoate | 1 | 0.4 | 100.0 | |
| Total | 256 | | 100.0 | |

TABLE 2

| Cation | Count | % of Total | Cumulative % of Total | Cumulative %: No. of Compds |
|---|---|---|---|---|
| Sodium | 57 | 76.0 | 76.0 | |
| Potassium | 5 | 6.7 | 82.7 | 83: 2 |
| Calcium | 4 | 5.3 | 88.0 | |
| Magnesium | 1 | 1.3 | 89.3 | 89: 4 |
| Ammonium | 1 | 1.3 | 90.7 | |
| Tromethamine | 1 | 1.3 | 92.0 | |
| t-Butylamine | 1 | 1.3 | 93.3 | |
| Piperazine | 1 | 1.3 | 94.7 | 95: 8 |
| Silver | 1 | 1.3 | 96.0 | |
| Zinc | 1 | 1.3 | 97.3 | |
| Lithium | 1 | 1.3 | 98.7 | |
| Gold | 1 | 1.3 | 100.0 | 100: 12 |
| Total | 75 | | | |

In Tables 1 and 2, the count number and percent of total indicate the number of drugs and the percentage of the total that a particular anion or cation was used as part of an active pharmaceutical ingredient, based on a survey of compounds in use from the Physicians' Desk Reference (2000). The cumulative percent of the ions is shown in the fourth column. Thus, as shown in Table 1, the two most common anions of active ingredients are chlorides and sulfates, accounting for over 70% of the drugs on the market as of the printing of the 2000 Physician's Desk Reference (PDR). This is highlighted further in the fifth column, which shows that the top two anions account for 71% of drugs on the market at that time, the top four account for 79%, the top eight 90%, and the top twelve 95%. As shown in Table 2, the two most common cations of API's are sodium and potassium, accounting for over 80% of the drugs on the market at the time. For cations, the top two cations account for 83% of drugs on the market at the time, the top four account for 89%, and the top eight account for 95%. With the combinatorial or high throughput techniques of this invention, both anionic and cationic salts can be screened, such that for most drug candidates, most if not all commonly used pharmaceutically useful salts can be tested.

In some embodiments of this invention, at least two, four or six different salt forms of one or more drug candidates are produced and screened for desired properties. In other embodiments, at least eight, more specifically at least 10, at least 12, at least 16, at least 20, or at least 24 different salt forms of one or more drug candidates are produced and screened for desired properties. In one embodiment, salt reactants comprising the two, four, six or eight most common anions or cations, as shown in Tables 1 and 2, are used for screening. In another embodiment, high throughput screening is performed using salt reactants for both anions and cations. Thus, salt reactants for the two, four, six or eight most common anions and cations are used.

The number of solvents that may be used for salt selection may be any number desired. In one embodiment, the number of solvents is two four, six, eight, 12, 16 or more. The screening of salt and solvent combinations (discussed below) can be at the rate of at least eight at a time, at least 12 at a time, at least 24 at a time, at least 36 at a time, at least 48 at a time, or at least 96 at a time. Depending on how the library is designed, there can be different salts in a plurality of wells; alternatively, there can be different solvents in a plurality of wells, etc.

In one embodiment, a different salt is present in each row of a substrate, wherein a row comprises a number of wells. The substrate may be a microtiter plate or another substrate on which wells may be formed, e.g., using the salt reaction apparatus described herein. Each column, which also comprises a number of wells and is perpendicular to the row containing the salt, contains a different solvent. See, e.g., FIG. 15, which shows an example of a microtiter format containing rows and columns. The library is not limited in this manner. This rate of testing allows for rapid discovery of the appropriate salt(s) for further investigation.

Figure 2A:
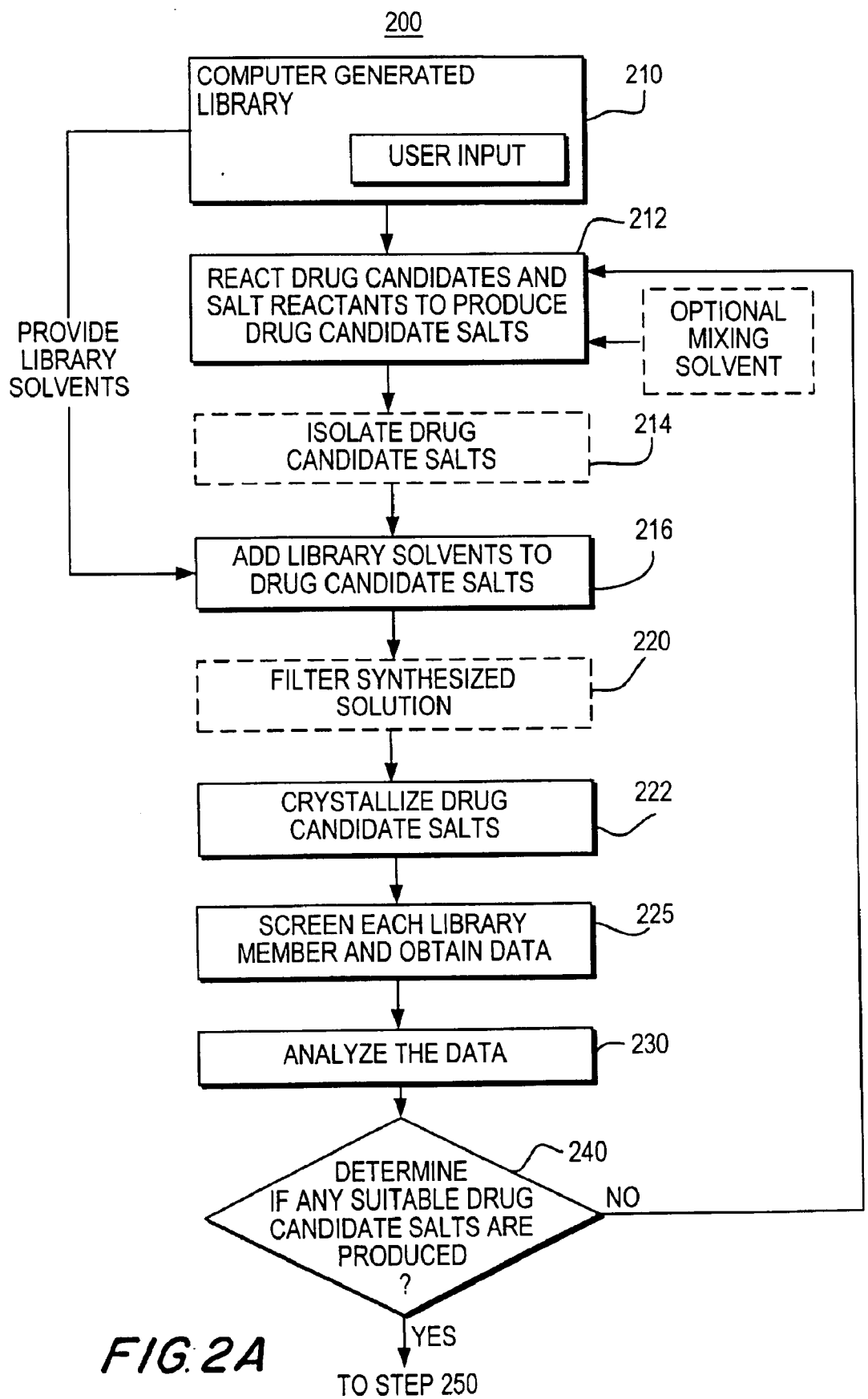
FIGS. 2A and 2B show an illustrative flow diagram of salt selection process that is in accordance with the principles of the present invention.
Figure 2B:
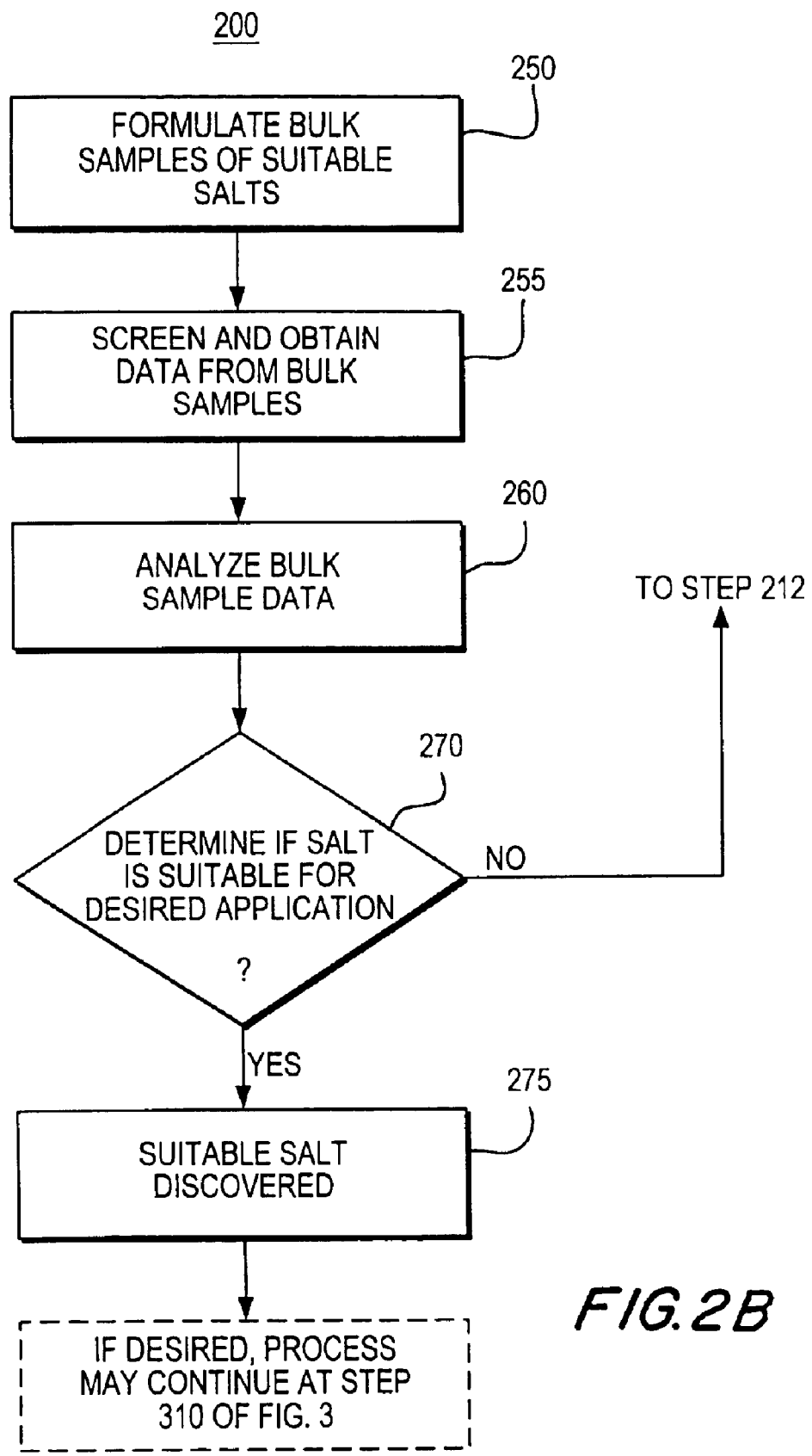

FIGS. 2A and 2B show an illustrative flow diagram of salt selection process 200 which is in accordance with the principles of the present invention. Generally, process 200 dispenses a drug candidate compound in a receptacle in an array format (e.g., an 8 by 12 array) and subjects each drug candidate to various combinations of one or more salt reactants and, optionally, a solvent. In one embodiment, each receptacle contains at least one drug candidate, a stoichiometric amount of at least one salt reactant, and, optionally, a solvent. In a preferred embodiment, each receptacle contains one drug candidate, a stoichiometric amount of one salt reactant and a solvent. Depending on the interaction of mixture of the drug candidate, salt reactant and solvent, a salt may form and precipitate or crystallize. Salts may then be screened and analyzed to determine whether the properties and characteristics are suitable for a particular drug application.

Processing selected drug candidates or salts for discovery and characterization required at least two, but preferably at least three steps that are performed in a combinatorial or high throughput mode. One required step is dissolution of drug candidates or salts to form a solution. Another required step is crystallization (e.g., by evaporation, cooling or precipitation with an anti-solvent) of drug candidates or salts from the solution. An optional processing step prior to crystallization may include separating any remaining solids from the solution by filtration or centrifugation. This separation or filtering step may be performed to eliminate nucleation sites in the solvent provided to the crystallization step. Process 200 includes the preparation, crystallization, filtration, and other steps that are performed for salt selection.

Prior to preparing solutions comprising the drug candidate and the salt reactant, a user may interact with a computer (e.g., computer 110 of FIG. 1) to generate a model library. At step 210, one or more computer generated libraries are generated to enable process 200 to prepare substantially every possible combination of materials that can be mixed within a given set of constraints. Thus, when these mixtures are prepared and then crystallized, the present invention can determine which mixture provides the best salt. Each individual mixture is commonly referred to as a library member or member. The computer generated model library may be generated using a number of parameters (also called constraints) that typically include materials such as drug candidates, salt reactants, solvents, environmental conditions, reaction parameters, etc. Parameters may be selected by a user or a software program. Preferably, a user selects one or more drug candidates for modeling in the library and other parameters such as library size (e.g., a 96 well array). A library member usually comprises a drug candidate, a salt reactant and a solvent. The solvent, referred to as a library solvent in method 200, is used for crystallizing the salt produced by the reaction of the salt reactant and the drug candidate. Computer generated library designs are preferably modeled by software programs running on computer 110 (shown in FIG. 1). The computer generated library may be based on user input and information available from database 114. The computer generated library is described in more detail in conjunction with FIGS. 4 and 5.

Persons skilled in the art will appreciate that computer need not be used to prepare a library. A person could manually prepare a library using any suitable method.

At step 212, a drug candidate and a salt reactant are mixed together. An optional mixing solvent, which may be different or the same as the library solvent, may be added to the salt reactant and drug candidate. The drug candidates, salt reactants and optional mixing solvents are reacted together to produce drug candidate salts. At optional step 214, after the drug candidate salts have been produced, the drug candidate salts are isolated. At step 216, the library solvents provided at step 210 are added to the drug candidate salts to produce the library members.

In a preferred embodiment, the drug candidate mixture described at step 212 is prepared in a reactor assembly. Reactor assemblies are typically constructed in microtiter format (e.g., an 8×12 96-well plate). Microtiter format is particular useful for performing high throughput reaction of materials. However, any other format may be used (e.g., a 384 well plate). In addition, this enables process 200 to construct a library in reactor assembly 1300 in accordance with the computer generated library provided at step 210.

Figure 23:
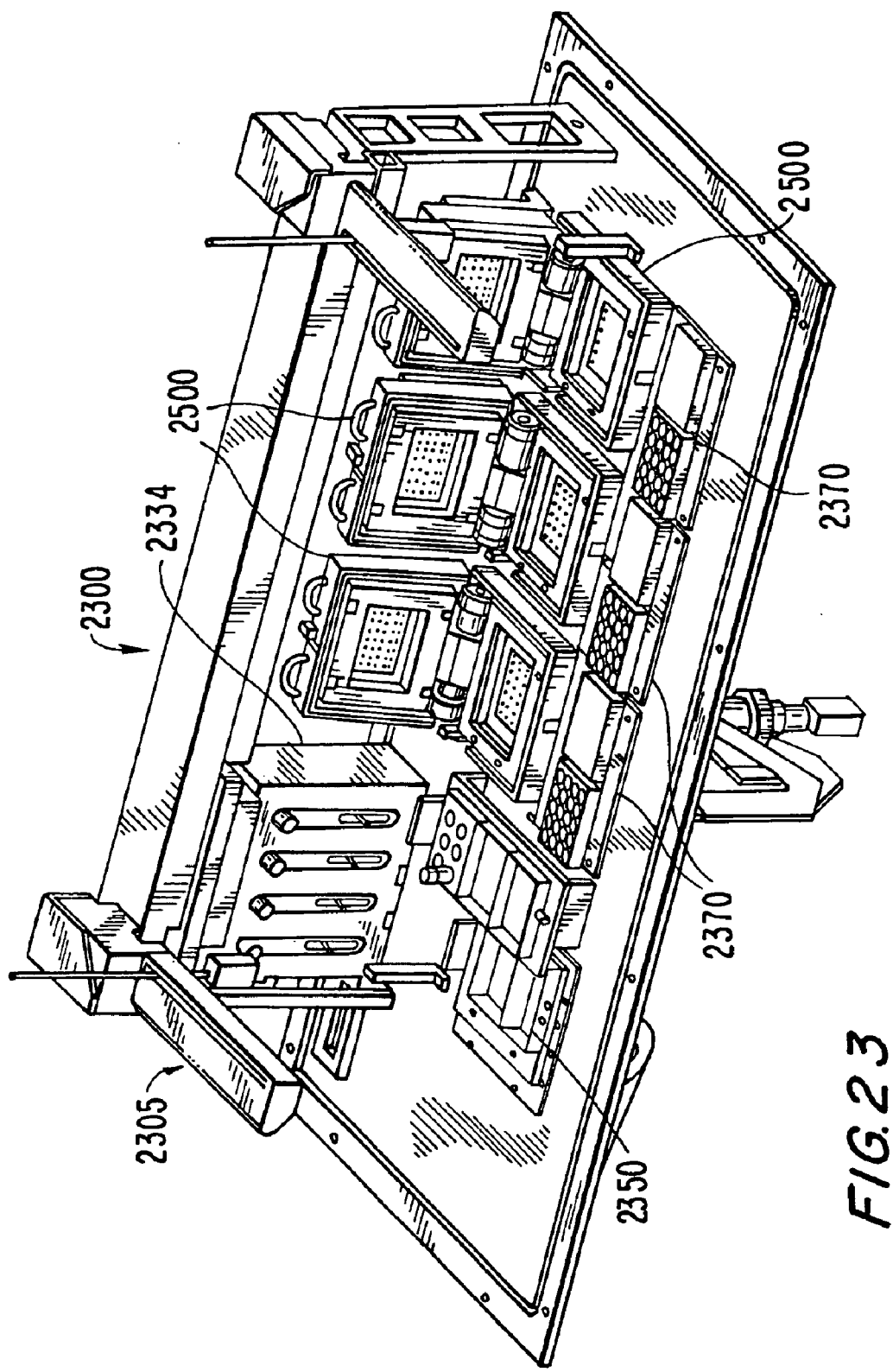
FIG. 23 shows a process platform that has a liquid handling robot that can dispense and aspirate fluid from assemblies positioned on the platform in accordance with the principles of the present invention.

At step 212, drug candidates may be mixed with salt reactants according to the computer generated library at step 210. The mixture may optionally comprise one or more mixing solvents to provide a salt solution. The drug candidate is typically dispensed (into reaction containers) as a solution or a slurry, but it can be also be dispensed as solid. A liquid dispensing device is illustrated in FIG. 23. A solid dispensing device (not shown), for example, is sold as Powdernium by AutoDose of Geneva, Switzerland. Assuming that the drug candidate is in a solution or slurry, the solvent may or may not be driven off across the plate in parallel (such as by blowing nitrogen over the library or with a solvent evaporator, e.g., Genevac HT-8 (Genevac Inc, Valley Cottage, N.Y. 10989) under reduced pressure or vacuum. If the drug candidate is dispensed in the reaction solvent, then solvent removal is unnecessary.

After dispensing of the drug candidate, the chosen salt reactant (e.g., an acid or base in solution, slurry or solid format) is dispensed into the wells of the array. For anion salts, the corresponding acid is used. For example, hydrochloric acid, sulfuric acid, mesylic acid and bromic acid may be used for chloride, sulfate, mesylate and bromate salts of compounds. For cationic salts, one may use the corresponding hydroxide or other base. For instance sodium hydroxide and potassium hydroxide may be used for sodium and potassium salts. Magnesium and calcium salts of drug candidates may be formed by using magnesium or calcium acetate, oxide or carbonate. Amine salts may be formed by mixing the amine of choice itself with the drug candidate. In one embodiment, the salt reactant is dispensed automatically into the wells of the array, as discussed in more detail below. In another embodiment, the salt reactant is dispensed manually into the wells of the array.

The salt solution is subjected to various conditions to allow the drug candidate to react with the salt reactant under the conditions imposed. Common reaction conditions are a temperature of about room temperature or higher with shaking in sealed vials. The temperature may be approximately 20° C., 30° C., 40° C., 50° C., 60° C., 70° C., 80° C. or higher. In one embodiment, the temperature is raised to approximately 70° C. to allow the drug candidate to react with the acid or base. Depending on the drug candidate and the salt reactant, a reaction between the drug candidate and the reaction solvents may or may not occur.

Individual vials or wells may contain magnetic stirring fleas that are tumbled (e.g., rotated) by a magnetic field or a rotating magnet. The rotating stirring fleas promote mixing of the materials contained within the vials or wells. A detailed explanation of a device that provides magnetic stirring is described in U.S. Pat. No. 6,176,609, which is hereby incorporated by reference in its entirety.

At optional step 214, after each library member is prepared, any remaining salt reactants and optional solvents are removed from the reaction mixture. This may be done by any method known in the art, including, e.g., methods used for crystallization, such as evaporation, cooling or addition of an anti-solvent.

At step 216, one or more library solvents are added to each well in accordance with the computer generated library and the drug candidate is dissolved in the solvent.

At optional step 220, after each library member is prepared, an aliquot of the salt solution is taken from each reaction container and filtered by a filtration assembly. Each salt solution is filtered so that a "seedless" salt solution is used for crystallization at step 222. FIGS. 16–20 illustrate various filtration apparatuses that provide filtration in accordance with the principles of the present invention.

If seeding is desired, a seed may be added separately, so that seeded recrystallization is controlled.

At step 222, the filtered salt solutions are crystallized. Salt crystallization can occur by 1) cooling the solution, 2) precipitating the solution by adding an anti-solvent that causes precipitation, 3) evaporating the solution, or 4) slurrying the solution. If salt crystallization or precipitation occurs on a multi-well plate or a substrate, such as the universal substrate described herein, the plate or substrate may be screened by various identifying and characterization devices. If desired, characterization can be performed while recrystallization is occurring. The salt reactants and solvents that may be used to crystallize or precipitate the salts are described below in solvent selection section.

Each library member is screened to determine if a salt has formed. Screening is performed at step 225 and can be implemented using material screening device 160 (shown in FIG. 1). Screening at step 225 may be performed primarily as a high-throughput screen that quickly characterizes each library member. Data obtained during the screening may be provided to a computer (e.g., computer 110). For example, screening at step 225 may obtain a sufficient quantity of data on each library member such that process 200 can be used to quickly analyze the salt. The apparatus and methods described herein provide several screening methods and devices that can determine birefringence, log P, crystallinity, solubility, and melting point of each library member in situ.

At step 230, process 200 can perform a quick preliminary assessment on the suitability of each salt before additional time consuming tests are performed. Analysis can include user-defined selection by selecting which library members should be explored further. Salt selection can also be performed, for example, by computer. A computer can run software programs that analyze the data. For example, results of the screening can provide information regarding whether the salt formed a solid, whether the solid was amorphous or crystalline, and information regarding the solubility, log P and melting point of the crystal.

At step 240, process 200 determines if a salt should be selected for further testing or if it should be discarded. If none of the salts produced in the library are suitable for additional testing (e.g., screening), the process returns to step 212 so that new library compositions can be prepared. The data obtained from these salts, however, is stored on a database and used for future analysis. Preferably, process 200 continues to prepare library compositions based on computer generated library models generated in step 210. However, if step 240 determines that there is at least one suitable salt, process continues to step 250.

At step 250 in FIG. 2B, the salt selected in step 240 is resynthesized in bulk format. This step is only necessary if sufficient quantities of the salt selected in step 240 were not produced. In step 250, multiple samples of the same material composition are deposited in a different reactor assembly. If desired, additional solvents may be applied to the existing library compositions to obtain, for example, additional salt characteristics. The application of new materials may be based on a library modeled at computer 110 (FIG. 1). Then the newly-formulated library compositions are crystallized to form salt.

At step 255, the salts are screened again to obtain property and characteristics data, if more data are required. This screening can be used to provide a more in-depth characterization of the salts than screening step 225. Step 255 obtains data that enables process 200 to perform a secondary analysis (shown at step 260). At step 260, a substantial analysis may be performed using the data provided by step 255. At step 270, process 200 determines if the salt should be selected for further testing. If the salt is not selected, process 200 may return to step 212 (FIG. 2A). If the salt is selected, then process 200 has discovered a salt that is suitable for use in another application. Persons skilled in the art will appreciate that one or more salt forms may be selected by process 200 and it will also be appreciated that process 200 may not produce any salts that are selected based on the parameters set in step 210.

Figure 3:
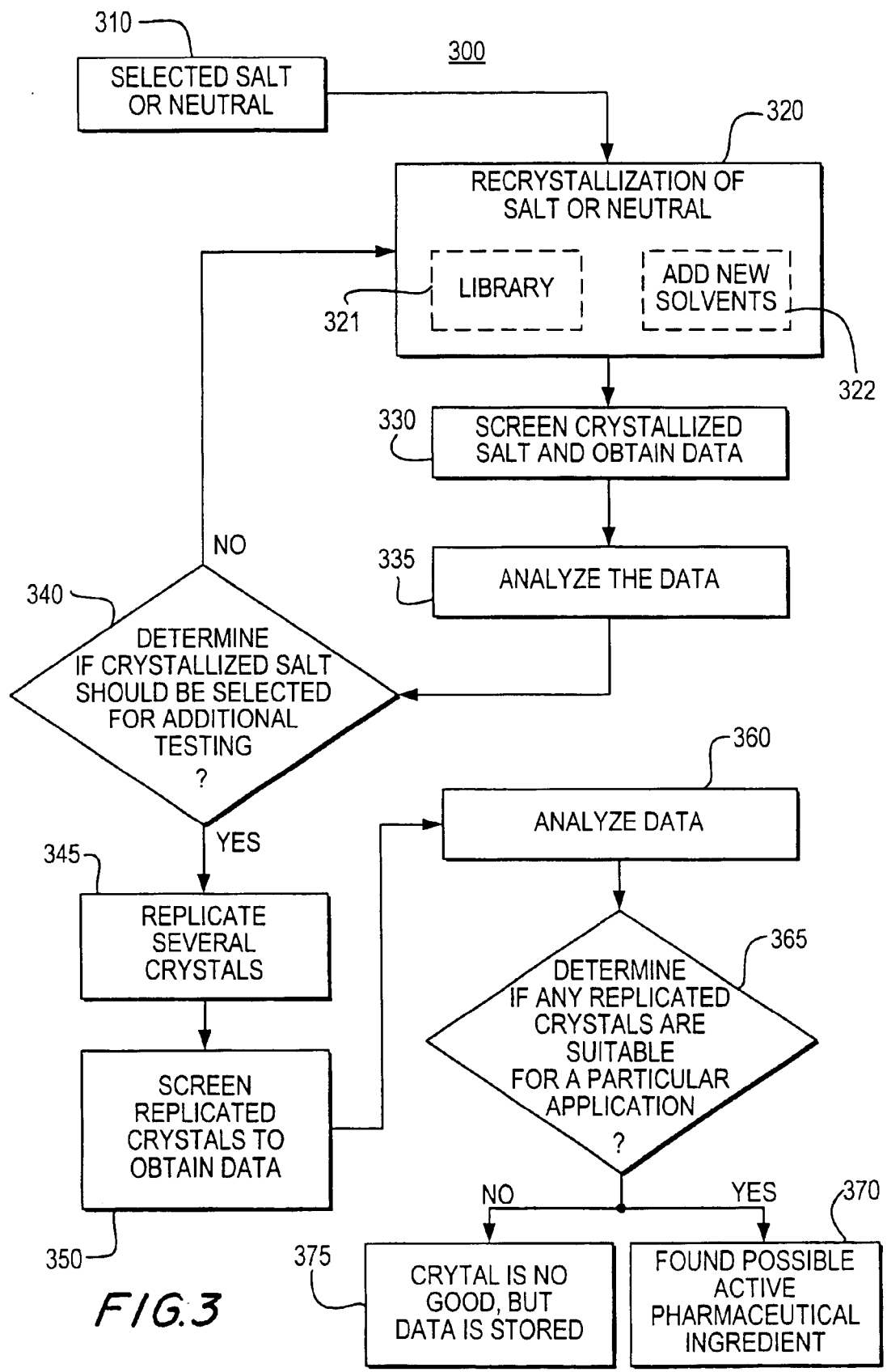
FIG. 3 shows an illustrative flow diagram of polymorph testing that is in accordance with the principles of the present invention.

If desired, after a salt is selected process 200 may proceed to step 310 of FIG. 3. As described below, FIG. 3 describes polymorph generation and characterization based on the selected salt.

Process 200 may be implemented on pre-formulation system 100 to select salts that are suitable for drug development. Process 200 may be used as precursor to another process that performs test on one or more selected salts to determine various potential polymorphs of the salt's crystalline structure. Persons skilled in the art will appreciate that steps shown in FIG. 2 are merely exemplary and that additional steps may be added and some steps may be omitted or modified. For example, a step can be added that causes process 200 to prepare and test every library member provided by the computer generated library in step 210 even if one or more suitable salts have been discovered. Further, daughter libraries may be formed to alter the conditions under which salts may be formed (e.g., temperature or temperature ramp rate) or to provide identical salts for destructive analyses (e.g., melting point screens).

FIG. 3 shows an illustrative flow diagram of polymorph discovery process 300 which is in accordance with the principles of the present invention. Process 300 may be implemented on pre-formulation system 100 independent of other processes or it may be merged with processes such as process 200 of FIGS. 2A and 2B.

Process 300 recrystallizes one or more drug candidates or salts (i.e., subjecting them to different conditions to generate as many polymorphs as possible, preferably substantially every polymorph, for a particular drug candidate or salt thereof) and screens each of the polymorphs in a high-throughput capacity. This enables process 300 to quickly characterize and determine those recrystallization conditions that are best for developing a desired drug ingredient that possesses a suitable crystalline structure. As used herein, recrystallization and crystallization conditions refer to those conditions that affect recrystallization. These conditions include, e.g., temperature, seeding (if present), solvent(s), etc.

Process 300 begins at step 310. At step 310, process 300 is provided with one or more drug candidate salts (or neutral compounds) for polymorph testing. The drug candidates can be preselected, for example, by a user via user interface equipment 180 (shown in FIG. 1). Drug candidates may also be provided by salts selected in process 200 of FIGS. 2A and 2B. Alternatively, step 310 may be provided with one or more drug candidates that can be used for polymorph testing.

Once a drug candidate is provided at step 310, the drug candidate may undergo recrystallization at step 320. If desired, recrystallization may involve several steps to form crystals from a particular drug candidate. For example, after a drug candidate has been selected, it may be mixed with solvents 322 in a reaction assembly (e.g., reaction assembly 1300 of FIG. 13 or reaction assembly 1500 of FIG. 15). The drug candidate and solvents may be dispensed into a reaction assembly using a liquid dispensing assembly as described for salt selection process 200. The solvents may be mixed in accordance with a computer generated library 321 to provide as many different crystallization mixtures for a particular set of constraints. Solvent selection is described further below.

The number of solvents that may be used for polymorph generation and characterization may be any number desired. In one embodiment, the number of solvents is two, four, six, eight, 12, 16, 24, 36, 48, 96 or more. The number of solvents that may be used for polymorph generation and characterization for a single assay can be at the rate of at least eight to ten at a time, at least 12 to 14 at a time, at least 24 at a time, at least 36 at a time, at least 48 at a time, or at least 96 at a time. The term solvent in this respect means both a single solvent (e.g., heptane or water) as well as combinations of solvents (e.g., heptane mixed with water), as described herein.

In one embodiment of this invention, at least one drug candidate is used in a process of generating and characterizing polymorphs. In other embodiments at least two, three or four drug candidates are used to generate and characterize polymorphs.

If further desired, recrystallization may include filtering the mixtures to provide "seedless" or "pure" solutions for crystallization. A filtering step is performed formulation and prior to crystallization. Crystallizing filtered solutions eliminates nucleation sites that can bias formation of crystals during the crystallization step. Filtering may be accomplished using filtration assembly 1600 of FIG. 16.

Figure 21:
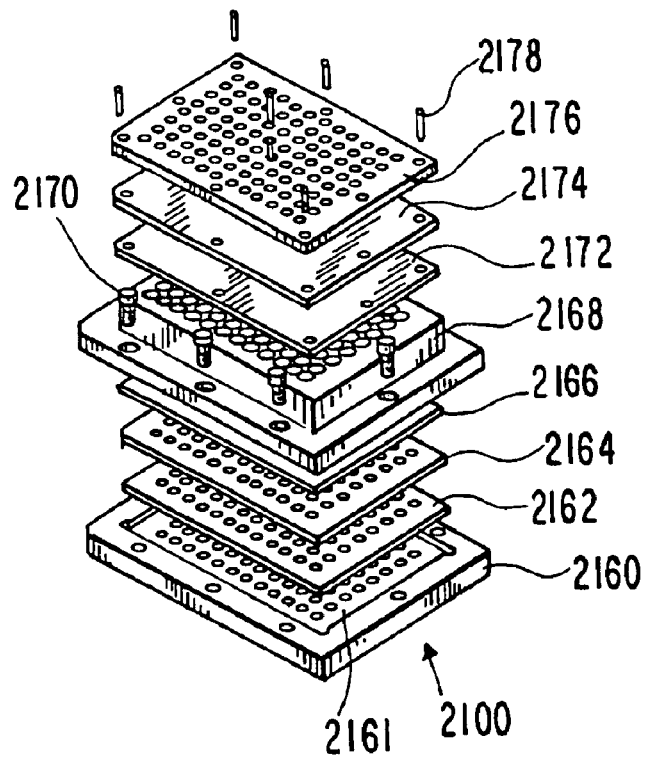
FIG. 21 illustrates an exploded view of a crystallization assembly in accordance with the principles of the present invention.
Figure 22:
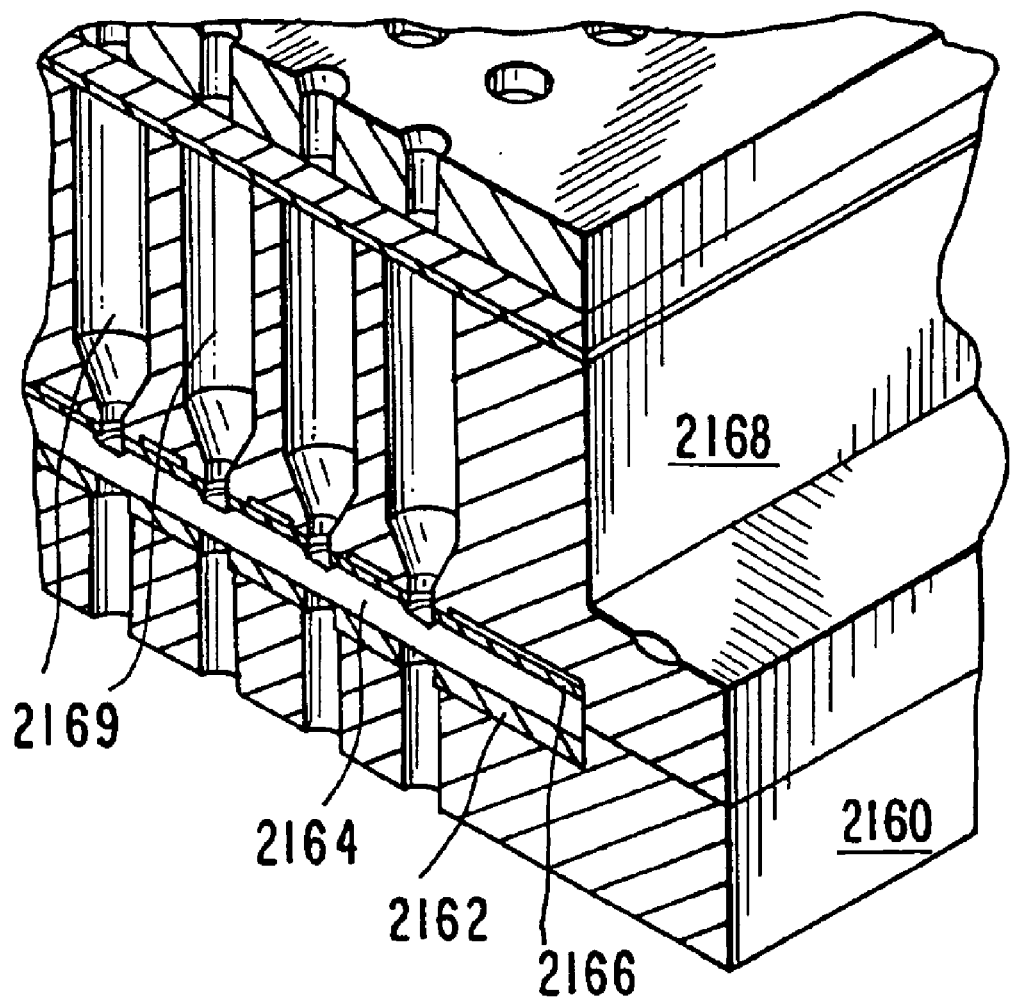
FIG. 22 illustrates a partial cross-sectional view of crystallization assembly of FIG. 21 that is in accordance with the principles of the present invention.

Various recrystallization conditions (e.g., temperature, pressure, time, etc.) may be varied to provide various crystal formation. FIGS. 21 and 22 illustrate, for example, an apparatus that can be used to crystallize the mixtures. One advantage of this apparatus (e.g., crystallization assembly 2100 of FIG. 21) is that crystals may grow, form or re-salt on a removable substrate. This substrate may be provided to one or more screening devices such that crystals are scanned for their properties and characteristics at step 330.

To perform crystallization or recrystallization under a variety of crystallization conditions, daughter libraries may be created from drug candidates, mixtures, or salts thereof. A daughter library is created by taking one or more aliquots from one or more members in a parent library contained within a reactor assembly. A parent library may include mixtures that are prepared at the beginning of recrystallization step 320. An aliquot is a definite fraction of a whole.

To perform daughtering, a pipette, operated either manually or automatically (e.g., robotically), draws a portion of a member from the parent library and dispenses that aliquot into another container (e.g., crystallization assembly) to provide a daughter library member. A limited number of members of the parent library may be daughtered or all the members may be daughtered at least once to create a daughter library. Thus, a daughter library may be smaller than the parent library in terms of either mass, volume or moles and/or in terms of the number of members. Daughtering is performed, for example, to allow for multiple experiments on identical mixtures, solutions, or samples to avoid having to recreate the parent library. There is known equipment that can perform daughtering, such as hand pipetters, hand-multichannel pipetters, or robots (such as Matrix or CyberLab or Hydra robots). Any number of daughter libraries may be produced, provided that the original library is of sufficient volume. In one embodiment, at least one, two, four, eight or twelve daughter libraries are produced.

After the mixtures from the parent library and daughter libraries are crystallized, each library member is screened. Step 330 provides primary screening that provides data to step 335, which analyzes the data to determine if any polymorphs have formed.

The crystals may be screened for any physical property that would help characterize and/or identify a polymorph. The crystals may be screened for birefringence, melting point, solubility, hygroscopicity, IR pattern, Near IR pattern or Raman pattern, crystal morphology, X-ray powder diffraction pattern or any other suitable screening method to determine if crystals (or polymorphs) have formed. In general, at least two properties are screened. In one embodiment, Raman pattern, X-ray diffraction pattern, melting point, birefringence and hygroscopicity screens are performed to adequately characterize the crystalline structures.

At step 340, process 300 determines whether a polymorph should be selected being produced in bulk for further testing, if sufficient quantities of the drug candidate have not been produced during process 300. If the polymorph is unsuitable, the process may revert back to step 320 such that the same or different drug candidates can undergo recrystallization. If the polymorph is selected, process 300 may prepare several of the same crystals at step 345 so that they can be screened and characterized at step 350.

At step 350, the screening is more detailed than the screening performed at step 330. The crystals may be screened for at least two properties, three properties, four properties or five properties to identify and characterize polymorphs, wherein the properties are determined by, e.g., birefringence, melting point, solubility, hygroscopicity, IR pattern, Near IR pattern, Raman pattern, crystal morphology or X-ray powder diffraction pattern or, if sufficient amounts have been produced, single crystal X-ray diffraction, thermogravimetric analysis, nuclear magnetic resonance or differential scanning calorimetry. In one embodiment, the crystals are screened for at least birefringence, melting point, solubility, Raman pattern and X-ray powder diffraction pattern. Preferred embodiments include Raman and/or X-ray diffraction spectroscopy. The process may be performed using a solubility testing station, a birefringence station, spectroscopy stations (e.g., Raman, infrared, X-ray), a melting point station, an electromagnetic signal absorption (e.g., UV-Vis absorption) station, partition coefficient (log P) station, using the apparatus described herein.

The data obtained in step 350 may provide a substantial quantity of information to enable process 300 to analyze the polymorphs or crystalline structures (step 360). At step 365, process 300 may determine if the polymorph (e.g., neutral drug candidate compound or salt thereof) is suitable for use as an active pharmaceutical ingredient (step 370). If the polymorph is not suitable, then that particular drug candidate is not used, at least for the drug application prescribed for process 300 (step 375). The data obtained from analysis, however, may be stored for future reference.

As illustrated in FIGS. 2A, 2B, and 3, processes use computer generated libraries as a template for preparing library members. For example, libraries containing various combinations of drug candidates, salts, crystals, and other pre-formulation materials may be generated prior to library preparation. FIG. 4 shows an illustrative library 400 that can be generated in accordance with the principles of the present invention. Library 400 can include any suitable number of library elements 410. Preferably the number of library elements modeled in each library 400 is the same as the number of library members 410 that can be prepared on hardware (e.g., a substrate). Any number of rows and columns of library members 410 can be created, thus providing flexibility in library generation. This is illustrated by the variable "N", which indicates that any suitable number of rows and columns can be designed in library 400. The row may, for example be Industry typically uses a substrate that has 96 wells or vials for formulating or mixing various materials. Therefore, if library 400 is modeled to have, for example, eight rows and twelve columns (a typical microtiter plate), library elements 410 may be readily implemented in practice. Likewise, if a 384 well substrate is being used, then library 400 may be modeled to have, for example, 16 rows and 24 columns.

Regardless of the size of library 400, each library element 410 includes at least two materials. The materials in each library element 410 can differ by drug candidates, different known crystal structures of drug candidates, solvents and salt reactants. FIG. 4 shows a few example materials 420 that can be used to model library elements 410. Based on materials 420 and other factors, a computer (e.g., computer 110 of FIG. 1) can model substantially every possible combination of library elements that can be practically constructed. For example, library element 411 illustrates one such possible combination that includes a drug candidate, the salt reactant tartaric acid, and heptane. Thus, generating libraries provides the present invention with a foundation to prepare and test several different material compositions. This facilitates salt selection and provides a basis for discovering polymorphs for a particular drug candidate.

A large number of solvents are known that can be used in recrystallization, either for salt selection and/or for polymorph generation. Table 3 (shown in FIGS. 29A, 29B and 29C) lists a number of exemplary solvents along with some of their physical properties. Given the large number of solvents that may be used, it is advantageous to cluster solvents into groups based upon certain shared physical properties or other shared characteristics of the solvents and then pick at least one solvent from each group to test in recrystallization. This process ensures that a wide variety of different types of solvents will be used for recrystallization, which is advantageous for identifying polymorphs or desirable crystals of drug candidate salts.

Table 3 shows solvents along with their chemical class, a reference number (#) assigned to different classes of solvents (for statistical sort purposes), molecular weight (MW), density (n), molar volume ($V_m$) melting point (MP) (in ° C.), boiling point (BP) (in ° C.), enthalpy of evaporation ($\Delta H_{vap}$), Hildebrand solubility parameter ($\delta$), dipole moment ($\mu$), log solubility in water (log S), partition coefficient (log P), viscosity, index of refraction, pKa (in water and dimethylsulfoxide (DMSO)), dielectric constant ($\epsilon$) and ionization potential (IE) and $pK_{a+}$. Other parameters known to those in the art could be included, such as, without limitation, the cost in US dollars per kilogram, cost of disposal or storage, degree of toxicity or environmental safety. The description of the solvents and physical properties provided herein does not limit the type of solvent or the physical properties of the solvent that may be used in the salt selection and polymorph workflows.

One or more of the physical properties of the solvents in a solvent library may be used to cluster solvents into groups. The solvents in a particular group will have similar physical properties for the one or more properties that has been chosen as a criteria. The physical properties of the solvents may be one or more of those listed in Table 3 or may be other physical properties known in the art. One may use from one to n properties to cluster the solvents into groups, wherein n is the total number of physical properties that have been provided for a library of solvents. Each solvent may be independently sorted into a group with other solvents that have the same defined characteristics for all of the selected physical properties. One may use any number of properties to cluster solvents, including from four to 20, four to 16 or six to eight properties to cluster the solvents. In one embodiment, the class of the solvent (e.g., whether it is an alcohol, ketone, etc.) is not employed as one of the physical properties used in grouping the solvents.

For any particular physical property, the selection criteria may be defined to provide for two or more different subsets. In one embodiment, the selection criteria for single physical property solvents may provide for two, four, six, eight or twelve subsets. For example, one may provide four definitions for dividing the solvents based upon one physical property (e.g., the solvent's density) and provide two definitions for dividing the solvents based upon another physical property (e.g., the solvent's dipole moment). The solvents would then be clustered into eight groups based upon the definitions of these two physical properties.

In a preferred embodiment, the physical properties of a large number of solvents are kept in a database. During library design for polymorph generation or salt selection, a user can define both the specific physical properties and the selection criteria for these physical properties in order to cluster the solvents into groups based upon the particular physical properties chosen and the selection criteria for these physical properties.

One may design solvent groups to form from two groups up to n groups, wherein n is the total number of solvents in the designated solvent library. In one embodiment, the number of solvent groups is four to 96 groups. In another embodiment, the number of solvent groups is six to 64, eight to 48 groups, ten to 40 groups or 12 to 24 groups. In another embodiment, the number of solvent groups is eight to 24 groups, 16 to 24 groups, 20 to 40 groups or eight to 12 groups. In general, a smaller number of solvent groups are used for the salt selection workflow as compared to the polymorph characterization workflow. For salt selection, the number of solvent groups is generally in the range of 16 to 24 groups, while for polymorph identification and characterization, the number of solvent groups is generally around 20 to 40.

In one embodiment, in order to provide diversity of the types of solvents that are used for salt selection or polymorph generation, a solvent library may be clustered into groups of solvents having particular similar physical properties or characteristics and at least one solvent from each group is used in the salt selection or polymorph generation. In another embodiment, a number of solvents from a single group may be selected and used in salt selection or in polymorph generation. This may be particularly useful at later stages in polymorph characterization, to identify potential facile, stable or commercial methods for generating a particular polymorph for an active pharmaceutical ingredient, or to prepare focused solvent libraries.

Solvent group design may be performed by any method known in the art, including manual design or computer design. Commercially available computer programs can be used, including JMP™, available from SAS Institute, Inc., Cary, N.C.

In general, solvents are chosen to have a boiling point higher than the temperature at which the crystallization will be run. Other physical properties that are preferred are those in which non-toxic solvents are used. In another embodiment, one or more solvents such as ethanol, water, cyclohexane, propanol, acetonitrile, dioxane, methyl ethyl ketone, ethyl acetate, isopropyl acetate, propyl acetate or toluene are used as a solvent in the methods described herein.

In one embodiment of a salt selection array, one axis of the array (e.g., the rows of a microtiter plate or other substrate) contains a constant amount of the drug candidate of interest mixed with a number of different salt reactants, wherein each row of the array contains a different salt reactant. In general, the drug candidate is mixed with one equivalent of the salt reactant (e.g., an acid or base). However, in another embodiment, the drug candidate may be mixed with 0.5, two, 1.5, three or four equivalents of the salt reactant.

The opposite axis of the array (e.g., the columns of the microtiter plate) contains a number of different solvents, wherein each column of the array contains a different solvent. In a preferred embodiment, the solvents have been clustered as described herein. Thus, each well of the array contains a different combination of salt reactant and solvent.

The salt reactant and drug candidate may be subjected to conditions in which a salt may form prior to addition of the solvent, e.g., by heating, stirring, shaking or any combination thereof. An array of solvents may then be added and the presence of crystals or precipitates of drug candidate salts may be determined. Alternatively, the drug candidate, salt reactant and solvent may be mixed together prior to subjecting the array to conditions under which a drug candidate salt and crystal or precipitate thereof may form. In one embodiment, the array can be subjected to salt synthesis and crystallization using one or more of the apparatus described herein.

In another embodiment, one axis of the array (e.g., the row) contains the drug candidate of interest mixed with a number of different salt reactants while the opposite axis (e.g., the column) contains solvents or compositions of two or more solvents, wherein each column contains a different solvent or solvent composition. In one embodiment, the solvent compositions in the array or part thereof may be different concentrations of the two solvents relative to each other. The concentrations of the solvents relative to one another may be any concentration desired. In one embodiment, an array of solvent compositions (e.g., gradient) for solvents A and B can be expressed in the following formula:

$$x*A(100-x)*B=0 \qquad (1)$$

where x is the percentage.

If desired the gradient can be determined using a linear function, a non-linear function, a polynomial function, an exponential function, etc. For instance, one may vary the concentration of water and heptane in this manner. Similarly, an array of solvent compositions using three, four or more different solvents may be produced, wherein the relative concentrations of the solvents to each other are varied in the array. In a preferred embodiment, the solvents in the solvent composition have been clustered as described herein. As discussed above, the array can then be subjected to conditions in which drug candidate salts would likely form crystals.

A single drug candidate (either a salt or a neutral compound) is typically tested for polymorph generation and characterization, although two, four, six, eight or more may also be characterized. Because different drug candidate salts do not have to be formed, more solvents are typically used for polymorph generation and characterization than is typical for salt selection. However, except for the larger number of solvents that are generally used, solvent group selection for polymorph generation and characterization is similar to that for salt selection. Thus, in one embodiment, a library of solvents may be divided into more groups for recrystallization compared to that for salt selection, while in another embodiment, more solvents within a single group may be used to recrystallize a drug candidate salt.

In one embodiment of a polymorph array, each well contains a constant amount of the drug candidate of interest and a different solvent. The solvents may be selected by any method known in the art. For example, the solvents may be selected from different industrially important categories of solvents, including aromatics, ketones, water, halogenates, alcohols, esters, nitrites, as well as solvent mixtures that span a wide range of polarity and dielectric constant. In a preferred embodiment, the solvents are selected by the solvent selection method described previously, by dividing a library of solvents into groups based upon a variety of different physical properties or characteristics. More preferably, the solvents are not selected based upon their chemical class. After the solvent has been added to the drug candidate, they are mixed under conditions to dissolve the drug candidate, optionally filtered, and then subjected to conditions in which crystals are likely to form.

Using an array of different types of solvents, whether based upon the chemical class or their physical properties, provides a large amount of information regarding which types of solvents recrystallize the drug candidate. Further, using a wide variety of solvents is likely to provide a large number of different polymorphs of the crystalline drug candidate, if they exist. See, e.g., FIG. 7, which shows changes in crystal morphology of a drug candidate after crystallization from different solvents. These solvents included those that are miscible in heptane and those that are miscible in water. Once one or more solvents have been identified that recrystallize the drug candidate, other solvents that are of the same chemical class or share physical properties or characteristics with the identified solvents may be used in further experiments. These experiments can be performed to generate and characterize polymorphs of the drug candidate as well as to find the best recrystallization solvent for the particular drug candidate.

In another embodiment of a polymorph array, the array contains the drug candidate of interest mixed with compositions of two or more solvents, wherein each well contains a different solvent composition. See, e.g., Example 3. In one embodiment, the solvent compositions in the array or part thereof may be different concentrations of the two solvents relative to each other. The concentrations of the solvents relative to one another may be any concentration desired. In one embodiment, an array of solvent compositions for solvents A and B may be determined using equation 1. Similarly, an array of solvent compositions using three, four or more different solvents may be produced, wherein the relative concentrations of the solvents to each other are varied in the array. In a preferred embodiment, the solvents in the solvent composition have been clustered as described herein. As discussed above, the array can then be subjected to conditions in which crystals would likely be synthesized, and the presence of crystals and polymorphs can be determined. One can use different concentrations of solvents to determine at what concentration a solvent causes the drug candidate to crystallize. In addition, one can use different concentrations to determine whether different types of crystals are formed in different concentrations of solvent.

In another embodiment, solvent group design may be performed by providing a database containing information associating the physical or chemical properties of particular solvents with the production of crystallographic forms of drug candidates, identifying in the database which physical properties are associated with producing a large number of crystallographic forms, and designing new libraries using these identified physical or chemical properties as criteria for grouping solvents.

Figure 5:
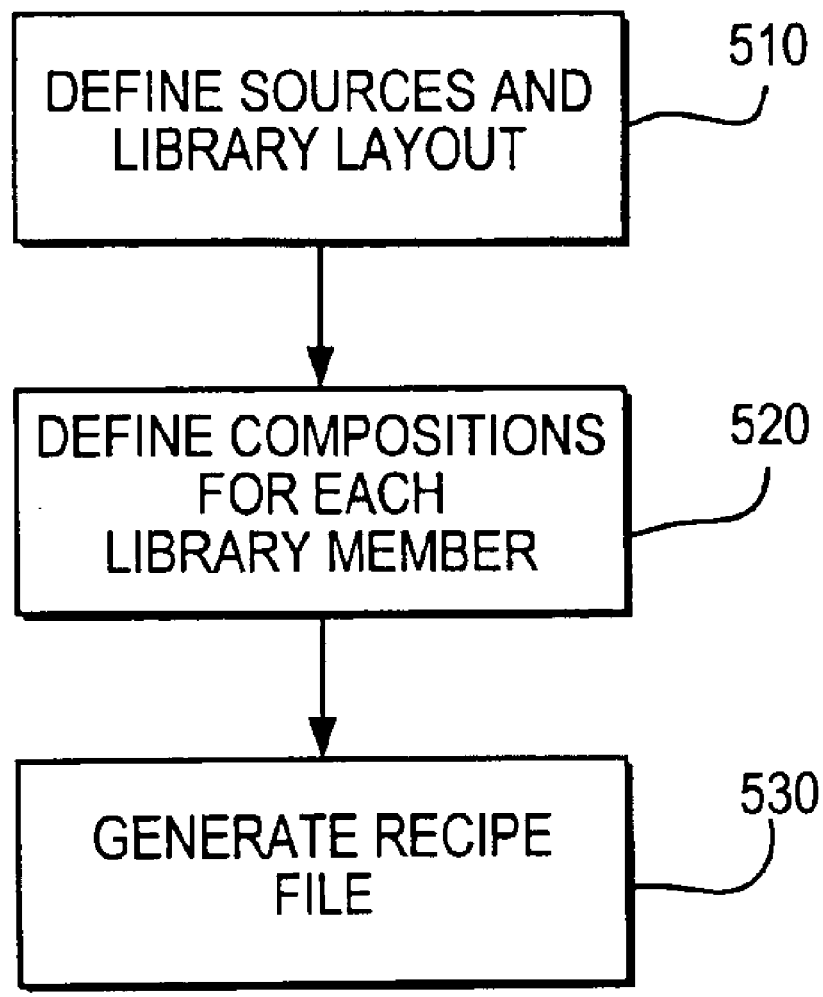
FIG. 5 shows an illustrative flow diagram of a library design process in accordance with the principles of the present invention.

FIG. 5 shows an illustrative flow chart of library design process 500 in accordance with the principles of the present invention. Library design process 500 may be used, for example, to generate library 400 illustrated in FIG. 4. At step 510, a user may define or select one or more sources using a user terminal (e.g., user interface equipment 180 of FIG. 1). Sources may include materials such as salt reactants, solvents, drug candidates, mixtures of solvents, etc. that are used to prepare a library. Also at step 510, a user may define or select a library layout. A library layout may represent the layout in which a library will be created on a substrate (e.g., a substrate with an 12 by 8 matrix array of wells) or a reactor assembly. Alternatively, a library layout is not necessarily confined to actual physical parameters, rather it can be provided in an intangible format (e.g., on a computer).

The user can identify source materials and library layouts by entering identifying information manually or by selecting identifying information from a pre-defined source such as database 114 of FIG. 1.

At step 520, process 500 may define the composition of each library member based on the sources selected in step 510. The composition of each library member is defined by a mapping sequence that assigns materials to each library member. The mapping sequence may be automatically generated or defined by a user. Automatically generated mapping sequences may provide an exhaustive mapping of material compositions than can be used to create libraries.

When step 520 has completed defining the composition of each library member, process 500 optionally proceeds to step 530. At step 530, a recipe file is generated based on the composition defined at step 520. The recipe file may embody handling instructions that can enable instruments such as material handling apparatus 150 (FIG. 1) to prepare the library. Step 530 is optional because the library mapping parameters can be integrated with software that controls a material dispensing apparatus to prepare members of substrate according to the library.

Persons skilled in the art will appreciate that the above discussion with respect to FIGS. 4 and 5 is not intended to be an exhaustive description of library designing. The discussion does, however, discuss a portion of the various features pertinent to describing the present invention. For example, WO 00/23921, provides a substantial description of library designing.

Figure 6:
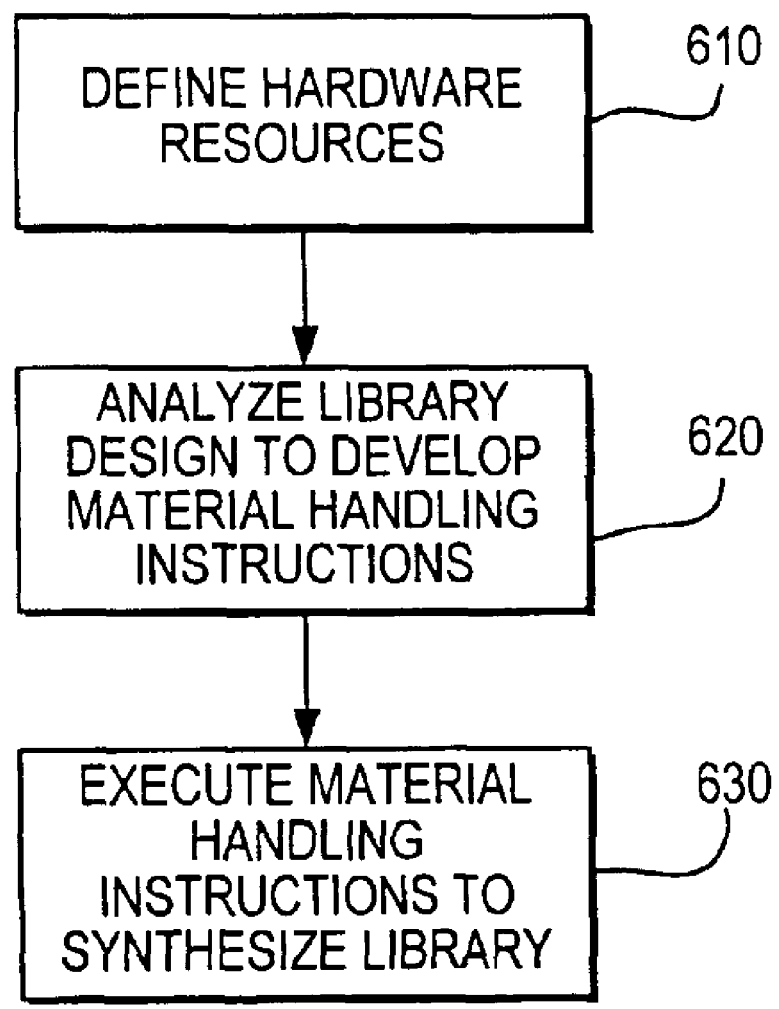
FIG. 6 shows an illustrative flow diagram that generates a recipe file that enables automatic control of hardware to synthesize a library in accordance with the principles of the present invention.

After a library is designed the process proceeds to prepare one or more libraries using material handling apparatuses. FIG. 6 shows an illustrative flow diagram of combinatorial library preparation process 600 that controls hardware to automatically prepare libraries in accordance with the principles of the present invention. Automated step may be performed manually if desired.

At step 610, the user may define hardware resources that are available for use in process 600. The user may define hardware resources such as automated liquid handling robots, pump controllers, solid or powder dispensing systems, and other dispensing equipment. In defining the hardware, the operating characteristics of such hardware may also be identified. For example, characteristics such as configuration of syringes attached to a dispensing device (e.g., in series of parallel), motion limits, step size and reference positions for arm movements, dispensing capacity of syringes, etc. may be identified. Other hardware resources may include temperature controllers for regulating the temperature or temperature ramp rate of a substrate or pressure of a reaction vessel.

At step 620, a recipe file or other instructions that include the library design is received by process 600. Step 620 may analyze the data and develop a set of material handling instructions that can control the hardware to synthesize a library. The material handling instructions may be provided to, for example, electronic circuitry 112 of FIG. 1 so that control commands can be provided to material handling apparatuses. Then at step 630, the material handling instructions are executed and a library is prepared in accordance with the recipe file received at step 610.

Software that can perform process 600 is described in more detail in WO 00/67086, which is hereby incorporated by reference in its entirety.

After salts, crystals, or polymorphs are created in a library format, they are screened for desired properties and characterization. The present invention utilizes high throughput screening that provides sufficient information that enables the process to proceed to the next step. Screening tests are performed to obtain data on each library member. Screening tests can be primary or secondary depending where in the process the test are performed. A minimum number of screening tests may be performed to identify the materials in the library, determine the crystallinity of the materials, and determine the solubility of the materials. Additional tests may be performed to obtain more data on one or more library members.

Screening tests may provide quantitative and/or qualitative data. Quantitative data enables the present invention to perform analysis based on numerical data. This data is well suited for use in software programs operating on computers because it can be categorized quickly and accurately. Qualitative data, however, provides information that does not require intensive number manipulation and relatively quick material characterization. For example, an identity screen can run with sufficient precision to determine if members of the library are different from each other or from a standard. But the identity screen may not be so thorough that it identifies each member of the library. In another example, a crystallinity screen may determine certain crystal characteristics, such as morphology, without determining every (or even most) characteristics of a crystal (e.g., such as melting point, unit cell, etc.).

Screening tests may be implemented on instruments that determine, for example, solubility, partition coefficient (log P), birefringence (while the sample is wet and/or dry), melting point, crystal morphology, hygroscopicity, and other physical characteristics. Other screening test instruments may provided data using, for example, X-ray diffraction, Raman spectroscopy, IR or Near IR spectroscopy, UV-Vis spectroscopy, nuclear magnetic resonance spectroscopy (NMR), gas chromatography and liquid chromatography. These tests are preferably performed in parallel or in a rapid serial or automated mode such that the screening method does not delay the overall process.

As illustrated in FIGS. 2A, 2B and 3, screening test are performed in different steps of the process. One or more screening test may be performed at each screening step in a process. Several screening steps provide greater quantities of data so that library members are more fully characterized than characterizations performed by a single screening test. For example, in one embodiment a primary screening step (e.g., step 225 of FIG. 2A) may perform at least 4 different tests (e.g., solubility, log P, crystallinity and Raman spectroscopy) to determine which library members should be selected for bulk synthesis. Primary screening steps preferably use fewer tests than a secondary screening step so that high throughput screening can be maximized.

A secondary screening step (e.g., step 255 of FIG. 2B) may also perform several high throughput screening test to provide the process with a thorough characterization and identification of the bulk sample. Secondary screening test may include test such as IR spectroscopy, Near IR spectroscopy, UV-Vis absorption, X-ray diffraction, melting point, and $pK_a$. Other tests that can be performed on bulk samples include NMR, differential scanning calorimetry, thermogravimetric analysis and elemental analysis.

A process may perform solubility, birefringence X-ray diffraction, hygroscopicity and/or Raman spectroscopy in high throughput mode to quickly and accurately characterize library members. In particular, when using only solubility, birefringence, and Raman tests, these tests adequately characterize any salts that may have formed. In addition, these test also determine whether polymorphs of drug candidates (or salts thereof) have formed. If desired, a more detailed identification of the different polymorphs can then be accomplished through additional screening test and analysis.

Solubility is performed by sampling the supernatant mother liquor from the recrystallization step of polymorph generation or from the crystallization or precipitation step of salt selection, as described above. The liquid sample is subjected to a concentration detector to determine the amount of the drug candidate (or salt) in the solvent. The drug candidate (or salt) concentration may be detected using liquid chromatography, thin layer chromatography, gas chromatography, absorption in the UV-Vis range, infrared (IR), fluorescence or any other suitable technique. In one embodiment, liquid chromatography coupled with an ultraviolet radiation detector may be used to determine drug candidate concentration. An example of an liquid chromatography system is an Agilent 1100LC system.

Sampling for the solubility test is typically performed at a temperature in which recrystallization or precipitation has occurred. Solubility testing can be performed as a high throughput screen, which can be performed in a rapid serial mode or in parallel. The testing will provide solubility information for the particular solvent in which the drug candidate salt is present at which the solution was sampled. In one embodiment, one may determine the solubility of one or more drug candidates under a variety of conditions in parallel microtiter plates or other assembly comprising a plurality of wells by forming arrays of solvents or solvent mixtures at temperatures ranging from 0° C. to 70° C. and measuring the concentration of the compound in the supernatant. In a preferred embodiment, the temperature is measured at a temperature in which the drug candidate or salt is dissolved ($T_{initial}$) and at the final temperature, in which the drug candidate or salt has crystallized ($T_{final}$).

The partition coefficient, also called log P, is a well known measure of solubility in a water/1-octanol mixture. In a high throughput mode, log P is determined by measuring the concentration of the drug candidate salt in both water and 1-octanol at a particular temperature. In a preferred embodiment, the solubility in 1-octanol and the solubility in water is measured in separate wells of a microtiter plate as part of the overal process, with those measurements used to determine log P. In an alternative embodiment, water saturated with 1-octanol and 1-octanol saturated with water may be used as solvents. The concentration may be detected using liquid chromatography, thin layer chromatography, gas chromatography, absorption in the UV-Vis range, infrared, fluorescence, or any other technique that determines concentration known to those of skill in the art. Using any suitable detection device, log P is determined by dividing the concentration in 1-octanol by the concentration in water and taking the log of that number.

Figure 7:
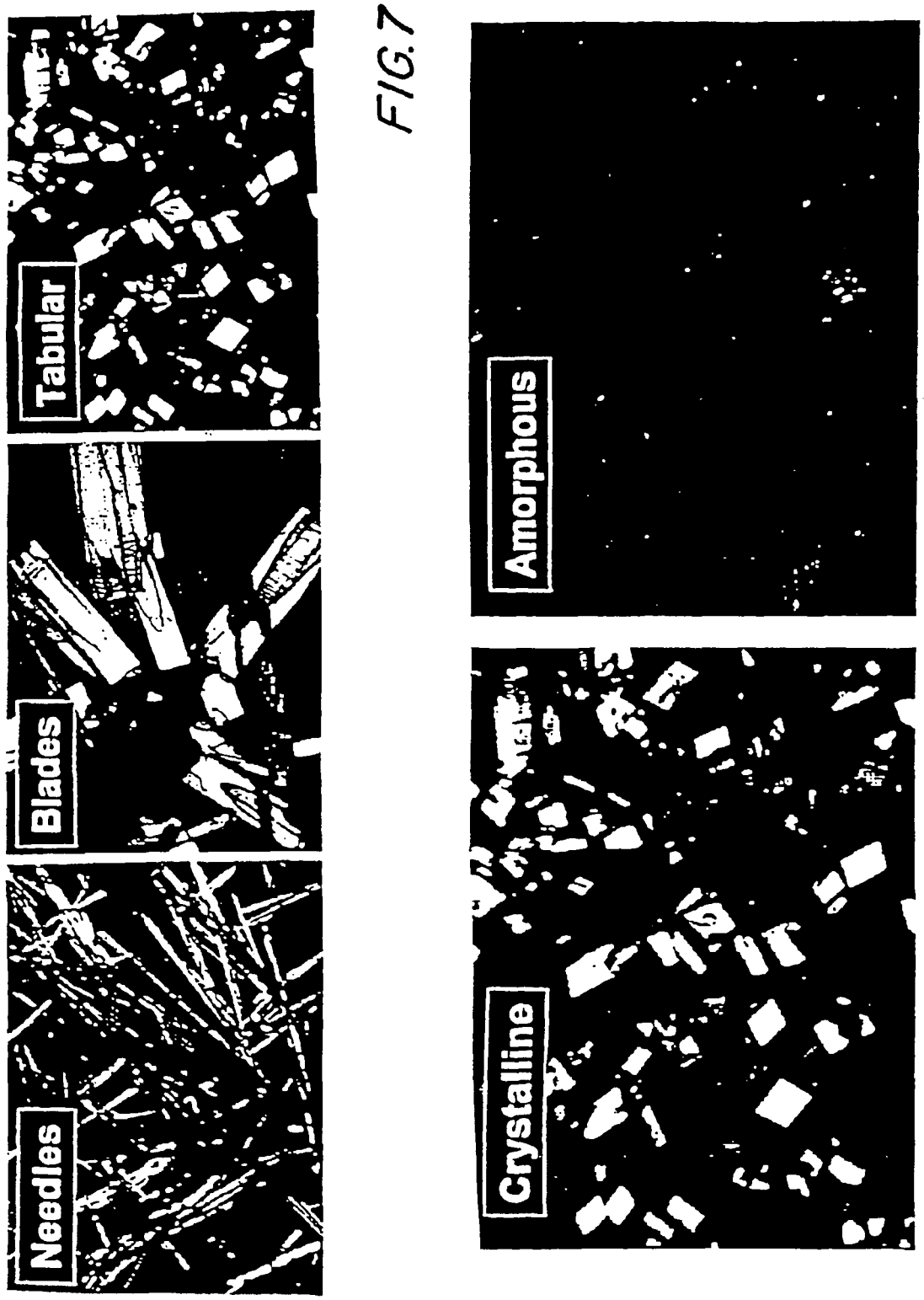
FIG. 7 shows several different crystalline structures that can be detected with birefringence testing in accordance with the principles of the present invention.

Birefringence testing may be used to determine the crystallinity of a sample. In particular, birefringence testing indicates the quantity of crystals formed, size of the crystals, and shape of cyrstal (e.g., needle structure, blade structure, tabular structure, or any other structure). FIG. 7 shows several crystal structures that can be detected using birefringence testing in accordance with the principles of the present invention. The crystal's structure may provide information in deciding which library members are suitable for large scale synthesis. For example, needle crystals are often more difficult to filter than tabular crystals.

Figure 28:
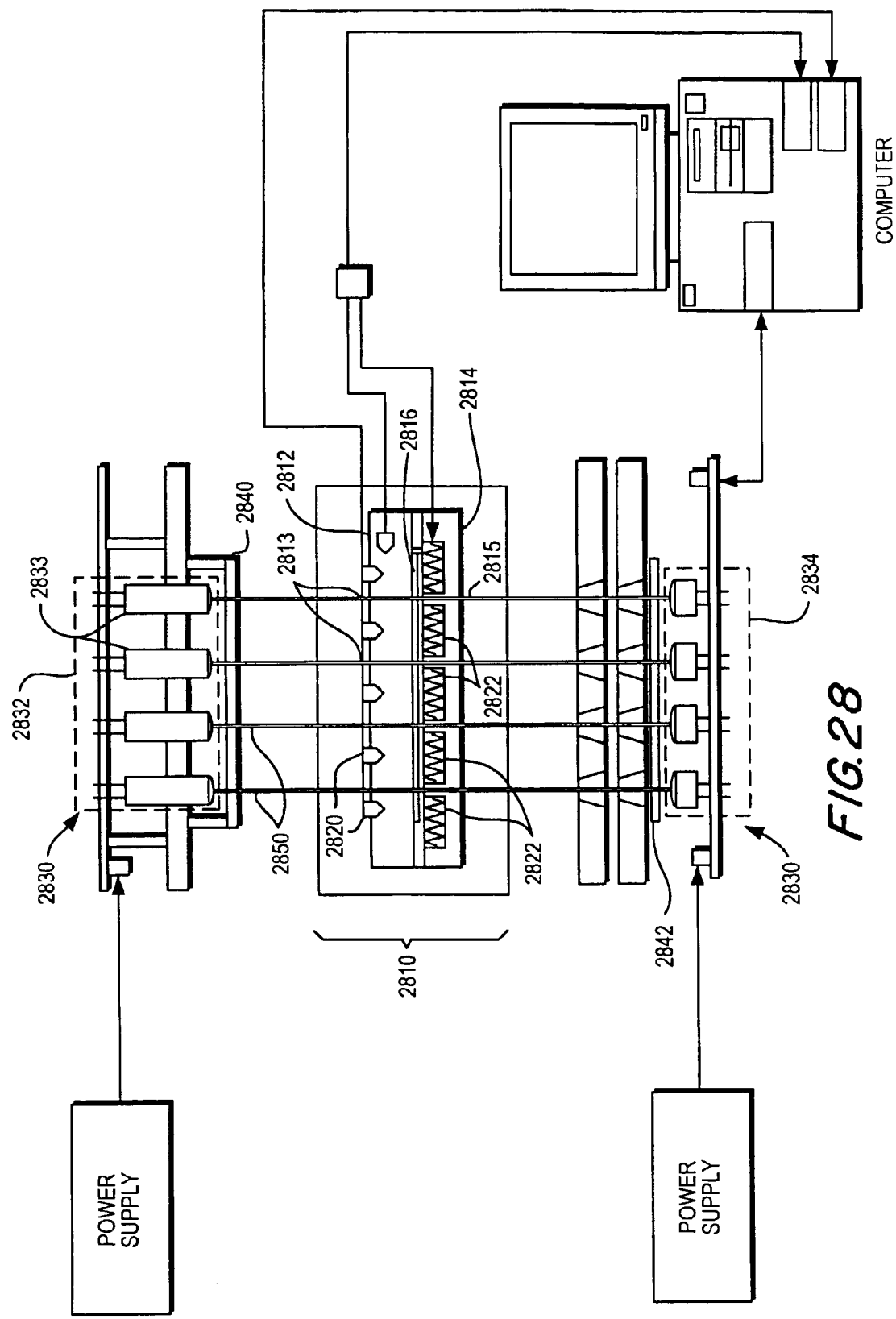
FIG. 28 shows an apparatus that simultaneously performs melting point and birefringence or light scattering testing in accordance with the principles of the present invention.

Birefringence testing may be performed by passing light through wet or dry samples in the library. Preferably, the samples are arrayed on a transparent substrate located between two parallel and perpendicularly aligned cross-polarized filters. A light system may be positioned above or below one of the filters to detect light refraction as it passes through samples on the substrate. Persons skilled in the art will appreciate that other devices can be used to detect birefringence of materials in such a setup. For example, an array of photo-diodes may by used to detect birefringence of a material. The light system advantageously screen the entire substrate in one pass, thus providing a relative fast indication of the suitability of the materials located on the substrate. A detailed description of a birefringence testing device is described in detail in conjunction with FIG. 28. Also described in conjunction with FIG. 28 is a method for performing light scattering to detect if any crystalline structures are present.

Because crystals are birefringent structures, they have the ability to refract light. This property allows a birefringence testing station to detect if a sample on the substrate is crystalline or amorphous. Amorphous materials are typically undesirable because they tend to be unstable and more hygroscopic than crystalline forms. An example of device using a parallel light rotating and collection device is described in U.S. Pat. No. 6,157,449 ('449 patent), which is incorporated herein by reference in its entirety. A birefringence testing station may, for example, use the device in the '449 patent in conjunction with a light system.

In situ measurements of an array of material samples can be performed using birefringence or a light scattering technique. More particularly, in situ measurements are performed using a reflective optical scanning technique. A description of an apparatus that performs in-situ monitoring using the reflective scanning technique is described below in specification pertaining to FIG. 30.

One advantage of in-situ measuring is that it maximizes high throughput testing of material samples. For example, assume that an array of material samples are subjected to crystallization conditions while being monitored in situ. Further assume that these particular crystallization condition did not yield any crystalline structures. Instead of disassembling a crystallization assembly and providing the substrate, which does not contain any crystalline structure, to a series of screening test, in situ monitoring can provide information to avoid such an unnecessary step. Performing screening test on material samples that do not contain crystalline structures slows down the screening process for detecting new polymorphs. Thus, in situ monitoring provides information that may result in subjecting the material samples to different crystallization conditions that may produce crystals.

Hygroscopicity testing characterizes materials (e.g., crystals) according to their ability to adsorb water. Hygroscopicity can be tested in an automated manner using Raman spectroscopy, Near IR spectroscopy or in situ measurements as a series of "snapshots" to determine water gain (or loss), as described in other parts of this specification. PuuMan Oy (Kuopio, Finland) manufactures and markets the HMA (Hygroscopicity Measurement Apparatus) that is capable of measuring the hygroscopicity of eight samples simultaneously.

Hygroscopicity can also be measured by automated weighing systems. For example, vials containing samples are automatically weighed (for example using a Bohdan Automated Weighing Station (called the Balance Automator), available from Bohdan Automation (a Mettler-Toledo Company, Vernon Hills, Ill.). The vials containing samples are then exposed to a controlled atmosphere (e.g., a certain humidity) for a selected time, after which the vials containing samples are automatically weighed again, with a difference in weight being a measure of hygroscopicity. In some embodiments, the automated weighing station can be located inside a glove box or other atmosphere controlled chamber.

Hygroscopicity can also be measure using dielectric measurements. Such dielectric measurements can be performed on a substrate having regions comprising interdigitized probes, with the samples being placed in the regions and the substrate being placed in a controlled atmosphere chamber (e.g., a controlled humidity chamber). Changes in samples dielectric properties are measured as water is gained (or lost) and hygroscopicity is determined.

In a preferred embodiment, hygroscopicity is measured in a high throughput manner using a microbalance and more particularly using sensitive mechanical resonators, whose resonance performance can be monitored and correlated with mass. In one preferred embodiment, hygroscopicity is measured using a method for screening samples created in accord with the description herein (e.g., on a universal substrate), comprising the steps of (a) providing a plurality of solid samples; (b) placing a first sample onto a mechanical resonator in signaling (e.g., electrical, magnetic, optical, thermal, or other communication) communication with a source of an input signal; (c) coupling the mechanical resonator with measurement hardware; (d) exposing the samples to a controlled atmosphere (e.g., moisture or desiccating) while on the mechanical resonator; (e) applying an input signal; (f) monitoring a response of the mechanical resonator to the moisture of the samples thereon with the measurement hardware; and (g) repeating steps (b) through (f) for each sample for which measurement is desired. In addition, this method can readily be adapted for also conducting analysis of mass change in response to a change of temperature, such as for thermogravimetric analysis.

In this preferred method, the monitoring that occurs in step (d) may employ a suitable lock-in amplifier or like hardware for monitoring the change of frequency of the mechanical resonator while maintaining the input signal to the resonator as a constant. It may alternatively employ the monitoring of the change in electrical feedback from the resonator while maintaining a constant frequency.

In a particularly preferred embodiment, the input signal is a variable frequency input signal and the monitoring step (d) includes varying the frequency of a variable frequency input signal over a predetermined frequency range to obtain a frequency-dependent resonator response of the mechanical resonator. The preferred method advantageously allows repeating steps to be performed simultaneously for analyzing an array of samples in a parallel format. Yet, as desired the repeating steps may be performed serially.

When employed in a salt selection or polymorph workflow, as described herein, the preferred method can be described as comprising the steps of (a) providing an array of different particulated pharmaceutical polymorph candidate samples; (b) providing a tuning fork resonator having at least two tines with tips and being in electrical communication with a source of an input signal; (c) adhering a quantity of a plurality of samples to at least one of the tines; (d) coupling the tuning fork resonator with measurement hardware; (e) simultaneously, for at least two samples of the array, humidifying the samples while on the tuning fork resonator; (f) simultaneously, for at least two samples of the array, applying a variable frequency input signal; (g) simultaneously, for at least two samples of the array, varying the frequency of a variable frequency input signal over a predetermined frequency range to obtain a frequency-dependent resonator response of the mechanical resonator to the humidification of the samples; and (h) graphically displaying the responses for each of the samples analyzed, such as by providing a readout of a frequency response, wherein frequency versus signal is plotted.

Another embodiment of the preferred method contemplates an apparatus for measuring small quantities of materials, comprising a plurality of resonators, and particularly tuning fork resonators having tines with tips; a holder for each resonator; a readout board; a plurality of elongated members for bridging electrical communication between the resonator and the readout board; and a frame carrying at least the resonators, holders and elongated members. The apparatus is preferably adapted for attachment to a robot arm for facilitating automation of the operation of the apparatus. The apparatus of may further comprise other components, such as a sample work surface having a recess therein for receiving a sample, a host computer, and a power source (e.g., for providing a variable frequency input signal to the resonators).

The advantages of the preferred method are numerous, including mass measurements of soft, thick, non-uniform layers or irregularly shaped samples; small sample quantity measurements (with some samples being less than about 100 micrograms and more preferably less than about 50 micrograms); certain resonators (e.g., tuning fork resonators) have a Q-factor does not decrease by more than about 1–3%, so relative change of a sample mass is accurately measured by resonator frequency change; quick measurements, in some embodiments in less than one minute (and in other embodiments in less than about 30 seconds or less than about 5 seconds for a single sample or for an entire array or library); and the ability for real-time mass tracking (or real-time hygroscopicity). The details of this preferred method are set forth in commonly owned, U.S. Patent Application Publication No.: US 2003/0218467 A1, titled "High Throughput Microbalance and Methods Using Same", which is incorporated herein by reference for all purposes. See also U.S. Pat. Nos. 6,336,353 and 6,182,499, which are both incorporated herein by reference for all purposes.

Figure 9:
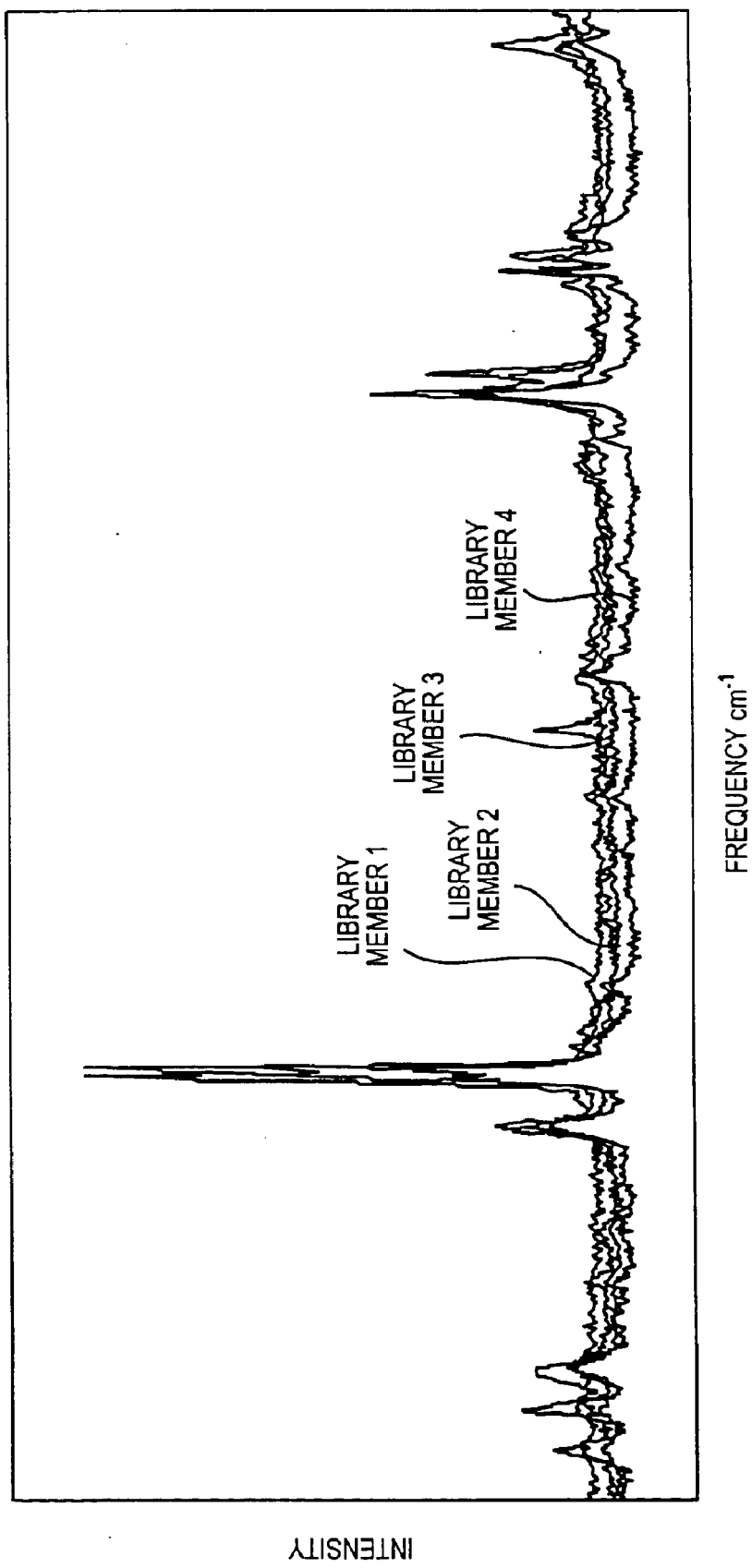
FIG. 9 shows a graphical representation of spectral data obtained from a Raman screening device in accordance with the principles of the present invention.

Raman spectroscopy may be performed using any type of unit, such as a commercially availably unit (e.g., Renishaw, Ramascope), with an X-Y stage that addresses the samples in a rapid serial mode. In some embodiments, in order to run a very high throughput screen, peak assignments may not be performed on the spectra acquired. Instead, the spectra are used as "fingerprints" to determine if different polymorphs (or salts) have formed in the high throughput experimentation. In other embodiments, peak-matching software may be used to make the determination of different identity. Raman, IR, X-ray or other fingerprint type spectra may not be quantitatively analyzed, and instead may be used for qualitative determinations about the relative sameness or differences between spectra. An example of spectra provided in a graph format is illustrated in FIG. 9.

Morphology or crystallinity may also be performed by inspecting each of the regions of the libraries under a microscope, for example, with crossed polarizers. X-ray diffraction can be performed on a Bruker GADDS (Bruker AXS, Madison, Wis.), See also, U.S. Pat. No. 6,371,640, which discloses a method and apparatus of screening materials in a high throughput and library format, incorporated herein by reference.

Thus, selected screening test are used to select drug candidates for further investigation. Screening test also enable the process to perform detailed characterization of library members (e.g., bulk samples) to determine its suitability. The recrystallization condition identified based on the selected samples may be used to prepare bulk samples of the desired salts for additional characterization. One feature of the process of the present invention is the use of a "universal substrate". A universal substrate refers to a substrate having samples thereon and that can be used for a variety of tests (described above) without manual or other manipulation of the samples. This will become more apparent in the discussion below. Thus, a single substrate (e.g., array of materials) can be tested for birefringence, Raman, X-ray diffraction and melting point without handling the samples for each test.

Automated control of material screening device 160 (e.g., birefringence station, Raman station, XRD station, melting point station, etc.) may advantageously enhance high throughput screening. High throughput screening is enhanced by automated control because it allows the process to quickly characterize drug candidates and provide data to a computer (e.g., computer 110 of FIG. 1). Automated control may be provided by a software program operating on a computer. In particular, software programs may control material screening device 160 to characterize and identify properties of drug candidates.

For example, a software program can instruct material screening device 160 to perform an identity screen of the drug candidates. Because drug candidates are typically arranged in a library format, the software can direct device 160 to perform screening in parallel or in a rapid serial mode. Parallel screening provides characterization of two or more drug candidates simultaneously. Rapid serial mode screening provides relatively rapid screening of drug candidates on an individual basis.

Data is obtained from material screening device 160 when it characterizes and identifies properties of drug candidates. This data may be provided to the software so that analysis can be performed with respect to each drug candidate. Data analysis can include categorizing drug candidates, determining suitable drug candidates (e.g., for salt selection), experimental data categorization, and determining polymorphs (e.g., for drug candidates, salts, and other solutions). Data analysis may be performed one or more times during a process. For example, data analysis may be performed after an initial screening to determine which library compositions are suitable for further testing. (This is illustrated in FIGS. 2A and 3 at steps 230 and 335, respectively.) If at least one of the library compositions is suitable for further testing, secondary data analysis may be performed in the process. Secondary data analysis may yield a substantially more rigorous examination of data than primary data analysis and provide accurate results in high throughput. (Secondary data analysis in a process is illustrated in FIGS. 2B and 3 at steps 260 and 360, respectively.) Persons skilled in the art will appreciate that data analysis can be performed as often times as necessary to characterize and examine data.

Figure 8:
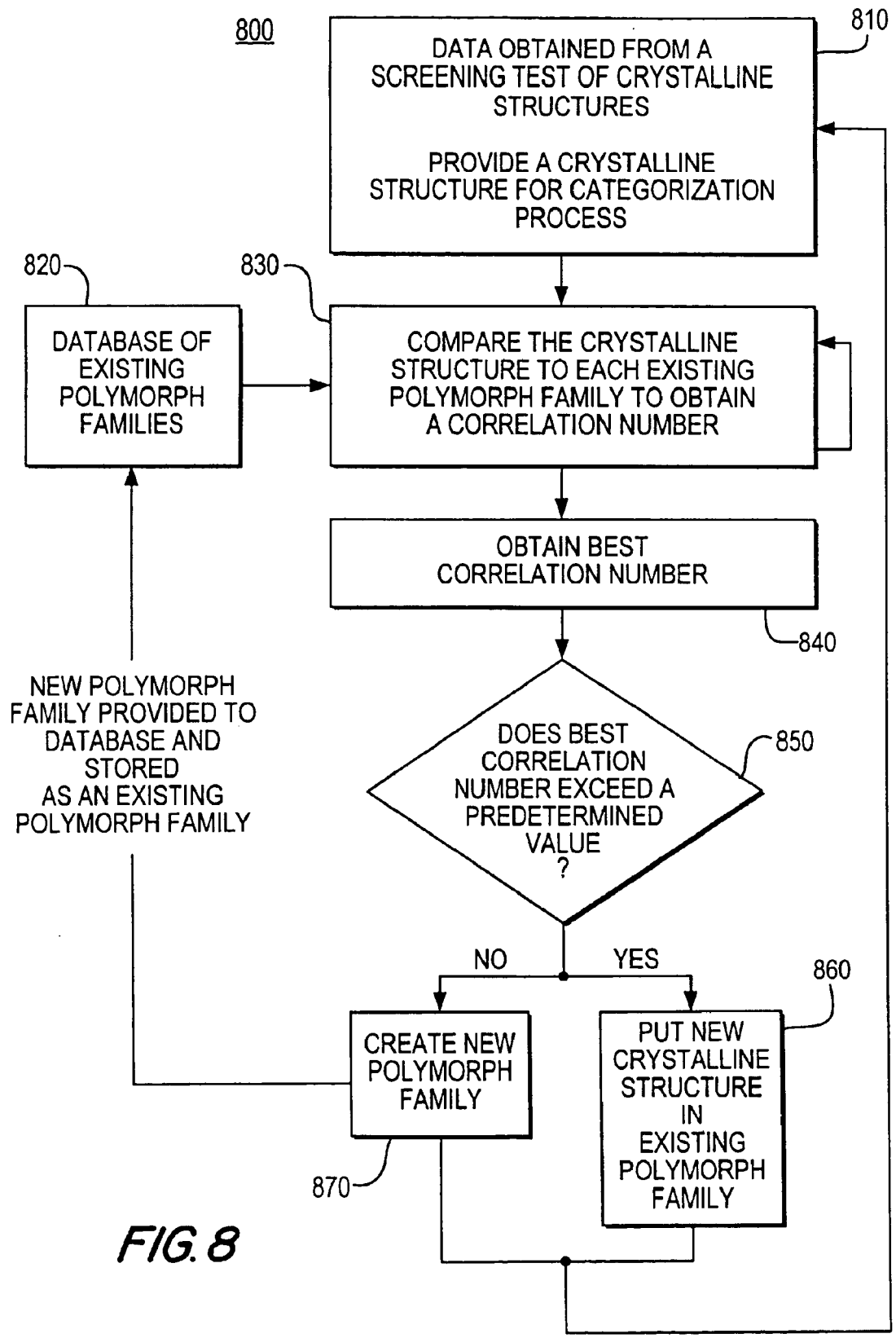
FIG. 8 shows an illustrative flow diagram for categorizing samples according to data obtained in screening tests in accordance with the principles of the present invention.

FIG. 8 shows an illustrative flow diagram for determining if a crystalline structure being tested is part of a particular polymorph family or is a newly discovered polymorph. Categorization flow 800 determines if any material compositions in the library member should be affiliated with an existing family of materials (e.g., existing polymorph family) or if it should be placed in a new family of materials (e.g, new polymorph family). A family comprises a group of materials (e.g., crystalline structures) that exhibit similar characteristics. The categorization of various library members is performed based on data obtained from screening tests (e.g., Raman, XRD, melting point, solubility, hygroscopicity, etc.). One advantage of analysis flow 800 is that it can categorize library members (e.g., hundreds or thousands of materials) into an appropriate family (i.e., existing or new) without relying on initial reference data. Initial reference data can also be used, and in some embodiments, reference data is preferred, such as when a known polymorph exists and others are being searched. Categorization flow 800 builds a database of reference data (e.g,. existing polymorph families) as it categorizes library members with the database being integrated with known or existing data or not. Based on this database, categorization flow 800 continuously analyzes and categorizes crystalline structures created using, for example, process 200 and/or process 300, as described herein.

In the following discussion of FIG. 8, assume that there is no prior data for any of the crystalline structures discussed in this particular example. At step 810, data obtained from a screening test of crystalline structures of the library array is provided. Any above-described screening test can be used to provide data on each crystalline structure. It is preferred that the data set is an XY dataset. For example, if Raman, XRD or another spectroscopic screening technique is used, spectra is provided. Spectra provides data such as peak location, peak height, and peak width of a crystalline structure. If, for example, a melting point screening technique is used, numerical temperature values are provided as data to step 810.

Assuming that the data obtained at step 810 is the first set of data obtained for the first crystalline structure, there is no reference data that can be used for comparison. Thus database at step 820 is void of reference data, at least initially. In particular, step 820 does not have any reference data that represents a polymorph family. For purposes of clarity and brevity, any data that is provided from step 810 that is used in process 800 is referred to as new crystalline structure. Proceeding to step 830, the data associated with a crystalline structure is compared to data for each known polymorph family stored at step 820. Thus, the crystalline structure undergoes an iterative comparison process, which after each iteration, produces a correlation coefficient. A correlation coefficient is indicative of how "close" the crystalline structure is to a particular polymorph family.

Persons skilled in the art will appreciate that methods other than iterative techniques can be implemented to compare the crystalline structure to each of the existing polymorph families.

Categorization process 800 may use statistical methods to obtain the correlation coefficient. Statistical methods may be used to determine the deviation (e.g., standard deviation) of the data associated with the crystalline structure to a reference data set. Software programs that perform such mathematical functions include MATLAB® software sold by The MathWorks, Inc., of Natick, Mass., Mathemathica® sold by Wolfrum Research, Inc. of Champaign, Ill., and MathCad® sold by MathSoft of Cambridge, Mass. Persons skilled in the art will appreciate that other software programs different from the programs described above may be used to perform matrix based calculations and other mathematical calculations.

The comparison process in step 830 uses different comparison techniques differently based on the type of data provided by step 810. One such technique is a cross-correlation technique. This technique is typically used when the measured data is obtained using Raman spectroscopy. As those of skill in the art know, Raman spectra it typically a curve or graph that represents characteristics of a crystal. Such a graph is illustrated in FIG. 9. The cross-correlation technique performs a point-to-point correlation to determine how "close" the measured spectra is to reference spectra. After the comparison is performed, a correlation coefficient is obtained based on how close the graphs match.

Another technique that can be implemented at step 820 is a peak matching percentage technique (e.g., peak locations are compared). This technique is typically used comparing spectra obtained by X-ray diffraction (XRD) spectroscopy. In this technique, the peak locations of an XRD graph are determined using an algorithm. Then the determined peak locations are compared to peak locations of reference data (e.g., peaks of particular polymorph family). A percentage value is obtained based on how similar the XRD peaks are to the reference peaks. This percentage value is analogous to the correlation coefficient.

After the iterative comparisons are performed, the best correlation coefficient is obtained at step 840. The best correlation coefficient is associated with the polymorph family that the new crystalline structure set matched best.

At step 850, the best correlation coefficient is compared to a predetermined value. Typically, the predetermined value is a user-defined correlation coefficient that sets the threshold for determining whether the data associated with the crystalline structure should be associated with an existing polymorph family.

If the correlation coefficient exceeds the predetermined value, that crystalline structure is grouped into the polymorph family associated with that best correlation coefficient at step 860. After step 860, process 800 returns to step 810, which provides the next new crystalline structure to step 830.

If the correlation coefficient does not exceed the predetermined value, a new crystalline polymorph family is created based on the data obtained on the new crystalline structure at step 870. In the event that there was no reference polymorph family for any comparison to be performed, the crystalline structure is automatically used to create a new polymorph family at step 870. The data associated with the new polymorph family is provided to step 820 for use as a reference as an existing polymorph family. Also, after step 870, process 800 returns to step 810. Data from a whole series of libraries based on a single drug candidate can be sorted in continuous process so that one set of families are created that are indicative of the individual forms of the drug candidate.

Thus, analysis process 800 illustrates crystal structure categorization based on screened data. Persons skilled in the art will appreciate that steps shown in FIG. 8 are merely exemplary and that additional steps may be added and some steps may be omitted or modified.

If desired, reference data such as a computer file, a look up table, or other suitable information source may be provided to the database in step 820. Parameters that were used to create the library members can be provided to database in step 820. For example, parameters such as solvents added to the salt, crystallization temperature, and other parameter used to formulate library arrays and crystallize the arrays. This data can be used as criteria in grouping crystalline structures.

Storing measured data provides a database that stores data (e.g., spectra) from each library member. This advantageously enables currently measured data to be compared to other previously screened libraries. In some embodiments, when a new family of polymorphs is discovered in step 825, data from previously identified families may be compared to newly acquired data. This enables analysis process 800 to determine if the "new" family corresponds to a previously identified family such that the data can be assigned to an existing family. This effectively reduces the total number of families of data and allows for a high correlation within a family or group of data. Yet, user defined variation between families or groups is still preserved. In other embodiments, if original data is not provided, the first experimentally determined data can be used as the "starting" information (e.g., step 820 can use data from a designated well or a designated piece of information).

An illustrative example of pre-formulation system 100 (FIG. 1) that implements process 800 to categorize different library members is described in conjunction with FIGS. 9–12. In the following example, assume that each library member of a 96 well substrate has been tested using a device (e.g., an infra-red device, UV-Vis absorption device, a Raman device, an X-ray device) that obtains data. Using such devices, the data can be arranged in a graphical format. FIG. 9 illustrates spectral data obtained from four different library members using a Raman device. The spectral data shows that each of the library members contain polymorphs of the same drug candidate, but are similar enough to be classified as part of the same family or group.

Figure 10:
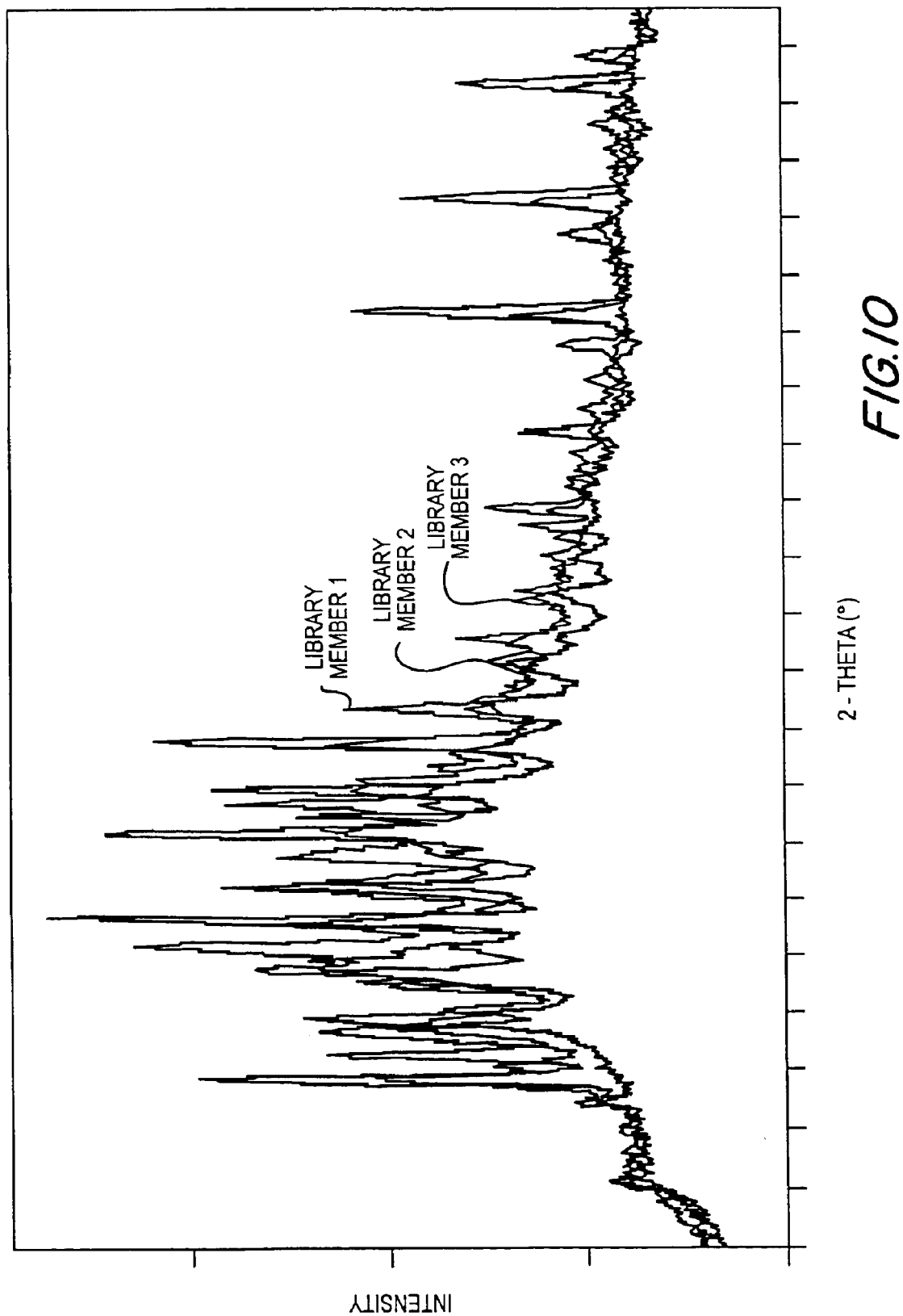
FIG. 10 shows a graphical representation of spectral data obtained from a X-ray screening device in accordance with the principles of the present invention.

FIG. 10 illustrates spectral data obtained from three different library members using, for example, an X-ray diffraction device. FIG. 10 shows that these three library members also have polymorphs, but are each different from each other such that they are not part of the same family group.

Figure 11:
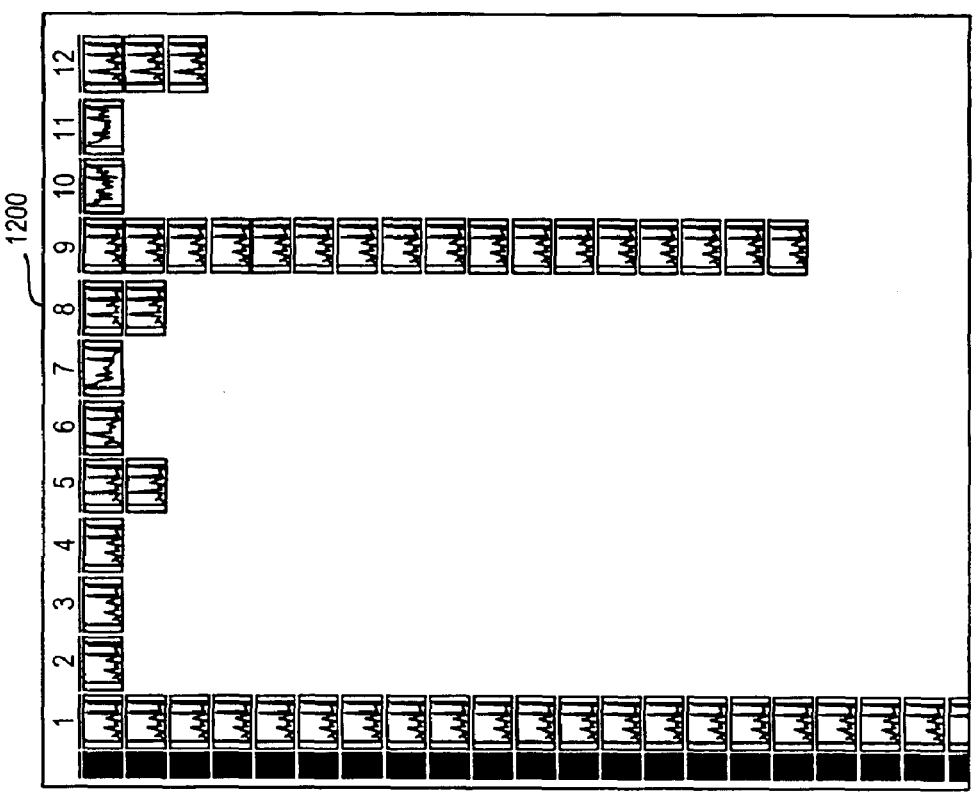
FIG. 11 shows an interactive display screen that includes several spectral data graphs of crystalline structures discovered in an array of materials in accordance with the principles of the present invention.

FIG. 11 shows an illustrative interactive display screen 1100 that includes several spectral graphs of screened library members. Display screen 1100 shows that spectra 1105 are arranged in array format 1108. Preferably, spectra 1105 are arranged so that they coincide with the layout of the substrate in which they were screened. As shown in FIG. 11, not every portion of array 1108 has spectral element. This may be because a crystal did not form during the crystallization (e.g., recrystallization) process.

FIG. 11 also shows that a user can enter and change spectrum sorting parameters 1110. For example, a user can enter a minimum grouping correlation coefficient. As described above in conjunction with FIG. 8, the correlation coefficient may be used to determine if a crystalline structure belongs to a particular family. The value entered for the correlation coefficient can range between −1 and 1. The closer the correlation coefficient is to 1, the more stringent the criteria becomes for placing a particular library element in an existing family. For example, if there are ten library elements and the correlation coefficient is 0.9, each library element may be associated with a new family—thus creating ten different families. If the correlation coefficient is closer to zero, then matching a particular library element to an existing family becomes less stringent, thereby producing fewer new families. The value selected for a correlation coefficient typically ranges from about 0.5 to about 0.9. The correlation coefficient selected may, for example, be the predetermined value used at step 850 in process 800.

A user can select whether to use a fixed reference (e.g., a predetermined reference) or an arbitrary reference (e.g., a library element) for providing a baseline in determining family grouping selection. Persons skilled in the art will appreciate that additional parameters may be entered or modified as suitable within the spirit of the invention. A user may also change the image size of array 1108 by changing width and height parameters 1115. Users can submit their entries by selecting send overlay 1120 or they can reset their entries by selecting reset overlay 1122.

In another embodiment, categorization process 800 may be implemented with an XY dataset where similarity among xy data sets is measured by a correlation coefficient (CC) ranging from −1.0 to +1.0, with +1.0 being a perfect match to be in the same group, which is used for data deemed of insufficient quality. The sorter has a default group, namely the junk group. The parameters for determining the data to be junk or not can be set by the user, with each data set being checked to see if it is junk before being placed in this default location. When a data set is not put into the default location, a new group may be created by comparing the xy data set from the remaining data to a reference and for each unclassified sample xy data set using the reference set from each existing group (or one can pull out all sets from each existing group). Comparison of the sample data to the reference set can provide a CC value (or comparison of the sample data to the sets and get a best CC value from the comparisons). This is followed by retention of the best CC and the Group where the CC comparison came from. If the best CC is less than the specified value, then the sample is put in the new group; otherwise the sample is put into the group from which the best CC was obtained. The user can override the automated classification by performing comparisons visually and assigning groups manually. This can also be implemented on peak locations, peak heights or other data. Thus, for XRD data, it is currently preferred that peak locations are used to determine a correlation coefficient.

In another embodiment, the process also allows the user to define a recycle bin, where data can be designated for re-running through the correlation process. In this manner, the user can identify data that should be sorted based on different parameters. In still another embodiment, the user can iterate the correlation process, by running multiple correlations based on at least one different parameter.

Figure 11A:
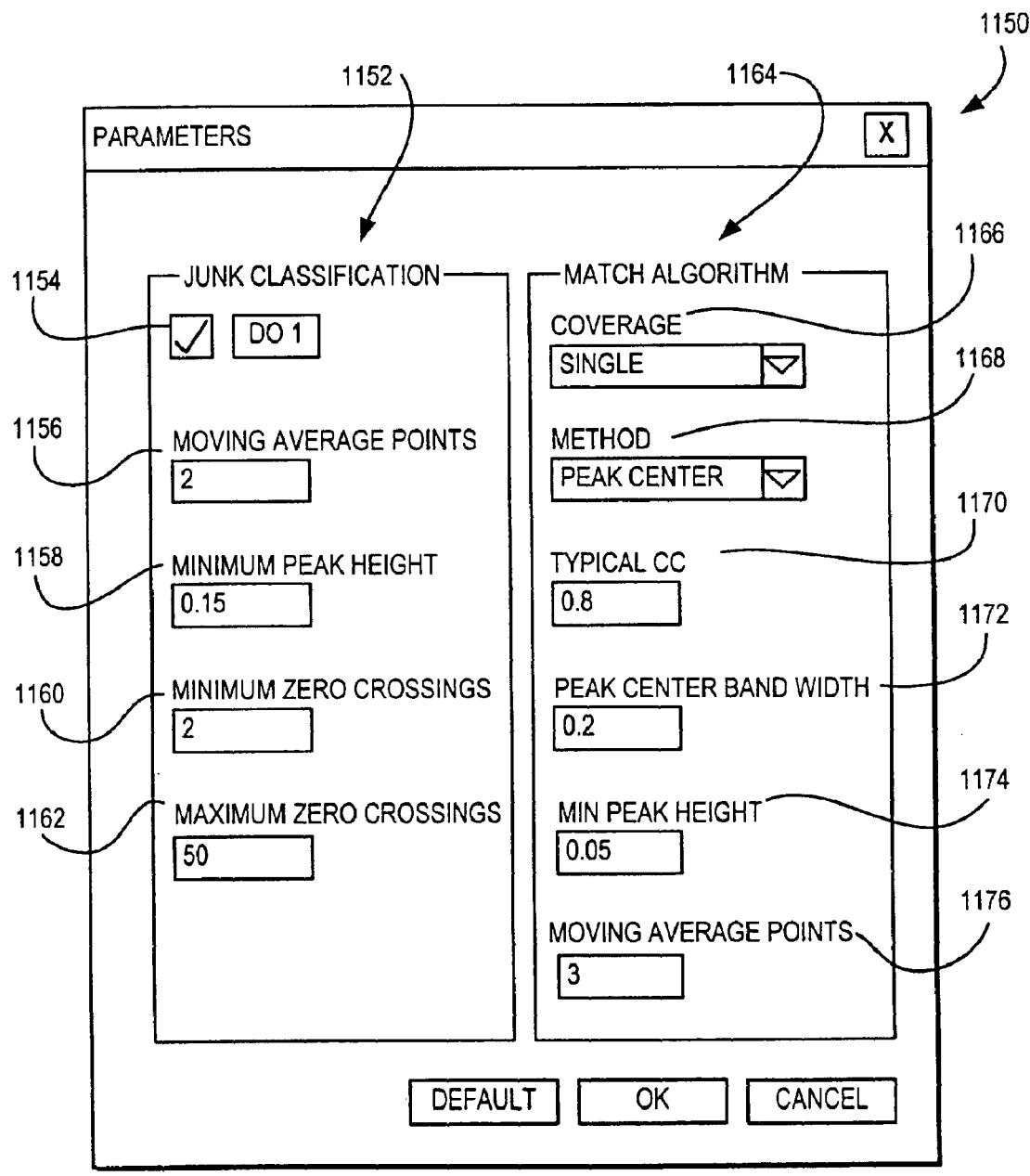
FIG. 11A shows an illustrative display screen that enables a user to define parameters used for correlating data in accordance with the principles of the present invention.

FIG. 11A shows one example of a dialog box 1150 for the user to define the parameters used in correlating the spectra. One side of the box 1150 allows the user to define the automatic junk classification 1152, which as described above allows for removal of data from the classification workflow. The do it check 1154 enables or disables this feature, with the settings that the user can define included in the remainder of the box 1152. The moving average point 1156 is used for smoothing the signal of the data. The minimum peak height 1158 is used for setting the height that a peak in the xy data set must meet in order to be considered to be a peak for correlation purposes (e.g., this feature can set background noise levels and allow the correlation process to ignore the noise). The minimum zero crossings 1160 allows the user to set the minimum number of zero crossings for peaks, with the implicit assumption that each peak has two zero crossings as a default. The maximum zero crossings 1162 allows the user to set the maximum number of zero crossings in a data set so that the data would be considered to have good quality. For example, spectra with too many zero crossings may signify that the spectra may simply comprise noise.

The match algorithm 1164 side of box 1150 is used for setting the correlation factors. The coverage 1166 has settings for single and all, with single comparing the sample to a master or reference data of the existing family or form only. The resulting score represents the comparison score between the sample and the reference data for a particular family. The all setting compares the sample data to all of the data already in the family, in which case that best correlation score represents the best score resulting from all the comparisons. The method 1168 allows the user to decide on what part of the data will be used for correlation. As shown in FIG. 11A, peak center performs correlation based on the peak locations (within an acceptable deviation as defined in the peak center band width 1172). Other methods of correlation include full signal correlation, which uses the entire data set for correlation. Differential signal method of correlation performs correlations based on the digital difference signals (first derivative) of the sample and reference data. Baseline removed method of correlation performs correlation based on data with the curvatures and slopes removed in the data. Other methods of correlation are within the skill of one of skill in the art, including for example with spectra, peak height or peak width. The typical correlation coefficient 1170 is the setting to determine the allowable difference to obtain the best correlation coefficient. The peak center band width 1172 allows for the user to set an allowable deviation in peak centers in spectra data sets. The minimum peak height 1174 generally performs the same function as 1158, and moving points average 1176 allows the user to average set number of data points together for correlation purposes.

Figure 11B:
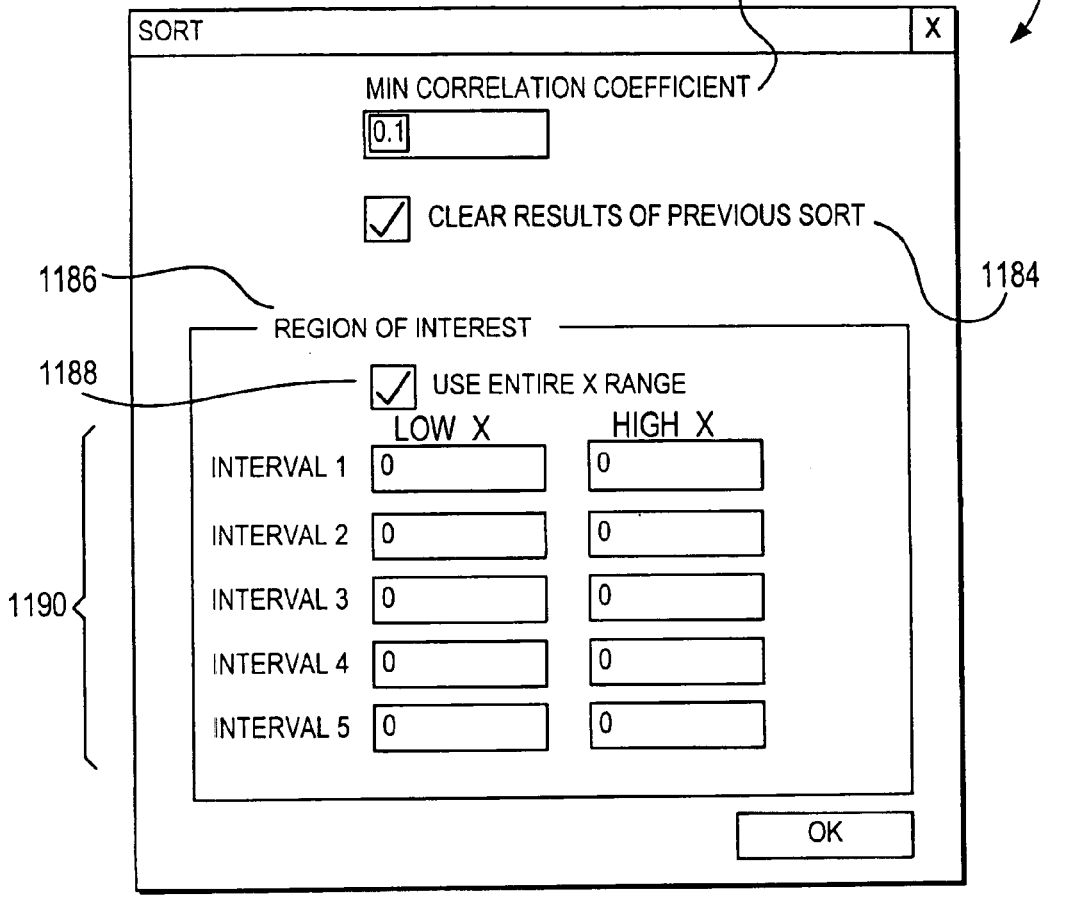
FIG. 11B shows an illustrative display screen that enables a user to define parameters for preforming the correlation of data in accordance with the principles of the present invention.

FIG. 11B shows an example of a dialog box 1180 that allows the user to set the parameters for performing the correlation. The user sets the minimum correlation coefficient, as discussed above, with box 1182. The user can allow for previous sorting results to be used in a new sort by either checking or un-checking box 1184, with use of previous sort results allowing for re-cycling the data, as discussed above. The region of interest 1186 portion allows the user to define a certain portion of the data to consider in the correlation workflow, for example if only a certain region of a spectra would be of interest, then this portion can be used for correlation. As shown in box 1180, this particular embodiment allows the user to set up to five interval ranges 1190 (with a lower setting (low X) and an upper setting (high X)).

Figure 11C:
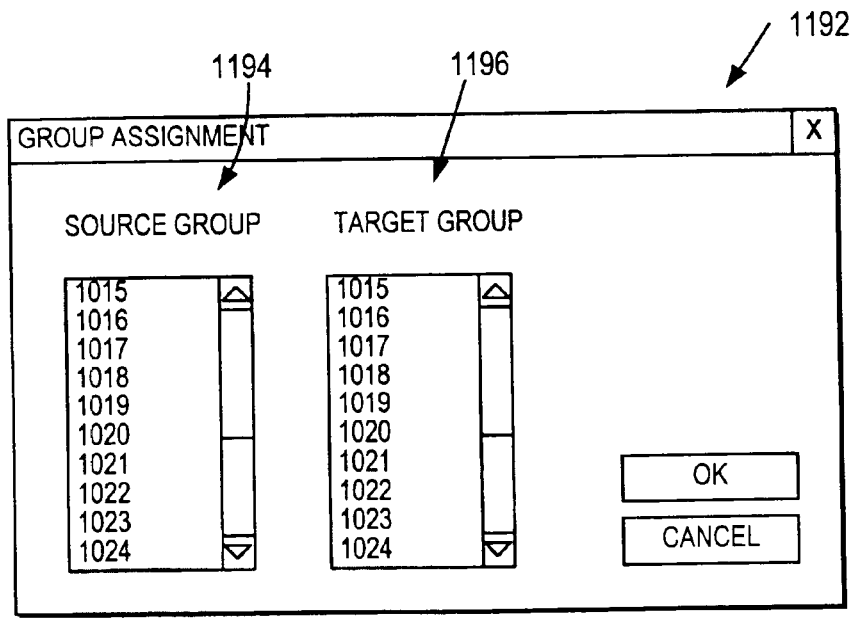
FIG. 11C shows an illustrative display screen that enables a user associate data with particular polymorph families in accordance with the principles of the present invention.

FIG. 11C shows dialog box 1192 that allows the user to manually move data from one group (e.g., family or form) to another group (or family). This feature allows the user to manually create families used for correlation or to manually change correlations.

Figure 12:
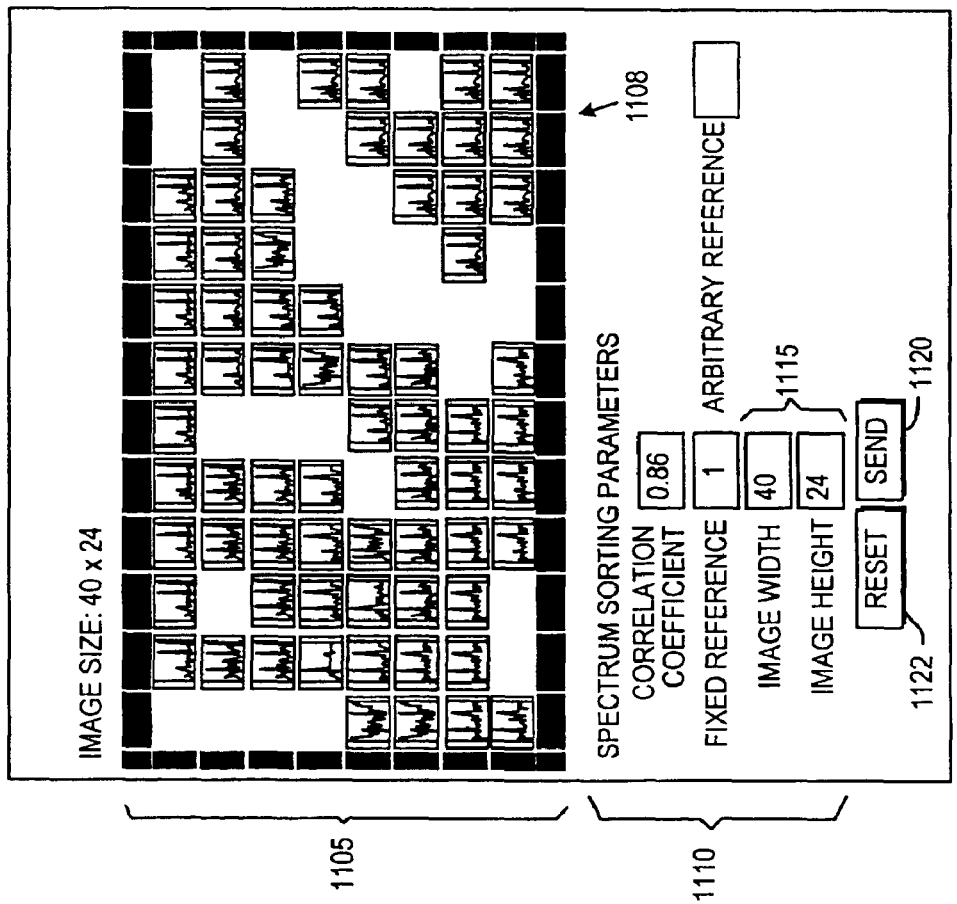
FIG. 12 shows an illustrative display screen that shows the spectral graphs of FIG. 11 in categories in accordance with the principles of the present invention.

When the user selects send overlay 1120 (FIG. 11), the process may analyze the spectral data in accordance with the parameters defined by the user. For example, the process may utilize the principles illustrated in FIG. 8 to analyze and group each library element to an existing or a new family. FIG. 12 shows an illustrative display screen 1200 that has organized each of the library elements of FIG. 12 according to their respective family. In particular, display screen 1200 shows that library elements are grouped into twelve different families. Thus, each of the library elements are grouped accordingly.

A user may repeatedly change the correlation coefficient and select send overlay 1120 to generate different groupings of library members in spectra 1105. For example, if user desires to generate six families of library elements, the user may change the correlation coefficient achieve such a result. A user may desire to do this because a particular number of families is known or expected. The user may know how any families are expected because a different test (e.g., a Raman, hygroscopicity, XRD, melting point) previously yielded such a result.

One advantage of using the software described herein is that a user can run several categorization tests based on different data sets. For example, a user can categorize library members based on data obtained from, solubility, log P, crystallinity, melting point, hygroscopicity, crystal morphology and birefringence, as well as X-RAY diffraction, infrared (IR), Near IR, and Raman spectroscopy, among other screening techniques. After categorization is performed based on two or more such tests, the results of each categorization can be cross-referenced to determine inconsistencies and/or to validate findings of potential new polymorphs.

As described above in conjunction with FIGS. 2A, 2B, and 3, processes 200 and 300 prepare and screen, and analyze library members to group different polymorphs. Because it is an object of the present invention to provide high throughput testing of polymorphs, software can be implemented to optimize the screening process. Software can minimize the number of screening test that need to be performed for a particular library member. Thus, increasing the capacity of the number of library elements that can be tested for polymorphs.

Figure 12A:
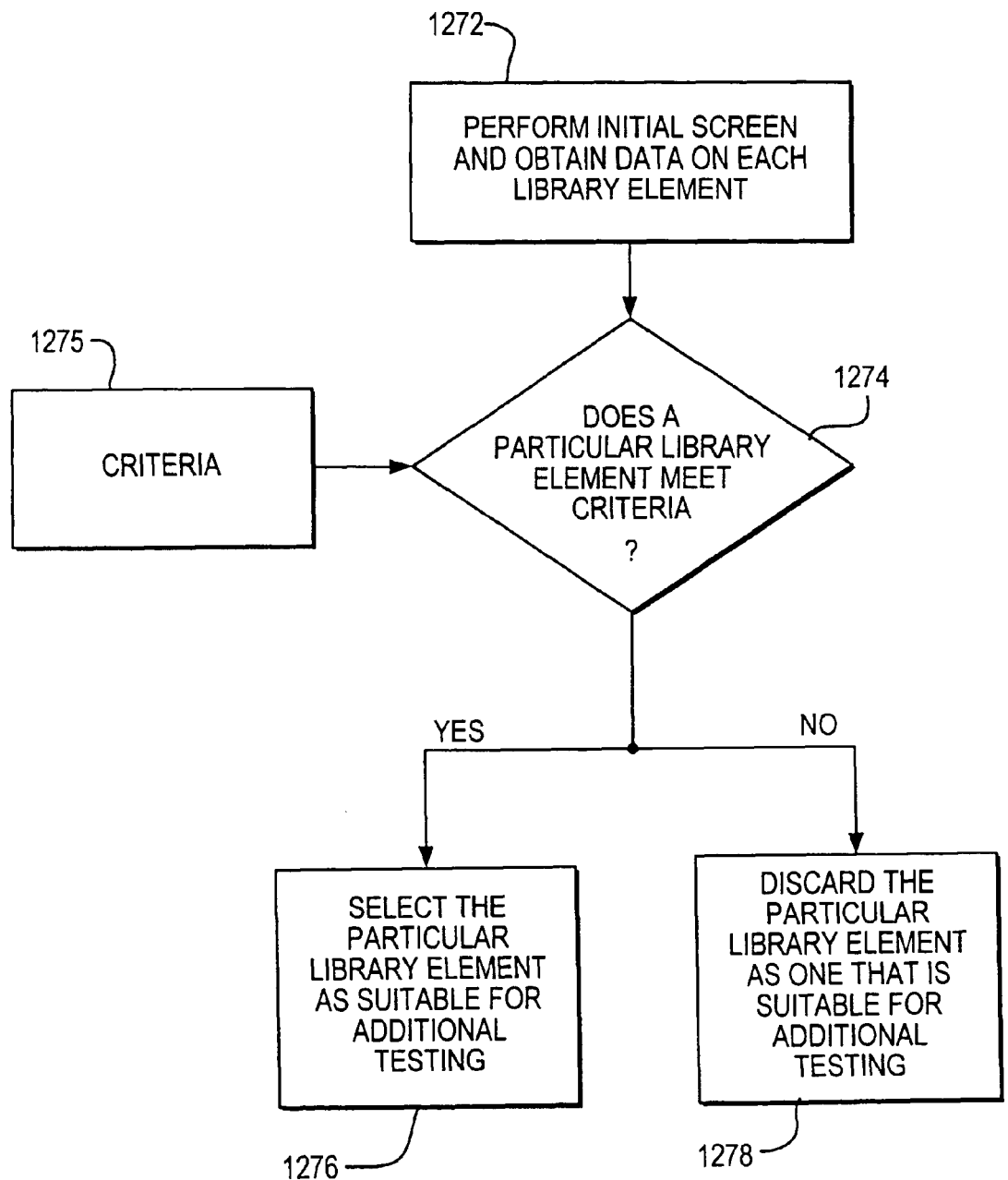
FIG. 12A shows a flow chart of a process that determines if a material sample should be selected for additional testing in accordance with the principles of the present invention.

FIG. 12A shows an illustrative flow diagram of a software process 1270 that determines which library members should be subjected to further testing in accordance with the principles of the present invention. Process 1270 begins at step 1272 in which each of the library members are subjected to an initial screening. Screening, as described above, provides data to a computer, and based on that data, process 1270 can determine whether a particular member is suitable for additional testing. Preferably, the initial screening is a relatively fast screening such as birefringence testing.

At step 1274, process 1270 determines whether the data associated with a particular library element meets certain criteria. The criteria, which is provided by step 1275, includes data that provides a basis or threshold value for selecting which library member should be selected to performed additional testing. For example, if birefringence testing is used, the criteria may be whether any type of crystal structure is present in the library member. The criteria that can be selected for setting the threshold can be selected by a user or the computer program making the determination.

In one embodiment, later screening tests (such as Raman, XRD, etc.) can be performed only on samples having a birefringence image with an arithmetic mean above a determined point. The arithmetic mean may be in this case the mean of all the pixel intensities from an image of the library member under birefringence conditions.

If the data shows that a crystal structure is present in the library member, then that member is suitable for additional testing at step 1276. If, however, the data indicates that no crystal structure is present in that library member, that member is marked as not suitable for additional testing at step 1278. Once a library member is selected, more screening tests (e.g., Raman, XRD, melting point) may be performed. Because performing additional tests take time, process 1270 efficiently eliminates unnecessary testing, thereby maximizing the throughput of the overall process (e.g., workflow).

If desired, the selective screening process can be progressive. That is, assume that a particular library element was selected in an initial screening and was subjected to a second screening (e.g., an XRD screening). Applying the principles described in process 1270, the same library member does not have to be subjected to additional screening test if it fails to meet a minimum criteria standard based on the second screening.

The following describes several apparatuses that are used to implement processes for selecting salts and discovering polymorphs. In addition, the following discussion describes how such apparatuses are used in conjunction with the processes illustrated in FIGS. 2A, 2B, and 3.

Processing of the selected drug candidate or salt(s) for discovery and characterization of suitable forms requires at least two, but preferably three steps, to be carried out in a combinatorial or high throughput mode. The two required steps are dissolution of the drug candidate or salt(s) thereof, and crystallization of the candidate from solution. The optional third step that can occur between the dissolution and crystallization steps is separation of any remaining solids from the solution by filtration or centrifugation. This optional step may be necessary to eliminate nucleation sites for the crystallization step.

Figure 13:
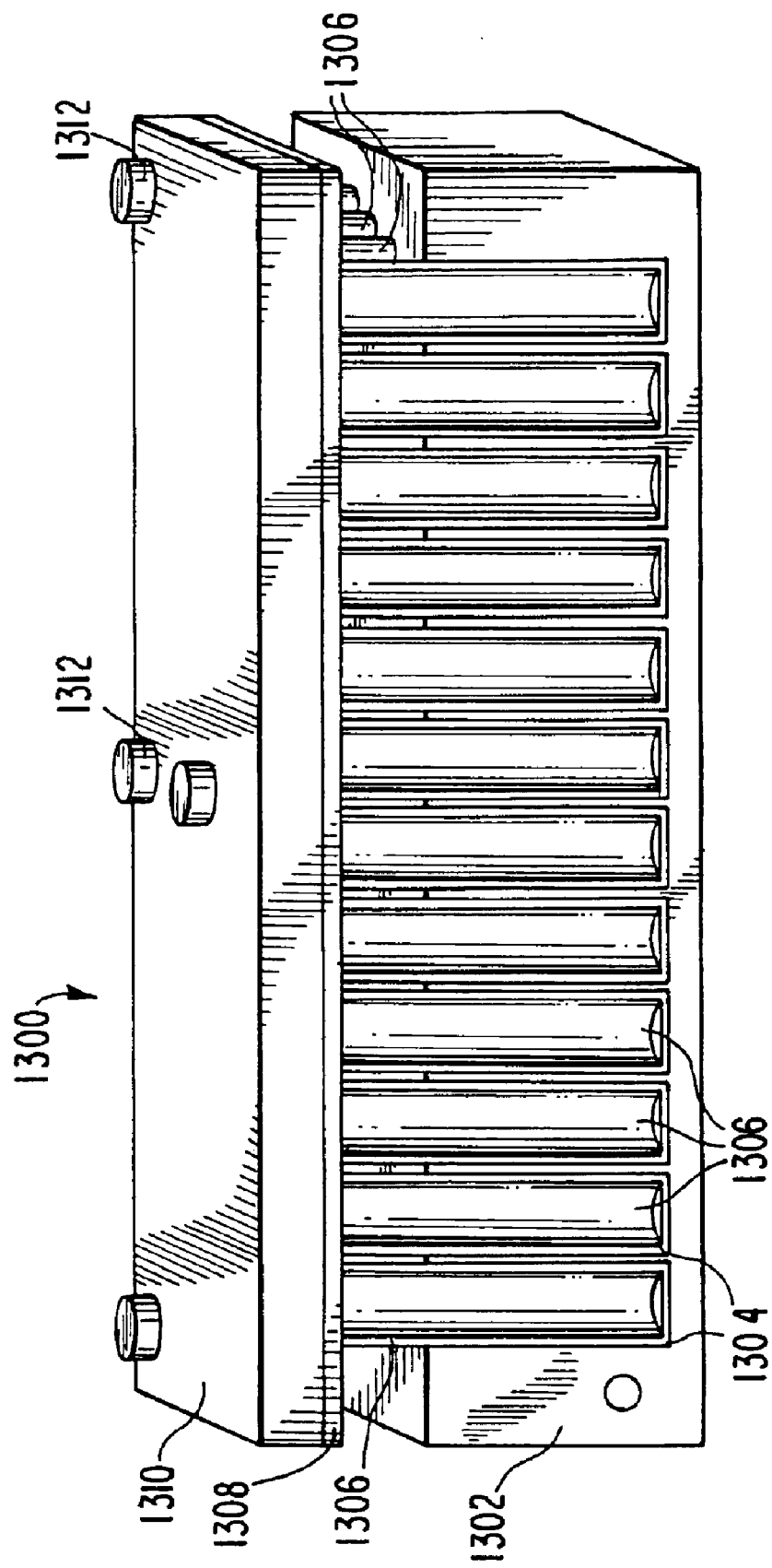
FIG. 13 shows a cross-sectional view of a reactor assembly in accordance with the principles of the present invention.

A general reactor assembly is shown in FIG. 13. A reactor assembly is used for formulating drug candidates, solvents, acids, bases, etc. Reactor assemblies can be used to dissolve solutions for salt selection or to dissolve solutions for polymorph testing. Reactor assemblies such as reactor assembly 1300 of FIG. 13 are suitable for containing reactions of interest.

FIG. 13, for example, illustrates a cross-sectional view of reactor assembly 1300 that can be used for preparing library members in accordance with the principles of the present invention. As illustrated in FIG. 13, reactor assembly 1300 is constructed in microtiter format. Reactor assembly 1300 includes reactor block 1302 that is constructed with one or more wells 1304. Each reactor block 1302 can receive reaction vessels 1306. Materials such as drug candidates and solvents are mixed in reaction vessels 1306. Reaction vessels 1306 are isolated from one another to prevent cross-contamination among the reaction vessels. This can be accomplished by securing sealing sheet 1308 over reaction vessels 1306 by fastening cover plate 1310 to reactor block 1302 with fastening device 1312 (e.g., a bolt, screw, clamp, etc).

Persons skilled in the art will appreciate that any suitable number of wells 1304 may be constructed. For example, a reactor assembly may have 96 wells or it may have 384 wells.

Reactor block 1302 and cover plate 1310 may be constructed of any suitable material such as metals (e.g., steel, aluminum), plastics, and ceramics. Materials such as aluminum or an aluminum alloy may be preferred because they have desirable thermal and structural properties. Reaction vessels 1306 may be plastic or glass, with glass being preferred. Sealing sheet 1308 is typically made from a material that is chemically resistant to the reaction of interest taking place in reaction vessels 1306 as well as being elastic for its sealing properties. Sealing sheet 1308 may be constructed from materials such as Teflon®, silicone rubber, Vitron®, Kalrez®, or equivalents. If desired, sealing sheet 1308 may be constructed with two or more such materials.

Materials can be dispensed into reaction vessels 1306 by hand or by automated robots. Automated equipment may increase the speed and accuracy of step 212 (FIG. 2A). Liquid handling robots such as those sold by Cavro Scientific Instruments, Inc. of Sunnyvale, Calif. may be used for automatically dispensing materials. The description associated with FIG. 6 explains in more detail how the present invention can control robots to dispense materials into reaction vessels 1306.

Figure 15:
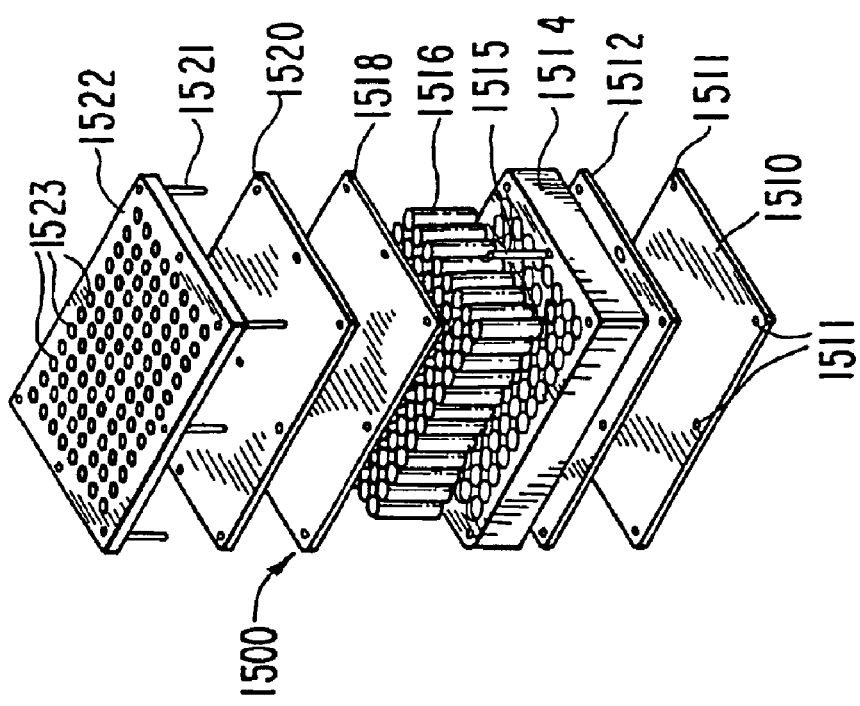
FIG. 15 shows an exploded view of a reactor assembly in accordance with the principles of the present invention.

FIG. 13 provides a general example of one such reactor assembly that can be used in the present invention. FIG. 15 illustrates a more detailed reactor assembly that can be used for formulating a library. FIG. 15 is discussed below in the apparatus section of the detailed description. Also described in the Apparatus section are other assemblies and tools that facilitate preparation of materials. For example, FIGS. 24–28 illustrate heating devices that heat materials contained within the reactor vessels.

Heating and/or agitation of the reaction mixtures in each vessels is often used to promote dissolution of the candidate material in the solvent. Prior to dissolution, mixing/stirring balls or magnetic stirrers (e.g., fleas) may be added to the reactor by hand or with a device such as that shown in FIG. 14 (as discussed in detail below). The reactor block may then be placed on a rocking, rotating, or vortexing plate that is fixed with a heating element for mixing and heating reaction contents. The magnetic-stirring apparatus described above may also be used to agitate the materials. Also, the heating element may be programmable to provide a desired heat cycle.

Figure 14A:
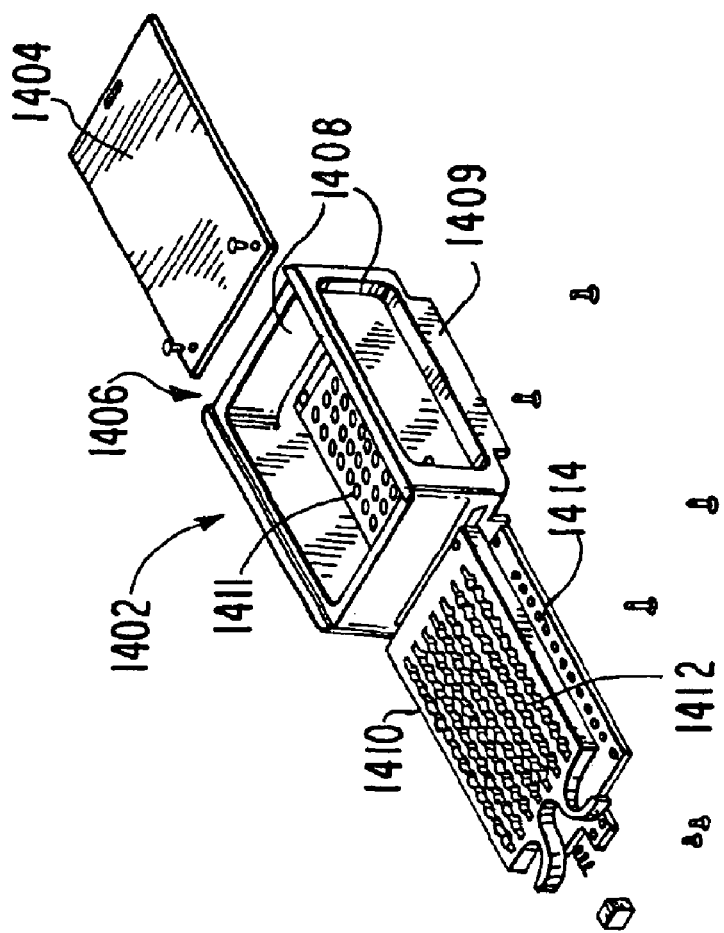
FIG. 14 shows a three-dimensional view of a ball dispensing assembly in accordance with the principles of the present invention.
Figure 14:
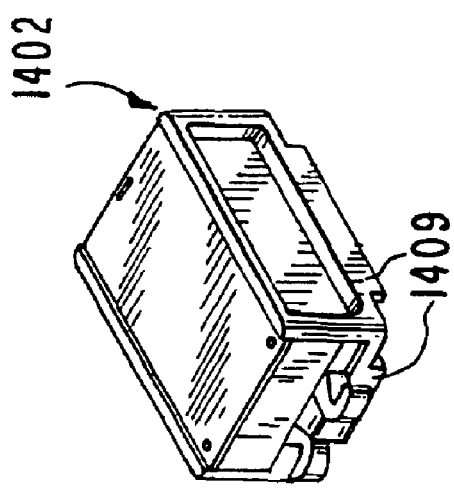

Adding a glass or metal ball to each vial can improve agitation during the dissolution/synthesis step. FIG. 14 and FIG. 14A illustrate a three-dimensional view and an exploded three-dimensional view, respectively, of object dispensing assembly 1402, which dispenses several objects in parallel in accordance with the principles of the present invention. Dispensing assembly 1402 can be secured over a reactor assembly such as reactor assembly 1300 using flaps 1409 that extend from sidewalls 1408 to line up with the outer edges of reactor block 1302 (shown in FIG. 13).

Dispensing assembly 1402 has a cover 1404 that covers a cavity 1406 formed by sidewalls 1408 and bottom plate 1411. Bottom plate 1411 is preferably constructed with a plurality of holes that align to receptacles (e.g., wells or vials) in batch reactor 1300 when dispensing assembly is attached to batch reactor 1300. Also included in dispensing assembly is a separation assembly 1410. Separation assembly 1410 includes isolation plate 1412 and sliding plate 1414. Isolation plate 1412 may have an array of guide holes that guides an object (e.g., ball or magnetic stirrers) to the holes of sliding plate 1414. The operation of dispensing assembly 1402 will be more apparent in the following paragraph.

An excess of objects (e.g., balls) is held in cavity 1406. From this excess of objects, a single object is placed in each guide hole of isolation plate 1412 by shaking assembly 1402. A single object is transferred into each hole of sliding plate 1414 by moving sliding plate 1414 to a first position that aligns the holes in it with the guide holes in isolation plate 1412. In this first position, the holes in sliding plate 1414 do not align with the holes in bottom plate 1411. The objects cannot be dispensed directly into the receptacles in the reactor base below, therefore, one ball is retained in each hole of sliding plate 1414. only one ball is retained in sliding plate 1414 because it is constructed with a thickness that substantially equal to the thickness (e.g., diameter of ball) of the object. Sliding plate 1414 is then moved to a second position which aligns the holes therein with the wells or vials in the reactor base below (via the holes in bottom plate 1411), and simultaneously moves these same holes out of alignment with the guide holes in isolation plate 1412. This permits the object contained within each hole in bottom sliding plate 1414 to drop into the corresponding receptacle below. It should be noted that dispensing assembly 1402 can be modified to dispense different diameter balls by changing separation assembly 1410. The parallel dispensing device shown in FIG. 14 may be used for dispensing other small solids such as stirring fleas.

Regardless of whether agitation objects (e.g., balls) are added to the reactor assembly, an array of solvents or solvent mixtures is added to vials contained within the reactor assembly. The contents are sealed in their respective vials and then agitated at a specified temperature for a predetermined period of time. The temperature typically ranges from about 20° C. to about 10° C. lower than the boiling point of the most volatile solvent in the array. The time period typically ranges from about one hour to about 24 hours. In addition, the mixture may be accelerated by mechanical agitation. In a preferred arrangement the solution is mixed through the use of a vortexer, sonicator, shaker, incubator, or other suitable shaking and heating devices.

Once the solution is fully mixed, the supernatant liquid may be isolated from any residual solid either by hot filtration or by centrifugation. The concentration of the solid dissolved in the supernatant liquid can then be measured by using any suitable technique such as liquid chromatography, gas chromatography, thin layer chromatography, infrared or Raman spectroscopy, and UV-Vis adsorption (as discussed below).

After the materials are mixed, the cover of the reactor assembly is removed and aliquots of the solution (typically a supernatant or mother liquor) are removed and transferred to a glass substrate or a universal substrate and allowed to cool. Glass substrates such as borosilicate reactor plates sold by Zinsser Analytic GmbH of Frankfurt, Germany, may be used in the process. As the solution cools, crystals may form. The rate in which the substrate is cooled can be controlled. For example, the substrate may be subjected to a chilled bath, a thermal module, or a chilling incubator which is sold by Torrey Pines Scientific, Inc., Solana Beach, Calif. Alternatively, particularly when volatile solvents are used, evaporation techniques may be used to generate crystals. If desired, precipitation and slurry techniques can also be used.

After cooling, evaporating, precipitating, or slurry, the supernatant may be removed in a suitable manner (e.g., by aspirating with a pipette and/or wicking away the solvent with filter paper). Supernatant removal can be performed either manually or automatically using a computer controlled device. Supernatant removal can also be performed in serial (e.g., rapid serial mode) or in parallel (e.g., a twelve tip pipette can be used for parallel pipetting). The supernatant and the crystals can both be analyzed for their composition, identity, and properties.

Figure 16:
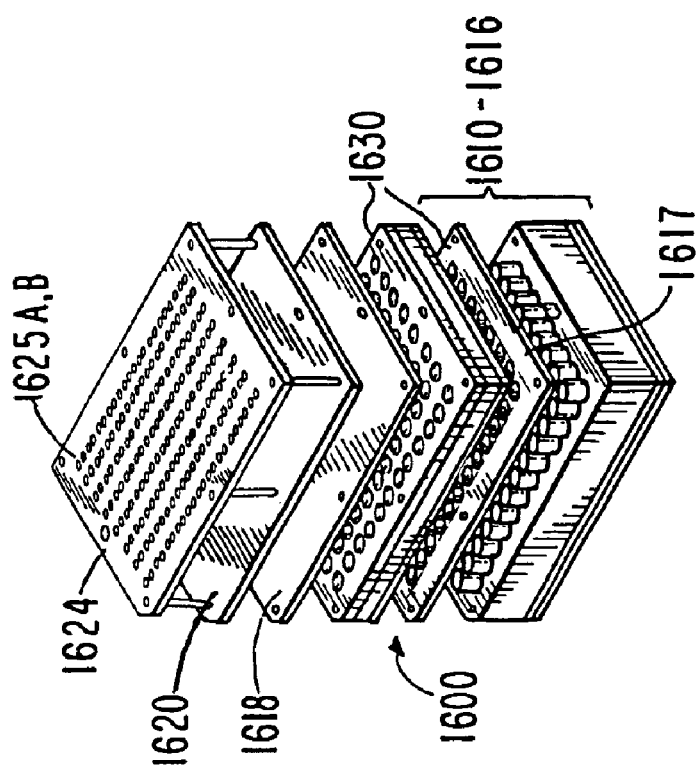
FIG. 16 shows an exploded view of a filtration assembly in accordance with the principles of the present invention.

The above description described how a reactor assembly and substrate are used for performing the processes of the present invention. The following embodiment describes various assemblies that advantageously provide generation of and high throughput screening of salts and polymorphs. FIGS. 15, 16 and 21 illustrate three different assemblies that have several components in common. Although three assemblies are shown, those of skill in the art will recognize that the functions of these assemblies may be combined into two assemblies or into one assembly. Three assemblies are used herein to provide a process that can be implemented relatively quickly using each assembly. When the assemblies of FIGS. 15, 16, and 21 are coupled for use with automatic robots, the process may be performed more quickly and accurately.

FIG. 15 illustrates reaction assembly 1500 which is in accordance with the principles of the present invention. Reaction assembly 1500 is used for a dissolution process, which can include, for example, mixing an array of solvents to a drug candidate and heating the mixture to prepare hot saturated solutions. In addition, dissolution processes can include mixing acidic or basic reactants to a drug candidate to form salts. Moreover, the mixture of chemicals added to formulation assembly 1500 may based on a library model.

Reaction assembly 1500 is generally similar to batch reactor 1300 in FIG. 13, but is different in several respects. Reaction assembly 1500 includes a bottom plate 1510 that has a shock-absorbent layer 1512 positioned on top. Shock-absorbent layer 1512 may include a foam pad or other elastic material. Positioned above these parts is reactor base 1514, which is constructed with an array of holes that can receive vials 1516. Reactor base 1514 and shock-absorbent layer 1512 are secured to bottom plate 1510 using bolts 1511. A barrier sheet 1518 and a septum sheet 1520 are positioned over vials 1516. Barrier sheet 1518 is designed to seal the top openings of vials 1516 and to prevent solvents from mixing with other vials. Barrier sheet 1518 may be made of Teflon® or other suitable material. Both barrier sheet 1518 and septum sheet 1520 may be pierced by a needle or cannula. Reactor cover 1522 is placed over septum sheet 1520 and has holes 1523 therethrough to allow a needle or cannula to pass through. Reactor cover 1522 is secured to reactor base 1514 with bolts 1521.

Although bolts 1511 are specifically discussed herein, other means such as clips, clamps or vices for securing parts of reaction assembly 1500 can be used. FIG. 15 also shows a registration pin 1515 that allows parts (e.g., reactor base 1514, barrier sheet 1518, etc.) to be aligned when being secured together. Several registration pins 1515 may be used to provide accurate alignment.

Vials 1516 pass through the holes of the reactor base 1514 so that the bottom of vials 1516 rest on shock-absorbent layer 1512. Typically vials 1516 are closed at the bottom (i.e., like a test tube with a rounded or flat bottom). Shock-absorbent layer 1512 is made of a resilient material (such as foam) that provides resistance to vertical displacement when downward pressure is applied to vials 1516. Thus, assembly 1500 isolates each vial when the reactor parts are secured together and provides tolerance for dimensional differences among vials 1516. FIG. 15 shows 96 vials in an eight by twelve array, but those of skill in the art will recognize that a different number or arrangement of vials may be used in any particular experiment or format.

If desired, ball dispensing assembly 1402 (shown in FIG. 14) may be used to dispense balls into each vial 1516 prior to sealing reactor cover 1522.

FIG. 16 illustrates a partially exploded view of filtration assembly 1600 which is in accordance with the principles of the present invention. After the mixture is prepared in reaction assembly 1500, aliquots from each vial may be placed in filtration assembly 1600. Filtration assembly 1600 separates particles (e.g., supernatant) of the aliquot, thereby providing a "seedless" solution of the aliquot that can be tested. In addition, filtration assembly 1600 facilitates preparation of an array of parent solutions, which may be daughtered for additional testing.

Liquids are taken from individual wells from the reaction assembly 1500 using a manual or automated pipetting instrument (as described herein) and transferred to the corresponding vials in the array of wells in filtration assembly 1600. The bottom portion of filtration assembly 1600 includes bottom plate 1610, fasteners 1611, shock-absorbent layer 1612, reactor base 1614, and vials 1616. These parts (1610–1616) may be the same parts (1510–1516) as that of the reaction assembly 1500. This allows for common parts to be prepared and used in different assemblies, which reduces manufacturing costs.

Filtration assembly 1600 differs from reaction assembly 1500 by the addition of filter subassembly 1630 and top plate 1624. In addition, filtration assembly 1600 contains a sealing layer 1617 that is similar to barrier sheet 1618 except that sealing layer 1617 has pre-formed holes for allowing the filtered solution to enter vials 1616. These holes have a slightly smaller diameters than vials 1616, thus when filter subassembly 1630 is secured to base 1614 such that sealing layer 1617 provides a seal between vials 1616.

Filter subassembly 1630 in FIG. 16 has two primary functions. Filter assembly 1630 facilitates filtering of the samples received from reaction assembly 1500, and it allows sampling of the filtrate from vials 1616. These functions can be accomplished by combining filter subassembly 1630 with a top plate 1624. Top plate 1624 provides at least two positions for a cannula or needle to deliver or aspirate solutions to vials 1616 in filtration assembly 1600. This arrangement allows for fluid communication between vials 1616 and the top of filter assembly 1600. Specifically, top plate 1624 has holes 1625A and 1625B that correspond to some of or all of vials 1616 in reactor base 1614. For example, hole 1625A may be used to introduce fluid and hole 1625B may be used to withdraw fluid from vials 1616. Details of the apparatus for introducing solutions to be filtered into vials 1616 or withdrawing filtered solution from vials 1616 are discussed below.

Figure 17:
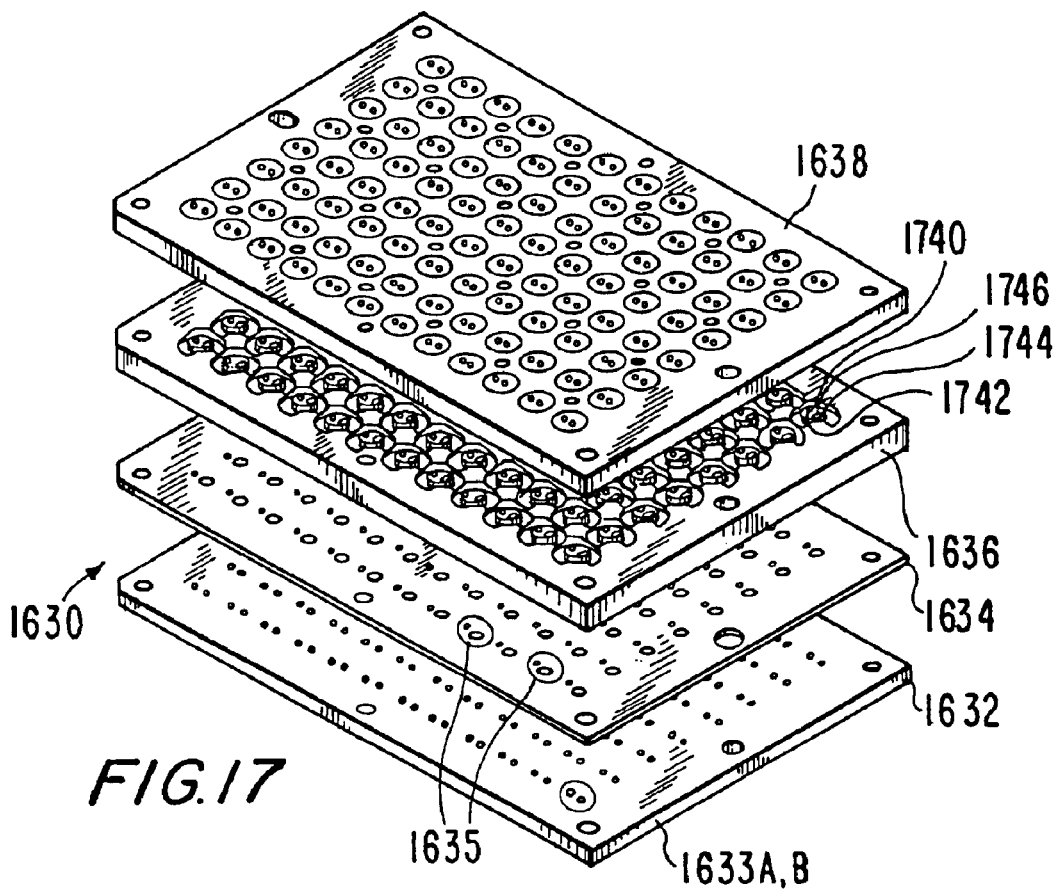
FIG. 17 shows an exploded view of a filter subassembly of FIG. 16 in accordance with the principles of the present invention.

Filter subassembly 1630 is shown in detail in FIG. 17. Filter subassembly 1630 includes a bottom mid-layer 1632 to support filter layer 1634. Filter layer 1634 is used to separate nucleation sites or other undissolved materials from the solution so that a substantially pure solution is provided to vials 1616 (shown in FIG. 16). Filter layer 1634 may be populated with an integrated filter and gasket 1635. Sealing plate 1636 is fitted over filter layer 1634 and provides support for top mid-layer 1638. Bottom mid-layer 1632 has receiver hole 1633A and adjacent hole 1633B located over the upper opening of some or all of the vials or wells in reactor base 1614 (FIG. 16).

Holes 1633A and 1633B permit introduction and withdrawal, respectively, of a solution to vials 1616 (FIG. 16). Sealing plate 1636 supports a large o-ring 1740 and small o-ring 1744 for each region or vial. When filter subassembly 1630 is assembled, each large o-ring 1740 forms a seal between sealing plate 1636 and top mid-layer 1638. This seal, formed by large o-ring 1740, prevents vapor crosstalk between vials 1616. Another seal is formed when a needle passes through small o-ring 1744. Persons skilled in the art will appreciate that other materials may be used to provide seals. For example, seals may be formed with valves such as a Merlin valve sold by Merlin Instrument Co. of Halfmoon Bay, Calif.

Figure 18:
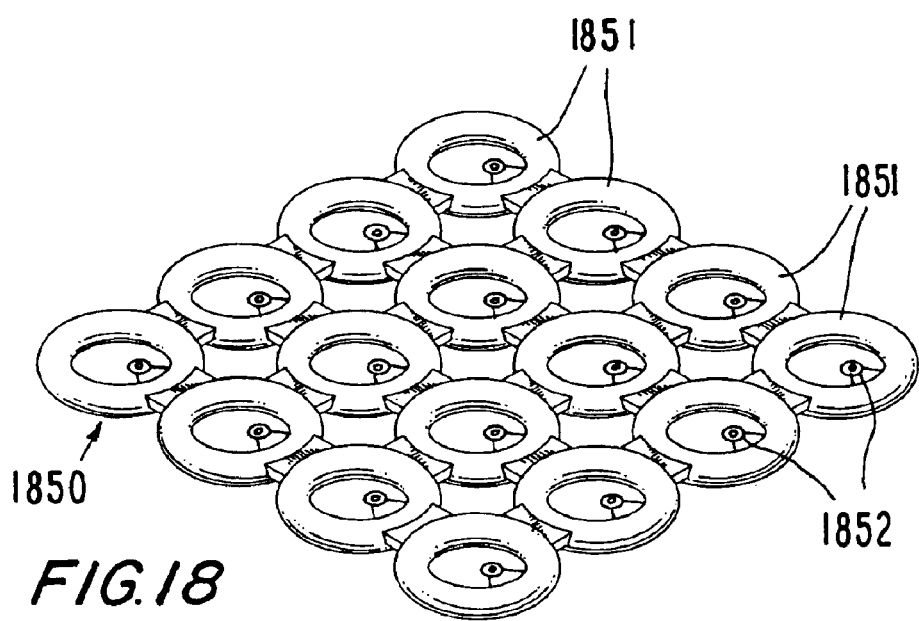
FIG. 18 shows an embodiment of o-ring sheets that may be used in the filter subassembly of FIG. 17 in accordance with the principles of the present invention.

FIG. 18 illustrates o ring sheets 1850 that may be positioned on sealing plate 1636 (FIG. 17) in accordance with the principles of the present invention. Large o ring 1851 and small o ring 1852 can be manufactured in sheets for easier positioning on sealing plate 1636. As illustrated, o ring sheet 1850 is constructed in a four-by-four any of o rings. Thus, if a reactor base has 96 wells, then six o ring sheets 1850 would be required to fully populate a 96 well assembly. Other sizes of o ring arrays ay be used based on the size of each o ring may and the overall number of regions or vials in the reactor assembly. For example, the o rings may be arranged in an 6×8 arm , an 8×8 array, or any other suitable combination.

Figure 19:
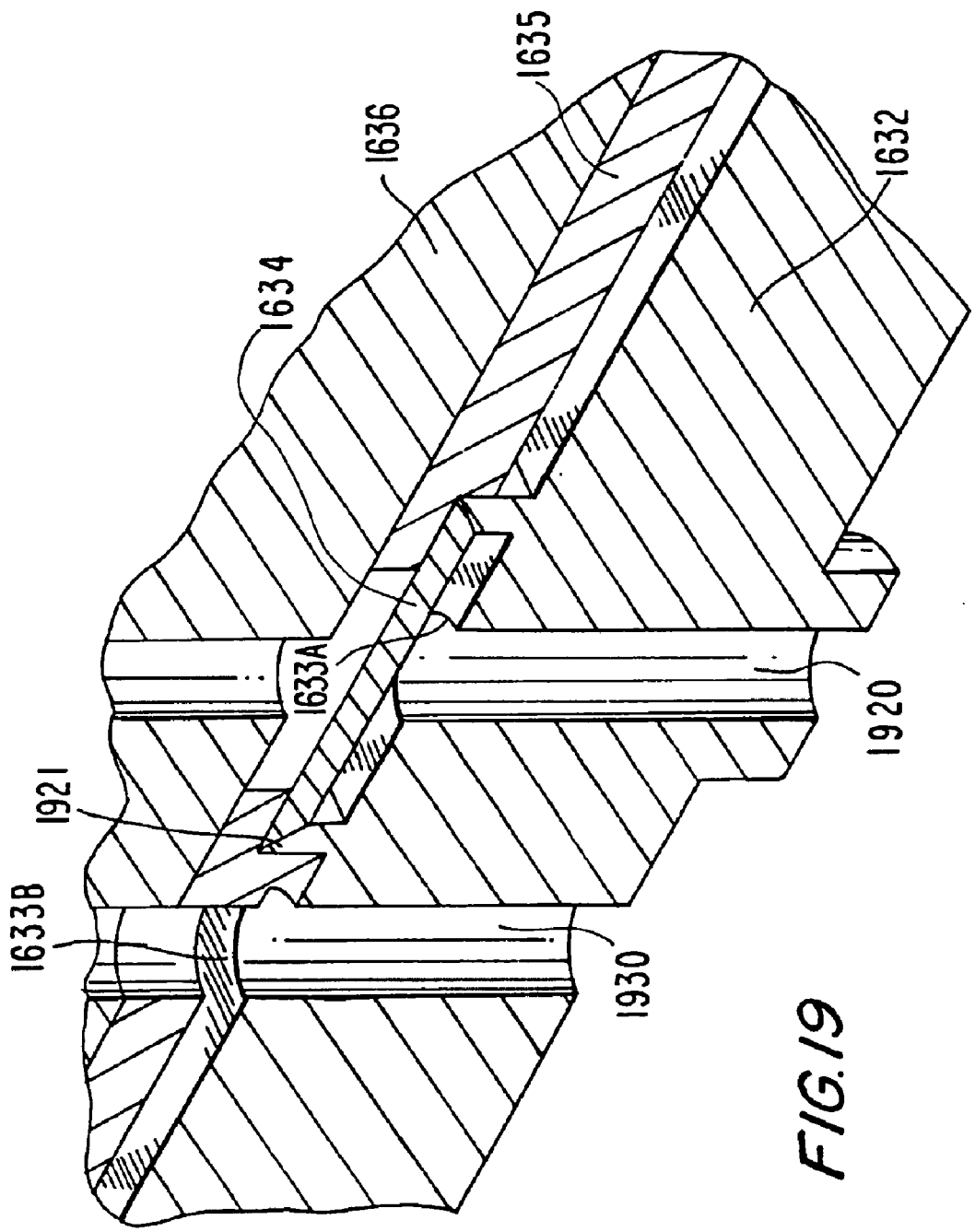
FIG. 19 shows an embodiment of filter disk that can be used in conjunction with the filter assembly of FIG. 16 in accordance with the principles of the present invention.

FIG. 19 shows a close-up isometric view of a portion of FIG. 17. In particular, FIG. 19 shows first channel 1920 and second channel 1930 that are formed when filter subassembly 1630 is assembled. First channel 1920 may correspond to hole 1633A, which may be used for introducing liquid into the filtration assembly. In addition, FIG. 19 shows filter 1634 positioned between bottom mid-layer 1632 and sealing plate 1636. Thus, when liquid is deposited into first channel 1920 via hole 1633A, it is filtered before being deposited in the receptacle. Second channel 1930 may correspond to hole 1633B, which provides a path in which a needle or cannula can directly withdraw filtrate.

In an alternative embodiment, filters may be cut to size so that individual filters are placed into bottom mid-layer 1632, instead of single sheet of filter paper. Filter paper may be cut to size by knife edge ring 1921 that are part of bottom mid-layer 1632. Knife edge ring 1921 may, for example, be associated with the first channel. When a user places filter paper on bottom mid-layer 1632 and impresses it onto each knife edge ring 1921 (only one shown), an array of filter disks on mid-layer 1632 is provided.

Figure 20A:
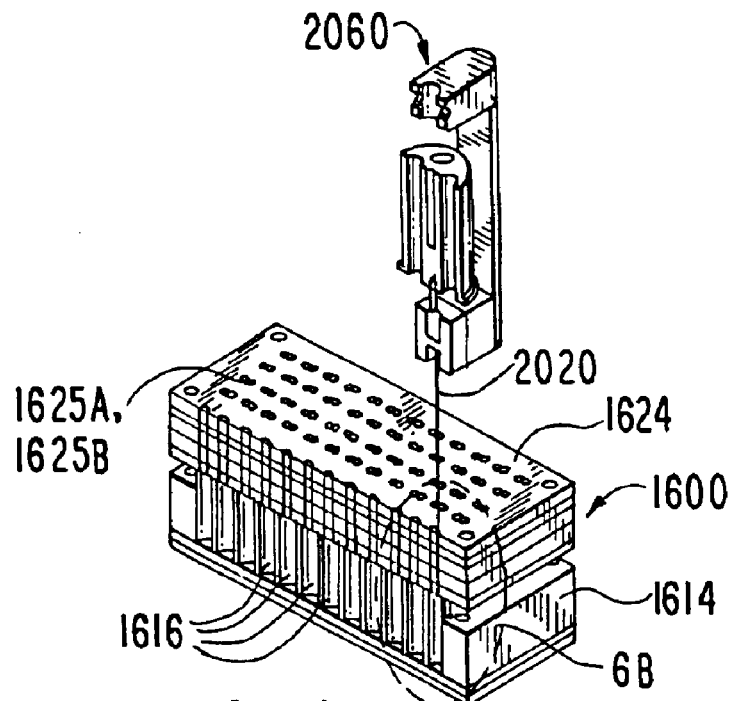
FIGS. 20A and 20B show how a mixture is filtered using the filter assembly of FIG. 16 in accordance with the principles of the present invention.
Figure 20B:
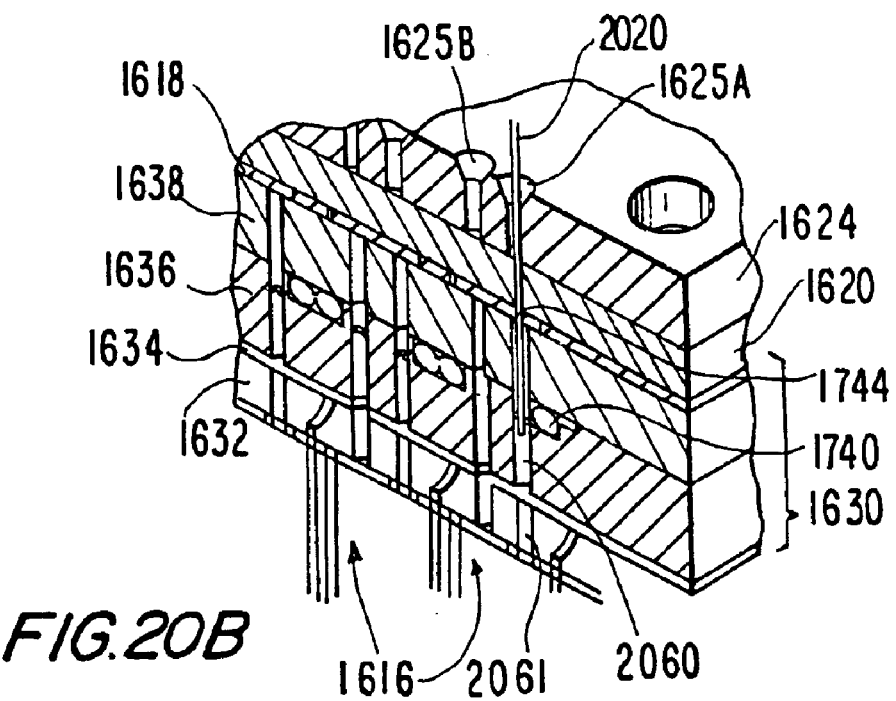

FIGS. 20A and 20B illustrate how pipette system 2060 dispenses into and/or retrieves materials out of vials 1616 using filtration assembly 1600. In particular, FIG. 20A shows a cross-sectional view of filtration assembly 1600 and pipette system 2060 that has needle 2020 extending through hole 1625A. Passing needle 2020 through hole 1625A enables the process to utilize filtration assembly 1600. FIG. 20B illustrates an enlarged view of filtration assembly 1600 encircled with dashed line "6B" in FIG. 20A. Here, needle 2020 is inserted into hole 1625A such that it pierces barrier sheet 1618, septum sheet 1620, and protrudes through small o-ring 1744. As described above, when needle 2020 and small o-ring 1744 interact, a seal is formed. This seal enables solvent to be dispensed into hollow channel 2060 without risk of contaminating other vials. Solvent is dispensed into hollow channel 2060 and is passed through filter layer 1634 or, alternatively, through a filter disk (not shown) to receiver 2061. Receiver 2061 is located in bottom middle layer 1632 and is typically made of chemically resistant material (e.g., plastic) that is designed to prevent wicking away of the solvent passing through filter layer 1634.

The seal between the needle 2020 and small o-ring 1744 should be capable of withstanding sufficient pressure to allow the liquid to be injected into the channel 2060. Bottom mid-layer 1632, sealing plate 1636, and top mid-layer 1638 are typically made of metal (such as stainless steel or aluminum). The filter material in filter layer 1634 or filter disk can be made of an appropriate filtering material that is stable with respect to the solvent media, including materials such as glass microfiber filter pads, cellulose, Teflon®, paper, and other materials used for sample filtration with organic solvents. Filter layer 1634 can comprise a single sheet of filtering material so long as the process is run to avoid cross talk between different array members. Alternatively, several pre-cut filters may be positioned above channel 2061.

Figure 20C:
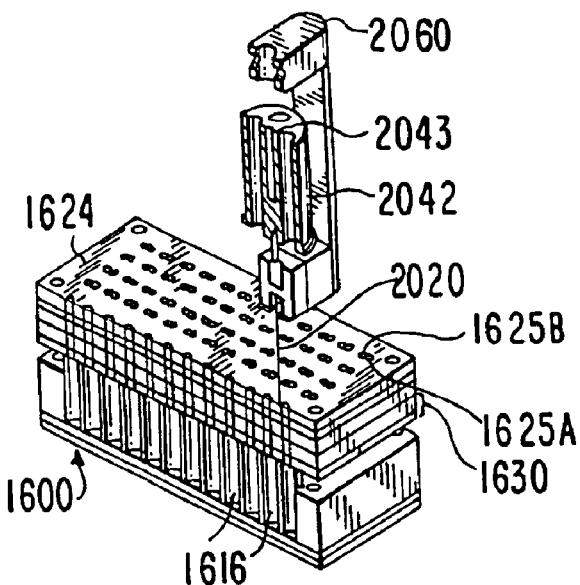
FIG. 20C shows how a filtrate is extracted from the filter assembly of FIG. 16 in accordance with the principles of the present invention.

FIG. 20C illustrates how pipette 2060 can either dispense or retrieve solvent directly from vial 1616. For example, needle 2020 can extend through hole 1625B, barrier sheet 1618, septum sheet 1620, and filter assembly 1630 to directly access vial 1616. This advantageously provides fluid communication between needle 2020 and vial 1616 without using filtering sheets of filtering assembly 1600.

Pipette system 2060 can dispense or retrieve liquids at a specified temperature to prevent undesired crystal formation or precipitation. Pipette system 2060 may utilize, for example, heat sink 2042 and a cartridge heater (not shown) (e.g., a FIREROD heater) to maintain a specified temperature. A cartridge heater may be housed in cavity 2043. Extending from the needle 520 is a wire (not shown) that is wound around heat sink 2040. Because the wire is coupled to heat sink 2040, heat generated in heat sink 2040 is conducted to needle 2020. Thus, needle 2020 is maintained at a temperature that prevents aspirated liquid from cooling. Other designs may be employed to maintain the liquid at the desired temperature, such as a heated tip on a needle, as shown in U.S. Pat. No. 6,260,407, which is incorporated herein by reference in its entirety.

FIG. 21 illustrates crystallization assembly 2100 that is designed to permit the formation of crystals in accordance with the principles of the present invention. Mixtures may be obtained from vials 1616 of filtration assembly 1600 and dispensed in crystallization assembly 2100. Alternatively, mixtures may obtained from vials 1516 of reaction assembly 1500 (shown in FIG. 15). Crystal formation may occur, for example, by cooling the mixture, evaporating the mixture, by precipitating the mixture, or by slurrying the mixture.

One benefit of having separate filtering and crystallization assemblies is that the array of filtrates taken from filtration assembly 1600 can be placed into two or more crystallization assemblies 2100, allowing for crystallization under different conditions or methodologies. For example, this methodology allows for a temperature study to be performed in which more than one array of solutions is crystallized, each at a different temperature. As mentioned earlier, using interchangeable parts in the different assemblies allows for efficiency in inventory and parts uniformity. The different assemblies also permit flexibility in process flow for each part of the recrystallization procedure.

Crystallization assembly 2100 has lower reactor base 2160. Reactor base 2160 has recessed region 2161 that is constructed to receive substrate 2164, which is resting on top of pad 2162. Pad 2162 should be selected to help avoid breaking the substrate. This pad is preferably foam, silicone rubber, or another resilient material.

Substrate 2164 provides a suitable surface for crystal formation. Moreover, substrate 2164 can be transferred to the desired analytical equipment to enable characterization of the array of crystals. The substrate may be constructed from an optically transparent material, such as glass, to allow for direct optical studies of the crystals on the substrate. It can also be made of other materials such as plastic. Substrate 2164 may have a substantially flat surface on which the crystals are contained. Substrate 2164 may have distinct regions on its surface to support crystals formation. For example, those distinct regions may be round, square, etc. The regions may also be recessed to readily retain crystals. Thus, dimples or wells can be used. (A dimple herein is defined as a depression with a rounded concave surface, and a well is a recess with one or more defined sidewalls.)

Above substrate 2164 is gasket 2166 having an array of holes (not shown) that correspond to the array of regions on substrate 2164. When assembled, these lower components (pad 2162, substrate 2164, and gasket 2166) will fit into recessed region 2161 so that gasket 2166 is secured substantially flush against the upper outside edges of reactor base 2160. Crystallization reactor 2168 is placed over these components and secured to reactor base 2160 using bolts 2170 or other securing means (clips, clamps, nuts, etc.). The securing means should provide sufficient force to compress gasket 2166, which in turn seals the regions on substrate 2164 from potential crosstalk.

Crystallization assembly 2100 also includes sheet 2172 (typically made of Teflon®) and septum 2174 (which may be identical to barrier sheet 2118 and septum 2120, respectively) and reactor cover 2176 covering crystallization reactor 2168. Reactor cover 2176 is similar to reactor cover 2122 for reaction assembly 1500, having holes through which needle 2020 may pass. The parts over crystallization reactor 2168 are secured to crystallization reactor 2168 by bolts 2178 (although other clamping, clipping or securing means may be used). Thus there are two sets of secured components in crystallization assembly 2100. The first set includes crystallization reactor 2168, gasket 2166, substrate 2164, pad 2162, and reactor base 2160. The second set includes sheet 2172, septum 2174, and reactor cover 2176, which together are coupled to crystallization reactor 2168. These separate sets permit the bottom part of crystallization assembly 2100 to be assembled without the upper portion, resulting in more flexibility in being able to use part or all of crystallization assembly 2100 for pre-formulation testing.

Reactor cover 2176 and septum 2174 may not be used if evaporation studies are to be tested with the material samples contained within cyrstallization assembly.

Figure 21A:
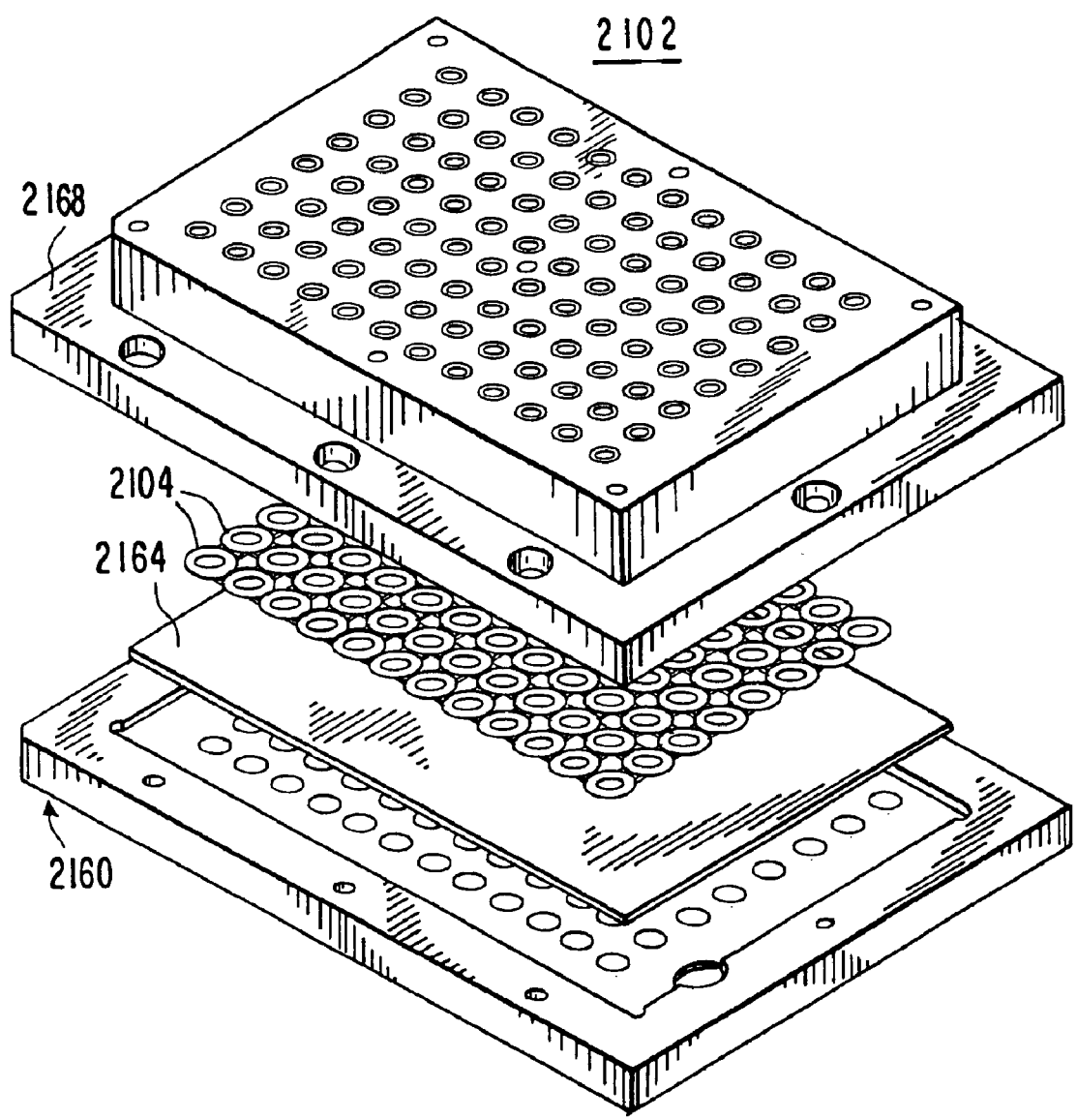
FIG. 21A illustrates an exploded view of an alternative embodiment of a crystallization assembly in accordance with the principles of the present invention.
Figure 21B:
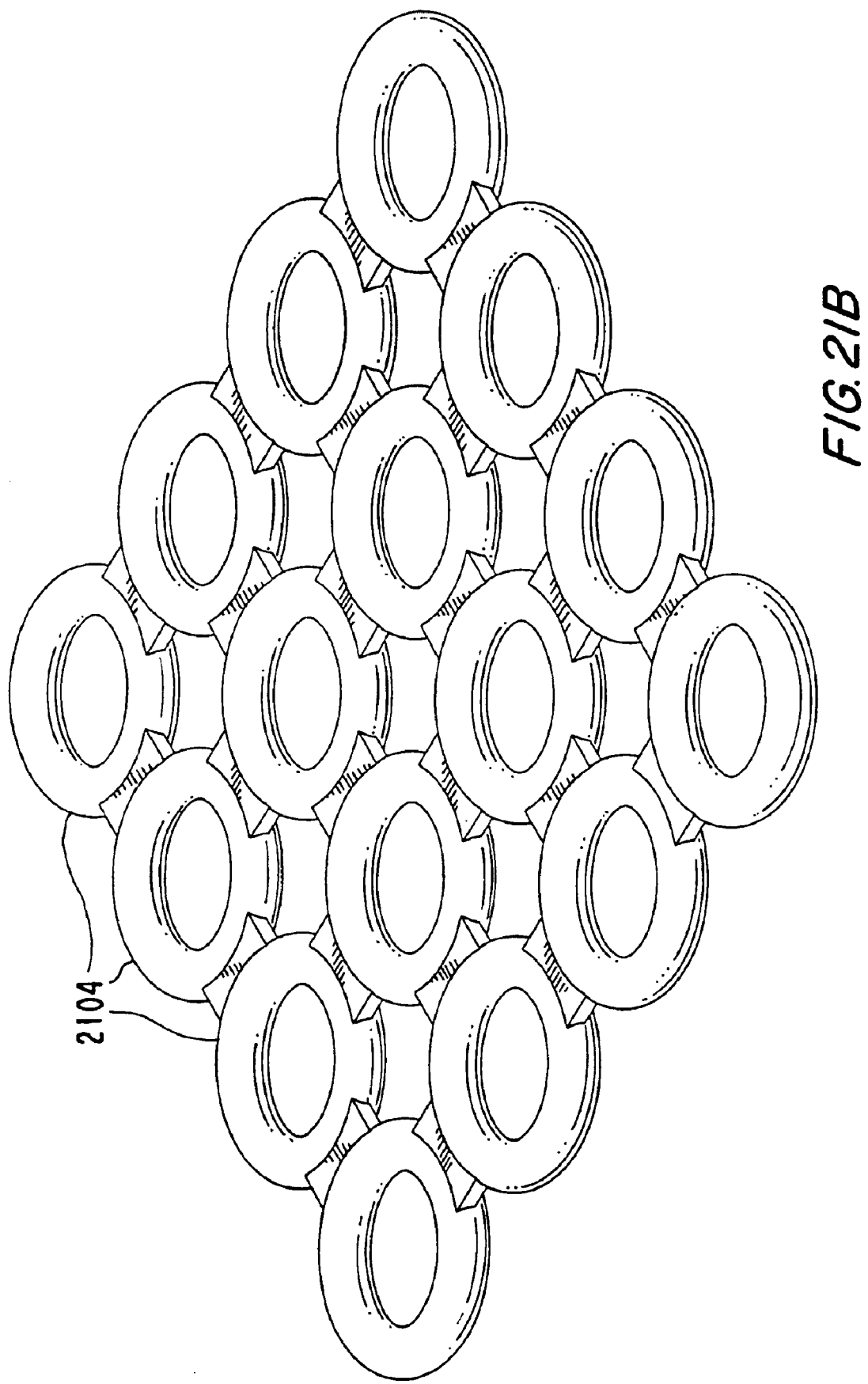
FIG. 21B illustrates a two-dimensional array of o-rings that are used in conjunction with the crystallization assembly of FIG. 21A in accordance with the principles of the present invention.

FIG. 21A illustrates an alternative embodiment of a crystallization assembly 2102 that is designed to permit formation of crystals in accordance with the principles of the present invention. Crystallization assembly 2102 includes similar parts as crystallization assembly 2100 such as reactor base 2160, substrate 2164, and reactor 2168. Not included with crystallization assembly 2102 is pad 2162 and gasket 2166. Instead substrate 2164 is positioned directly on top of reactor base 2160 and o-rings 2104 are added to crystallization assembly 2104. o-rings 2104 may be comprised of a sheet of o-rings (as shown in FIG. 21B) or it they can be a two-dimensional arrays (e.g., 4×4 array of individual o-rings). When crystallization assembly 2102 is assembled, o-rings 2104 are pressed flush against substrate 2164 and reactor 2168 to provide effective isolation of material samples deposited into the crystallization assembly 2102.

Figure 21C:
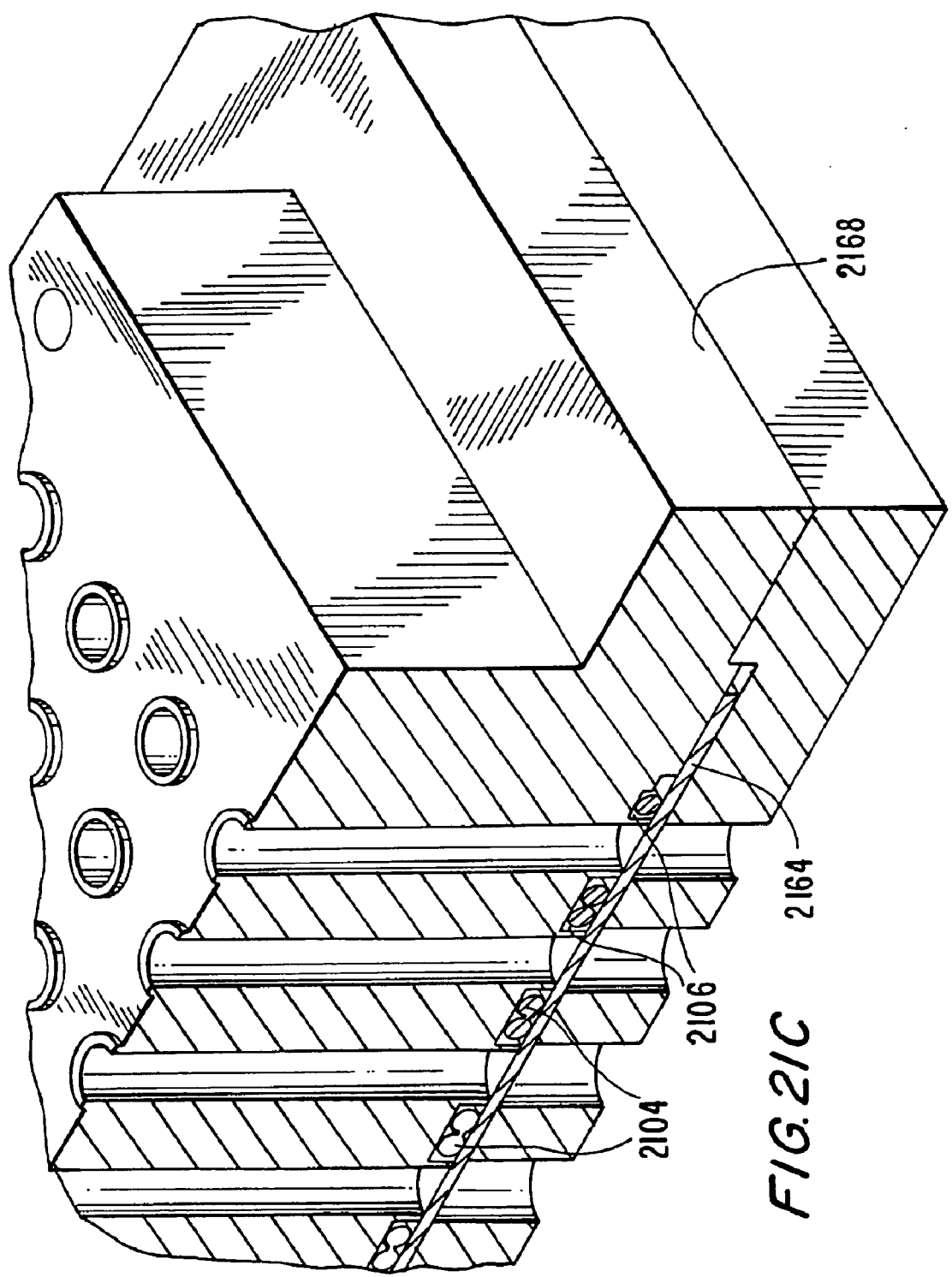
FIG. 21C illustrates a partial cross-sectional view of the crystallization assembly of FIG. 21A which in accordance with the principles of the present invention.

FIG. 21C is a partial cross-sectional view of crystallization assembly 2102 that illustrates how the through-holes of reactor 2168 and respective portions of substrate 2164 are isolated from each other by o-rings 2104. Also shown in FIG. 21C are the wells 2106 in which o-rings 2104 reside. Thus when substrate 2164 is pressed against reactor 2168, o-rings 2106 are pressed against substrate 2164 and wells 2106, thereby providing a substantially airtight seal that isolates each region of the substrate.

When aspirating from or dispensing material into a sealed vial through a septum using a needle or similar device, the accuracy in controlling the volume of material transferred can be affected by the changing volume and pressure within the vial. One solution to this problem has been to use a coaxial needle, which consists of two tubes attached together along their axises. One tube is used to transfer material to or from the vial, and the second tube is used as a vent to equilibrate pressure between the vial interior and the surroundings.

The coaxial needle device presents several shortcomings. Because the two-tube assembly is much larger than a single needle, it will create larger holes when piercing a septum that may not seal properly when the needle is removed. Also, because the tips of the tubes remain at a fixed distance with respect to one another, the range of depths in the vial to which material can be introduced or withdrawn is limited. Dispensing a large amount of material into a deeper vial, for example, may lead to material flowing out of the vent tube if the tip of the vent tube becomes submerged. These shortcomings of the prior art are addressed by the venting needle device described in conjunction with FIGS. 22A and 22B.

Figure 22A:
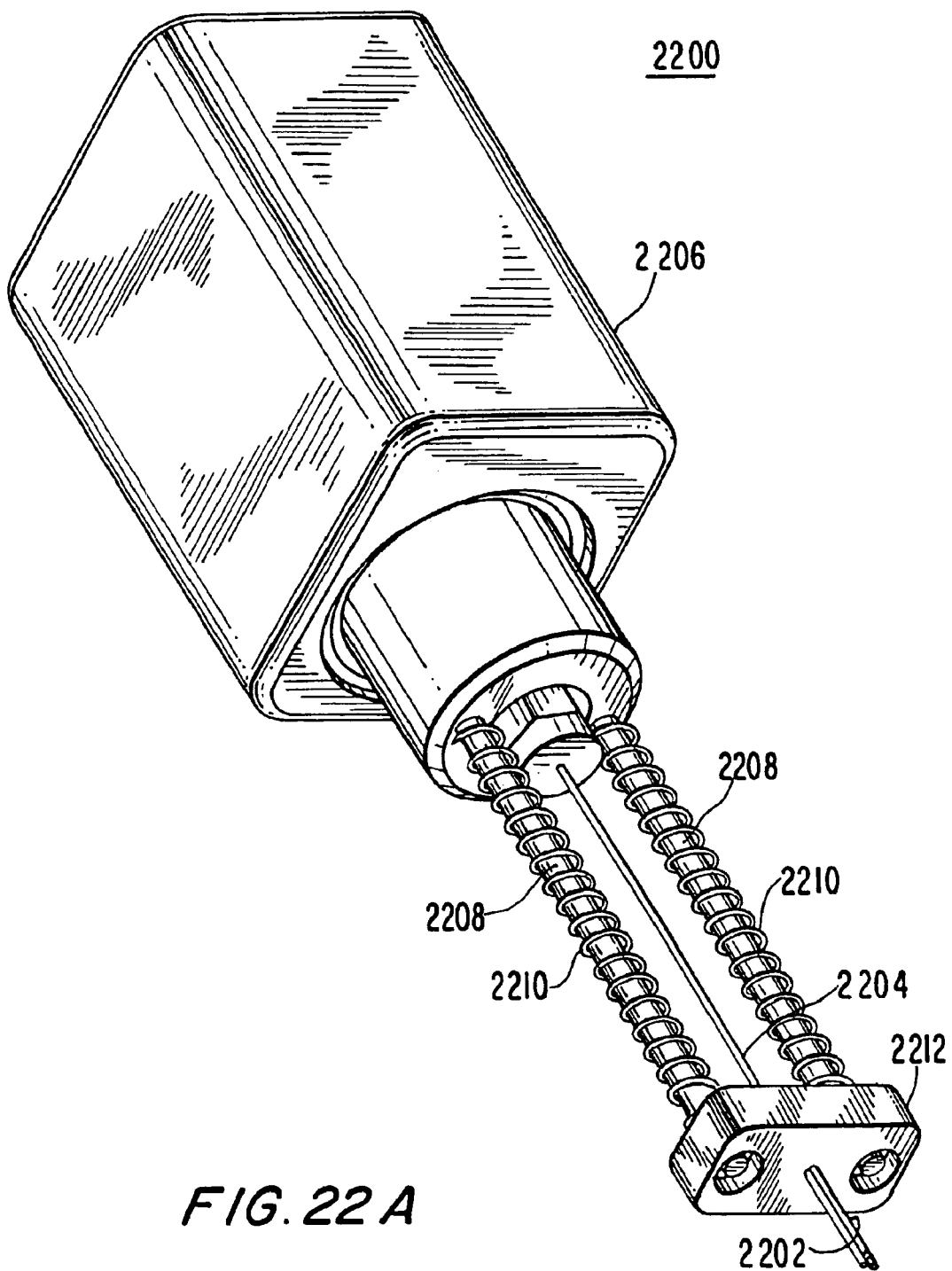
FIG. 22A shows an venting needle assembly in an expanded position in accordance with the principles of the present invention.

FIG. 22A shows a venting needle assembly 2200 that can be used to aspirate from, or dispense materials into, sealed vials or receptacles. Venting needle assembly 2200 comprises venting needle 2202, liquid handling needle 2204, body 2206, guide rods 2208, springs 2210, and guide block 2212. Body 2206 is attached to a liquid handling system (not shown) that controls aspiration and dispensation of liquid through liquid handling needle 2204. Liquid handling needle 2204 extends a fixed distance from body 2206 and passes through movable guide block 2212. Venting needle 2202 also passes through movable guide block 2212, essentially parallel to liquid handling needle 2204, and extends a fixed distance from the lower face of guide block 2212. Guide block 2212 is attached to guide rods 2208, and configured so that it can slide along the central axis of liquid handling needle 2204. Guide rods 2208 are configured to slide into body 2206 when force is applied to the lower face of guide block 2212. Springs 2210 are located on guide rods 2208, between body 2206 and guide block 2212. These springs return guide block 2212 to a fully-extended position, determined by the length of guide rods 2208, when there is no force on the lower face of guide block 2212.

As described above, reactor assembly 1500, filtration assembly 1600, and crystallization assembly 2100 each include a sealing layer (e.g., septum) for isolating each vial or receptacle from each other. For purposes of brevity and clarity, venting needle assembly 2200 is described in conjunction with reactor assembly 1500. Venting needle assembly 2200 is not limited to being used only with reactor assembly 1500, but it can be used with any suitable assembly comprising sealed vials or receptacles. If desired, venting needle assembly 2200 can be used in place of pipette system 2060.

After reactor assembly 1500 is sealed, each vial contains a fixed volume of material. Venting assembly 2200 prevents the pressure from changing when aspirating liquid from or dispensing liquid into a sealed vial, which permits increased accuracy in controlling the volume of material transferred. Venting assembly 2200 accomplishes this by using a dual needle assembly, wherein one needle is used to aspirate/dispense and the other is used to vent the vial.

In a typical material transfer process, venting assembly 2200 is lowered over reactor assembly 1500, either manually or by mechanical means, until the lower surface of guide block 2212 contacts the upper surface of reactor cover 1522. Both venting needle 2202 and liquid handling needle 2204 extend far enough from guide block 2212 to extend through holes 1523 above the vial of interest, and pierce septum sheet 1520 and barrier sheet 1518 (if present). When venting needle 2202 pierces septum sheet 1520 (and barrier sheet 1518, if present), it provides an open passageway between the upper portion of the vial and the surrounding atmosphere, which maintains equilibrium between the pressure in the vial and the ambient pressure (i.e., pressure outside the sealed vial). Thus, when liquid is aspirated from or dispensed into the vial by liquid handling needle 2204, the pressure does not change because venting needle 2202 provides the substantially constant pressure with the vial.

Figure 22B:
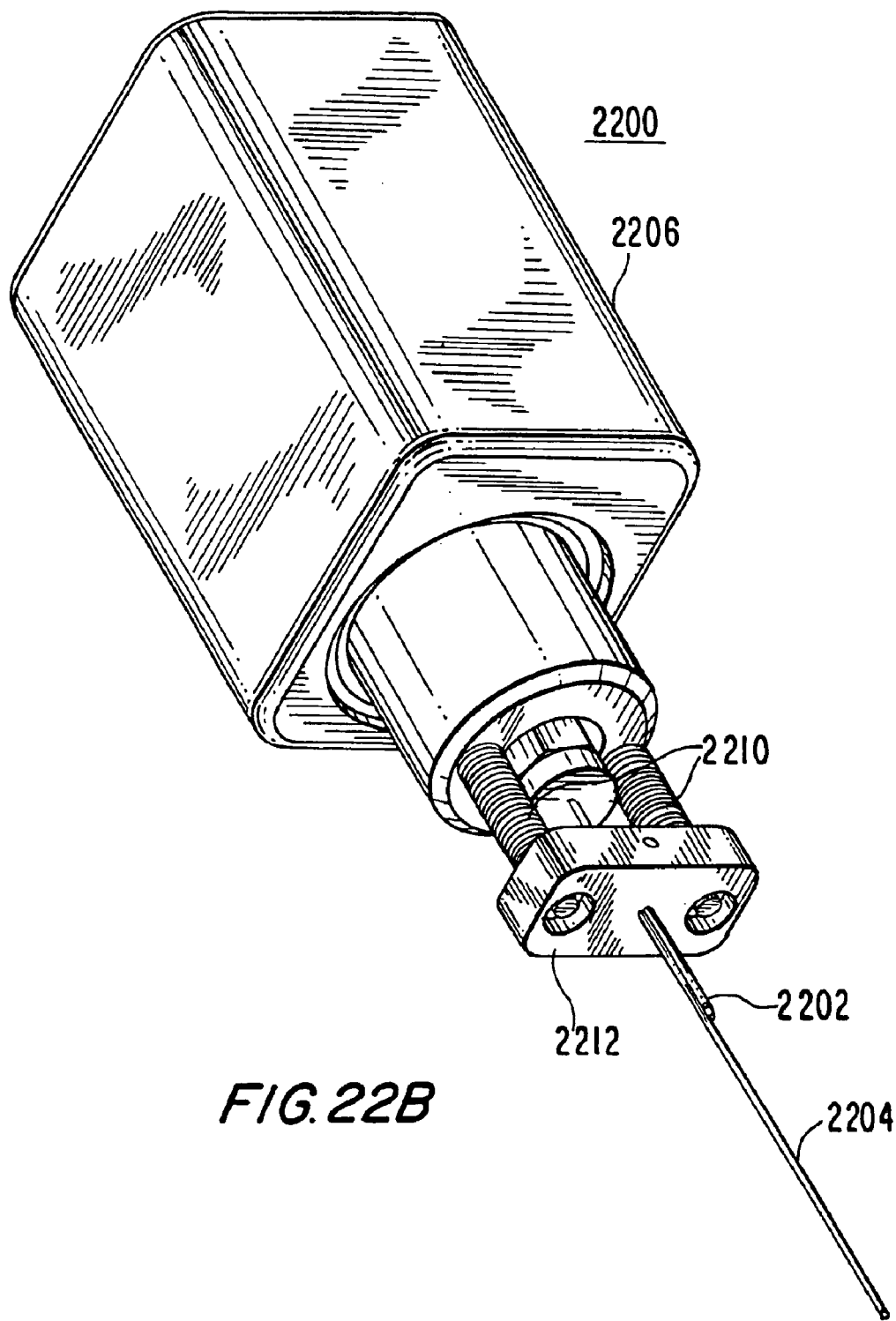
FIG. 22B show a venting needle assembly in a compressed position in accordance with the principles of the present invention.

Body 2206 may be pushed towards the top of reactor assembly 1500 until liquid handling needle 2204, which is attached to body 2206, reaches the desired depth within the vial for dispensing or aspirating a liquid. Body 2206 may contain a mechanism (not shown) the heat liquid handling needle 2204 to a predetermined temperature. As liquid handling needle 2204 extends into the vial, guide rods 2208 slide further into body 2206 and as springs 2210 compress, as shown in FIG. 22B. During this procedure, venting needle 2202 extends a fixed depth into the sealed vial, preferably with the tip of venting needle 2202 located near the top of the vial, above any liquid which may be present. This device thus permits transfer of a liquid to and from vials having different depths while maintaining a venting passage that equilibrates pressure between the interior of the vial and the ambient atmosphere. When the transfer of liquid is complete, body 2206 may be pulled away from reactor assembly 1500, causing liquid handling needle 2204 to withdraw from the vial and springs 2210 to expand until guide block 2212 reaches its fully-extended position, as shown in FIG. 22A. Pulling body 2206 further away from reactor assembly 1500 removes both venting needle 2202 and liquid handling needle 2204 from reactor assembly 1500 through holes 1523. The device may then be inserted into another hole over a different vial and the above procedure repeated.

Temperature is an important parameter in the various formulations, filtration, and crystallization operations that enable salt selection and polymorph production. For example, in some methodologies it is desirable to heat reaction assembly 1500 to dissolve as much drug candidate as possible in the solvent(s). In processes where temperature is important (e.g., during crystallization), any of assemblies 1300, 1500, 1600 or 2100 (shown in FIGS. 13, 15, 16, and 21, respectively) may be placed in an oven, cooler, or other temperature-controlled chamber (such as the Torrey Pines incubator cited herein).

It may be desirable in some processes to have precise control of temperature. One method for controlling the temperature of the assemblies during certain stages of the workflow is shown in FIG. 23, which depicts three-axis robot 2300, having arms 2305 and 2310 and plurality of pumps 2334, situated by work surface 2330. Pumps 2334 are in fluid communication with a solvent or other liquid and in fluid communication with needles 2320 and 2322. Heated block assembly 2350 is positioned on work surface 2330. Heated block assembly 2350 is configured to contain reaction assemblies 1500, filtration assemblies 1600 and those assemblies to assist mixing material samples. It may be desirable to heat filtration assembly 1600 to prevent crystallization during the filtering process. Not shown in FIG. 23 is a magnetic stirring device that can tumble magnetic stirring fleas to agitate materials contained within the assemblies. Also located on work surface 2330 are several temperature-controlled housings 2500. Temperature-controlled housing 2500 is described in more detail in conjunction with the description accompanying FIG. 25. Housing 2500 can contain an assembly such as the reactor assembly 1300, reaction assembly 1500, filtration assembly 1600, or crystallization assembly 2100. FIG. 23 also shows deck assemblies 2370 that hold various assemblies for use in a workflow.

Detailed structure of the temperature-controlled housing is not critical to this invention, and may simply comprise insulated walls with a resistive heater regulated by a thermocouple for temperature control. These types of heaters are sold commercially as the FIREROD™ heaters available from Watlow of St. Louis, Mo.

Figure 24:
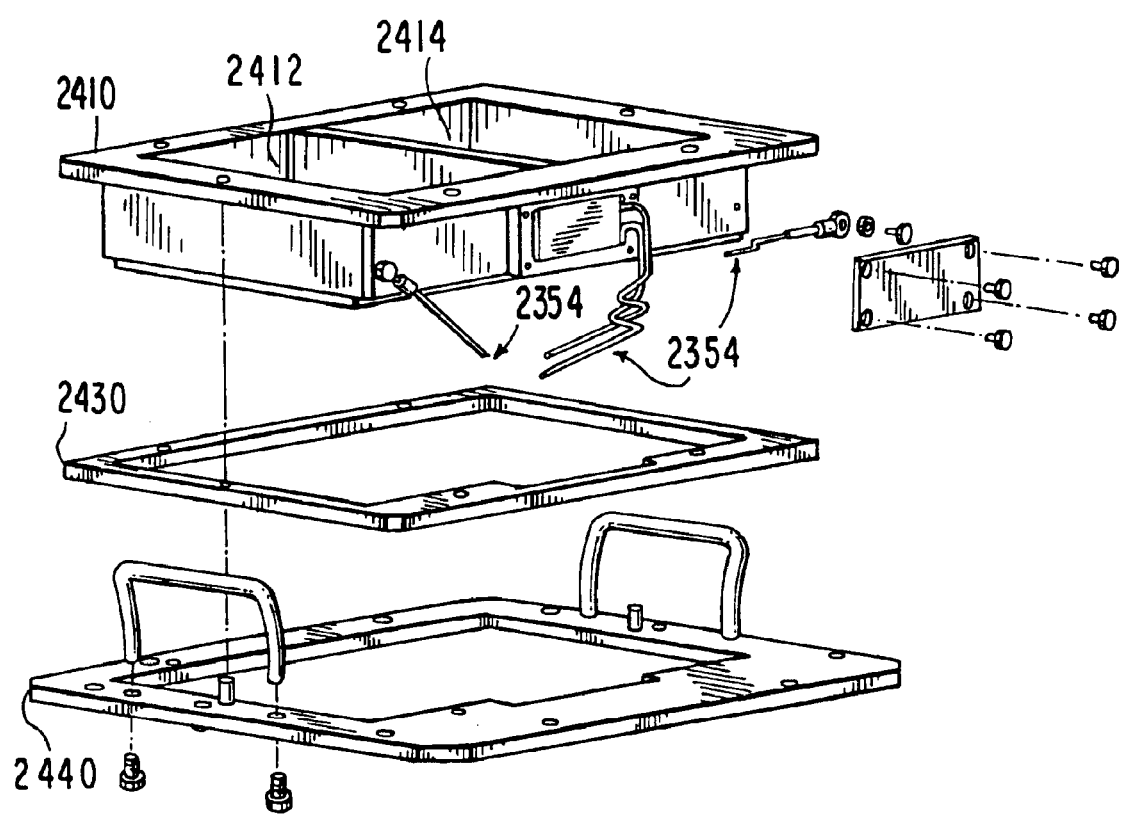
FIG. 24 shows perspective top and bottom views of a temperature-controlled housing in accordance with the principles of the present invention.

FIG. 24 illustrates an exploded view of temperature-controlled housing 2350 shown in FIG. 23. Temperature-controlled housing 2350 includes tub 2410 and tub support fixtures 2430 and 2440. Tub 2410 is constructed from a material (e.g., aluminum) having desired thermal conductive properties. As shown, tub 2410 has pockets 2412 and 2414 for containing an assembly (e.g., reactor assembly 1500 or filtration assembly 1600). Tub 2410 has fluid channels (not shown) in which a fluid or gas is provided to heat or cool the tub. Fluid inlet/outlet ports 2354 provide connections to allow a desired heating or cooling fluid or gas to flow through the channels, thereby heating or cooling an assembly placed in housing 2350. The temperature-controlled housing shown in FIG. 24 may be surrounded by an insulating layer to improve thermal control and stability.

Figure 25:
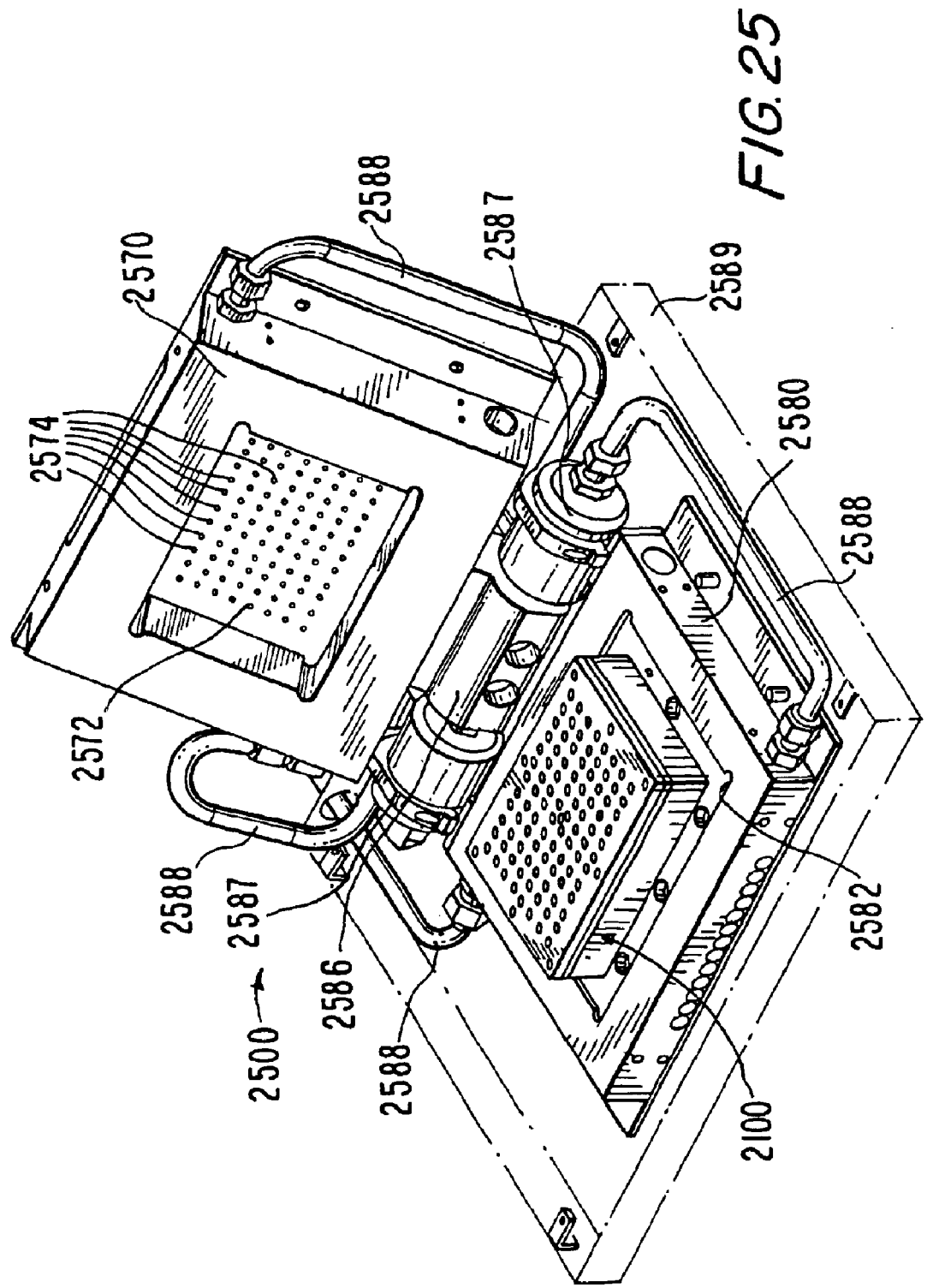
FIG. 25 shows a thermal control chamber in accordance with the principles of the present invention.

Another embodiment that facilitates temperature control of a reactor or assembly is shown in FIG. 25. FIG. 25 illustrates thermal control chamber 2500 having top 2570 and bottom 2580 that mate to form an enclosure. Top 2570 has cavity 2572 therein and bottom 2580 has cavity 2582 therein, which together define the enclosure. Cavity 2572 is preferably sized to accommodate at least one of the assemblies 1300, 1500, 1600, or 2100 (shown in FIGS. 13, 15, 16, and 21, respectively).

In a preferred embodiment, top 2570 has holes 2574 to allow for communication through top 2570, (e.g., by a needle, cannula or pipette), for aspirating or dispensing liquids into the regions, vials or wells of the assembly in the cavity when top 2570 and bottom 2580 are closed together. A fluid that heats or cools the thermal control chamber may flow through top 2570 and/or bottom 2580. The fluid flow preferably maintains a specific temperature substantially throughout the assembly contained therein. A temperature variation of about 2° C. across the enclosed assembly is generally acceptable, but a temperature variation of less than about 1° C. is desirable. Top 2570 and bottom 2580 are made of a material (e.g., aluminum) with good heat transfer properties. Suitable fluids with well-characterized thermophysical properties (e.g., water, glycol, etc.) flow through top 2570 and/or bottom 2580 for heating or cooling.

Thermal control chamber 2500 can apply a thermal profile to the assembly contained therein. The thermal profile may, for example, subject the assembly to a range of temperatures that vary with time or to a temperature that is substantially the same for the chosen time period throughout the thermal control chamber. For example, the temperature of the thermal control chamber may ramp up to a predetermined temperature a specified rate, stay at the predetermined temperature for fixed period of time, and then ramp down to ambient temperature after a specified period of time.

FIG. 25 shows thermal control chamber 2500 wherein top 2570 and bottom 2580 are connected by hinge 2586 that allows the top and bottom to pivot with respect to each other. This configuration allows for easier alignment and fastening of the top and bottom of the thermal control chamber that contains an assembly such as crystallization assembly 2100 (shown in FIG. 21). When top 2570 is pivoted about hinge 2586, it aligns with bottom 2580 so that cavities 2572 and 2582 meet to enclose the assembly within the chamber.

A typical fluid flow path can occur as follows. Thermal fluid enters either top 2570 or bottom 2580 first and then flows through the inlet, transverse, and outlet conduits. Then fluid passes through external conduit 2588 and into the other half of the chamber where the flow pattern is repeated. Thus, if the thermal fluid enters top 2570 first, it will flow through the top, exit the top and be channeled into bottom 2580, flow through the bottom, and then exit the bottom. The flow direction may also be reversed if desired, so the thermal fluid enters the bottom before the top. Rotating fluid transfer hinge 2587 may be provided on either side of hinge 2586 which allows top 2570 and bottom 2580 to pivot with respect to each other without adjusting external conduits 2588. This function could also be accomplished with flexible external conduits and a loop, however, the arrangement shown in FIG. 25 is a preferred embodiment as it avoids the need for flexible tubing.

Although not shown in FIG. 25, chamber 2500 has a window that provides a means for a device to monitor the arrays of material samples contained within chamber 2590. A glass sheet is coupled to this window with a gasket. Preferably a purge of dry gas (e.g., nitrogen) is provided to prevent condensation from developing when chamber 2590 cools. This ensures that the monitoring equipment has an unobstructed access to the material samples. For example, in-situ measuring requires an unobstructed access to monitor the materials samples that are subjected to crystallization conditions.

Figure 26:
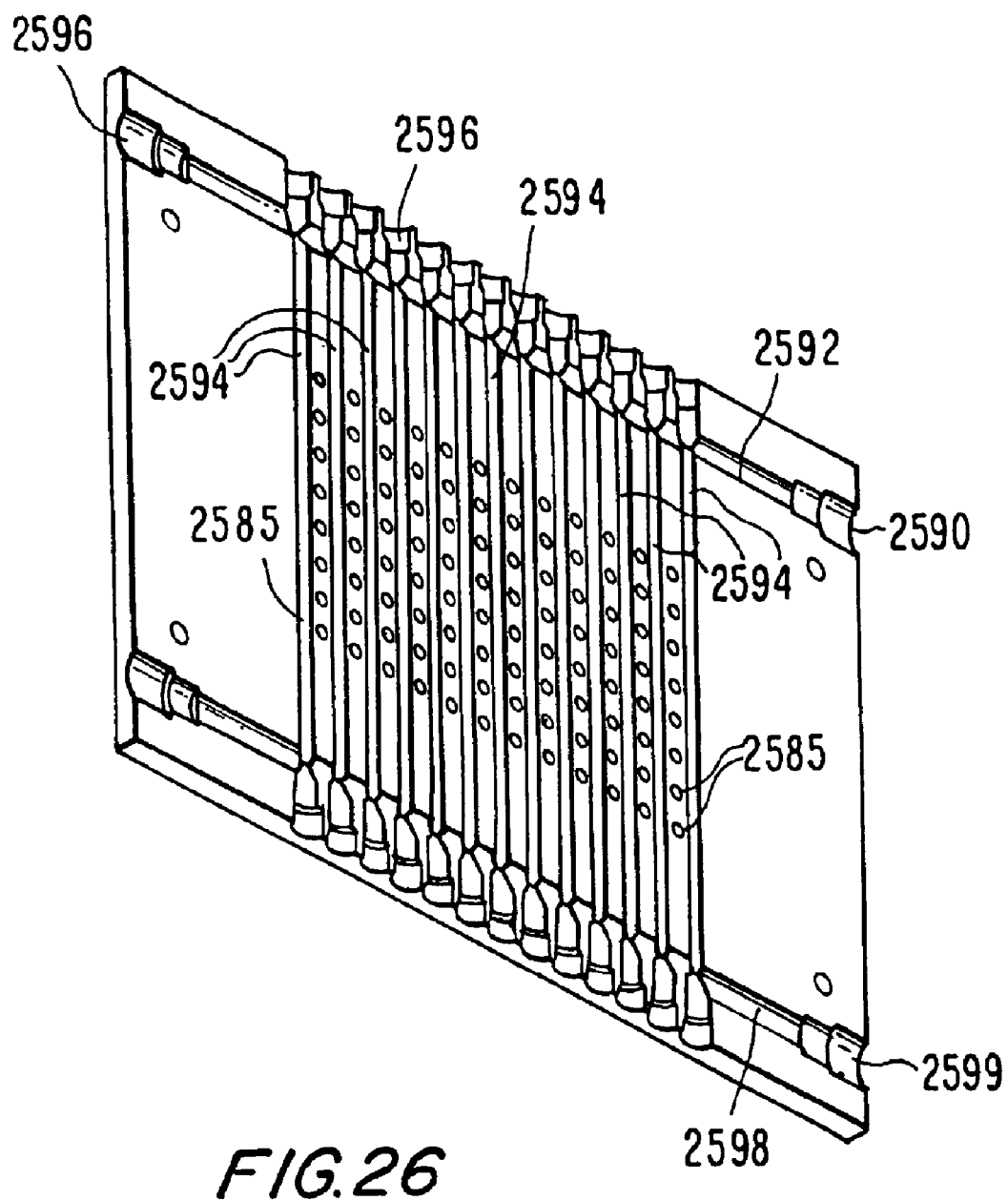
FIG. 26 shows a three dimensional view of fluid channels of the temperature-controlled housing of FIG. 25 in accordance with the principles of the present invention.

The structure that facilitates fluid flow is shown in more detail in FIG. 26, which depicts a cutaway view of the channels that define the fluid path in top 2570 and/or bottom 2580 of thermal control chamber 2500. The heating/cooling fluid enters via fluid inlet 2590, which leads to inlet conduit 2592. A plurality of transverse conduits 2594 lead from inlet conduit 2592 to outlet conduit 2598 and to fluid outlet 2599. Inlet conduit 2592 and outlet conduit 2598 are preferably larger in diameter than the transverse conduits 2594 so that the fluid entering inlet 2590 will flow uniformly through all of transverse conduits 2594. This flow pattern for the heating/cooling fluid assists in uniform heating or cooling of control chamber 2500

Transverse conduits 2594 pass on either side of holes 2574, if present. Larger conduits 2592 and 2598 may be formed by drilling holes through a block and then plugging one end of each with a large plug 2595 for ease of manufacture. Smaller transverse conduits 2594 can be formed in a similar manner, with both ends of the drilled holes capped off by small plugs 2596.

In operation, a thermal fluid such as water, glycol, or glycerol is transported from a uniform temperature reservoir (not shown) to top 2570 or bottom 2580 of thermal control chamber 2500 through a fluid line using a constant or variable-speed pump. The thermal fluid enters inlet conduit 2592 through inlet port 2590. The thermal fluid flows through transverse conduits 2594 and into outlet conduit 2598. The thermal fluid then exits through fluid outlet 2599, where it then returns to the reservoir or is routed through another top or bottom.

A heat pump or other device may be used to regulate the temperature of the thermal fluid in the reservoir by adding or removing heat through a heat transfer coil located in the reservoir. In one embodiment, a processor receives signals from temperature sensors located in the reservoir, and adjusts the amount of heat added to or removed from the thermal fluid through the coil. One or more temperature sensors (not shown) may also be mounted in the top or bottom of the thermal control chamber and connected to the processor. Temperature control can then be achieved by varying both the temperature of the thermal fluid in the reservoir and the flow rate through the conduits. To adjust the flow rate of thermal fluid through the fluid flow system, the processor communicates with a valve located in a reservoir outlet line. Various parts of the system can also be insulated to improve temperature control and stability.

FIG. 27 shows a cross-sectional view of thermal control chamber 2500 with crystallization assembly 2100 enclosed therein. This view shows insulation 2591 can be packaged with thermal control chamber. Cross-sectional view 2700 illustrates additional details of the components just described above in conjunction with FIGS. 21, 22, 25, and 26.

Determining the melting point of salts and drug candidates is an important characterization technique for the screening process. In particular, differences in melting point among crystals or amorphous precipitates of a given compound comprise one of the best indicators for determining the existence of polymorphs.

In one embodiment of the present invention, a melting point station is employed to determine the melting point of the solid material contained in each region of an array following salt formation, precipitation, crystallization, or other similar procedure in the process. Melting points of various materials may be determined by controllably raising the temperature of the substrate containing the array while monitoring the birefringence image (if present) of one or more regions of the array. The temperature at which the birefringence image from a region of the array disappears indicates a transition from the solid to the liquid state. This transition state corresponds to the melting point of the solid matter (generally crystals or amorphous solid) in that region.

Generally, this measurement is based on melting point measurements known in other fields of endeavor. See, e.g., Magill, J. H. "A new method for following rapid rates of crystallization. II. Isotactic Polypropylene." *Polymer* 1962, 3, 35–42; Ding, Z. and Spruiell, J. E. "An experimental-method for studying nonisothermal crystallization of polymers at high cooling rates", *J. of App. Polymer Science Part B—Polymer Physics,* 1996, 34, 2783–2804; Garetz, B. A., et al., "Birefringence and diffraction of light in ordered block-copolymer materials" *Macromolecules,* 1993, 26, 3151–3155; Carlson, E. D. et al. "Mechanical and Thermal Properties of Elastomeric Polypropylene" *Macromolecules,* (1998), 31(16), 5343–5351; and Carlson, Eric David, "A rheo-optical investigation of the relaxation and crystallization behavior of stereoblock polypropylene synthesized from 2-arylindene metallocene catalysts," Stanford Ph.D. Dissertation (1998); each of which is incorporated by reference.

A melting point apparatus designed to determine melting points of an array of solids on a substrate is shown in FIG. 28. Melting point apparatus 2800 determines the melting points of an array of samples by monitoring the optical properties of the samples for phase transitions. Melting point apparatus 2800 can also measure recrystallization kinetics during thermal cycling. Melting point apparatus 2800 can use a light scattering or birefringence measuring technique to determine when a sample transitions from a crystalline structure to an amorphous liquid. When performing birefringence measuring, a transmissive or a reflective technique can be used.

Apparatus 2800 detects the melting point of material samples as follows. First, a sample array is prepared via crystallization. Those of skill in the art will appreciate that a sample array can be prepared by other methods other than crystallization. For example, an evaporation or a precipitation method can be used. It will also be appreciated that solid materials (e.g., may be prepared by hand or automatically by a robot. The sample array may be contained on a glass slide (e.g., universal substrate) or other transparent material that is placed into a carrier block. If desired, the carrier block can be covered to contain any moisture that forms from products of material decomposition such as condensation, solvent vapors, etc. Finally, the carrier block is placed into a temperature chamber such as thermal control chamber 2500 or is placed within two insulated plates (FIGS. 28A and 28B), which form a quasi-isothermal block.

After the material samples are placed in the temperature chamber, an individual light source and a detector are aligned to each material sample in the array. Operating in transmission mode, each light source transmits a light signal through a material sample. The light source can any suitable device such as, for example, light emitting diodes, lasers, or incandescent lights. Collimated, polarized, intense, monochromatic light is preferable for operation, but weak light (e.g., incandescent light) can also be used. The light signal can comprise a wavelength ranging between about 300–2000 nanometers (nm). If desired, a single light source can be distributed to each material sample by, for example, a fiber-optic bundle, a telecentric lens, a telescope, collimating optics, or other similar apparatus. Alternatively, a single light source or an array of light sources may be moved across each material sample to illuminate a single material or a row of such materials at a time. Persons skilled in the art will appreciate that any suitable arrangement of light sources can be used to provided light-scattering or birefringence testing.

If a reflective technique is used, the light path does not pass through the material samples. Rather, the reflection of light off a crystalline structure is detected. This technique is described in detail in conjunction with in-situ measuring assembly 3000 of FIG. 30. The reflective technique operates generally as follows. Light emitted from a light source passes through a first polarizer, then it reaches a beam splitter that redirects the light towards a material sample. If desired, the light can be "pre-polarized" (e.g., a laser) so that a first polarizer is not needed. Light reflected from the material sample passes back to the beam splitter, but passed through the beam splitter. If the light signal has been altered (e.g., polarized) by the material sample, then it may pass through a second polarizer that is rotated 90° from the first polarizer and detected by a detector.

Light provided by the light source first passes through a polarizing filter, then through the material sample, through a second polarizing filter that is oriented at 90° with respect to the first polarizing filter. If the material sample does not contain a crystalline structure, then the light signal will be extinguished by the second polarizing filter, thereby preventing a detector from detecting the light signal. If the material sample contains a crystalline structure, however, the crystal will rotate the polarization of the light, thereby allowing some of the light to pass through the second polarization filter. Any light that passes through the second polarization filter is detected by the light detector.

Various detection methods can be used to detect light emitted by the light source(s). Individual detectors such as photodetectors (e.g., silicon photodiode, photovoltaic cell, etc.) may be positioned with respect to each material sample. Each photodetector is connected to a computer (e.g., computer 110) that monitors the output of each detector. Based on the output signals of the photodetectors, the computer can determine at what temperature a crystalline structure melts. Likewise, if a detector such as a camera, a charge-coupled device (CCD) a digital camera, or a video camera is used to detect phase transitions, aa computer may register the transitions and calculate the melting point temperature.

Initially, before the chamber begins to heat the material samples, each detector can ascertain whether a crystal structure is present. Because each detector is connected to a computer or other data logging device, each detector can constantly monitor each material sample. This is useful because when the material samples are heated, they eventually melt, and the detectors detect this phase transition. When the crystal melts, it becomes amorphous, and light is no longer able to pass through the second polarizing filter. When a detector no longer detects a previously existing light signal, it is at this temperature that the crystal has melted.

The temperature of the material samples are ramped up at user defined rate to a user defined maximum temperature. The rate of temperature increase is precisely controlled and uniform throughout the material samples. This enables apparatus 2800 to accurately measure melting point temperatures. Alternatively, the temperature can be step up in controlled increments. Furthermore, the temperature of each material sample can be controlled individually.

The above discussion was primarily directed to birefringence testing, but the present invention is not limited to such. Different birefringence testing can be performed. For example, the polarization angle of one or both polarization plates can be modulated. The frequency of the light can be modulated. In another approach, the above mentioned light scattering approach can be implemented by removing the polarizer plates. Light scattering, for example, is another testing method that can be implemented to detect crystalline structures contained in the sample array.

Apparatus 2800 includes two main assemblies: thermal platform 2810 that can support and controllably heat and cool an array (i.e., a substrate containing samples), and opto-mechanical platform 2830 that permits simultaneous optical imaging of some or all of the regions on the array.

Thermal platform 2810 includes thermal platform top 2812 and thermal platform base 2814, which when assembled together create cavity 2816 that supports a substrate or suitable testing platform (e.g., a carrier plate). Thermal platform 2810 is made of any suitable material that has high thermal conductivity such as aluminum, aluminum alloys, or copper. Other materials such as indium, lead, tin, or silver may be used to form part or all of thermal platform 2810 to enhance conductivity and improve temperature uniformity. The substrate may be constructed from borosilicate glass, or is a Zinnser™ plate, or is made of some other optically transparent or translucent material. The substrate is preferably positioned to provide optimal thermal conduction with thermal platform 2810. For example, substrate 2164 (FIG. 21) can be placed in thermal platform 2810.

Figure 28A:
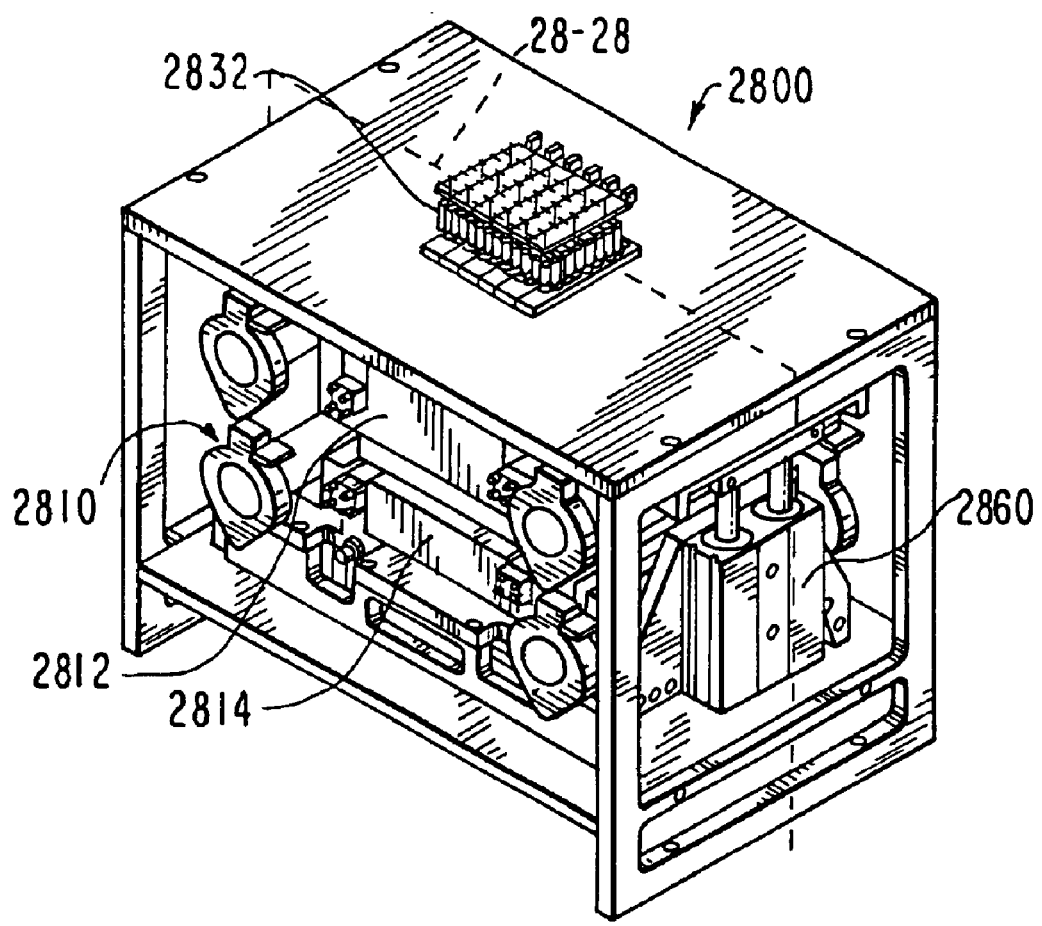
FIG. 28A shows an isometric view of the apparatus of FIG. 28 in accordance with the principles of the present invention.
Figure 28B:
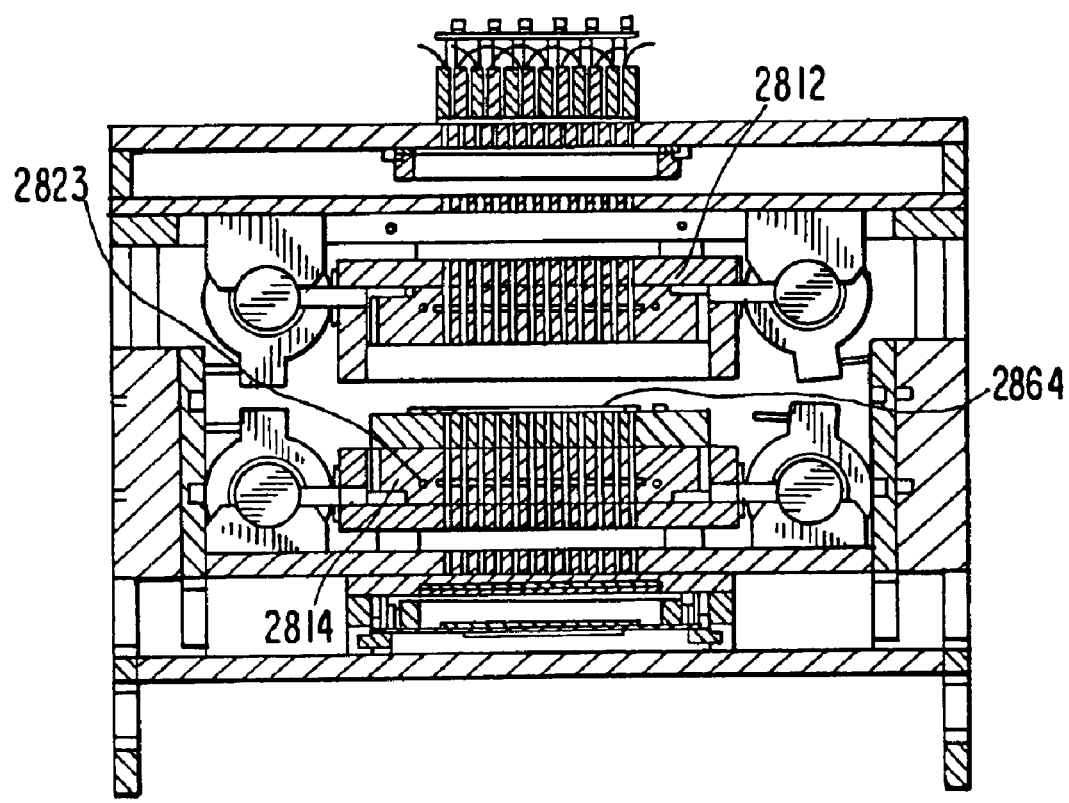
FIG. 28B shows a cross-sectional view taken along the line 28—28 of the apparatus in FIG. 28A in accordance with the principles of the present invention.

Thermal platform 2810 is shown in detail in FIGS. 28A and 28B. FIG. 28A shows an isometric view of melting point apparatus 2800 (computer not shown) that shows thermal platform 2810 and light source array 2832. As described above, thermal platform 2810 includes thermal platform top 2812 and thermal platform bottom 2814, which are also shown in FIG. 28A. Thermal platform 2810 is shown to be in an OPEN position. That is, pneumatic press 2860 is in a position such that thermal platform top 2812 and thermal platform bottom 2814 are not pressed against each other. Pneumatic press 2860 is used to assist opening and closing thermal platform 2810.

FIG. 28B shows a cross-sectional view of the FIG. 28A taken along line 28—28. Thermal platform 2810 is also shown to be in the OPEN position. One skilled in the art will appreciate that when thermal platform 2810 is closed, thermal platform top 2812 and thermal platform bottom 2814 are pressed flush against one another to fully enclose substrate 2864 contained therein. Preferably, a glass cover sheet is placed over substrate 2864 to contain any products of composition (e.g., condensation, out-gassing).

Both thermal platform top 2812 and thermal platform bottom 2814 have through holes 2823 in which resistive heating elements can be contained. Theses resistive heating elements, which are described in more detail below, provide a mechanism for heating substrate 2864 at a controlled rate while maintaining a uniform temperature distribution.

Referring back to FIG. 28, thermal platform base 2814 is designed to be heated by elements attached to or embedded within thermal platform base 2814. In a preferred embodiment, thermal platform base 2814 contains channels (not shown) that are similar to conduits 2592, 2594, and 2598 in FIG. 26. A thermal fluid from a reservoir (not shown) can flow through these channels to heat the substrate in a controlled manner, as described above. A thermal fluid at a lower temperature can also flow through these channels or an adjacent set of such channels to cool thermal platform base 2814.

Alternatively, one or more resistive heating elements 2822 may be attached to or embedded in thermal platform base 2814 to provide a mechanism for heating thermal platform base 2814. Resistive heating elements 2822 may include, for example, wire-wound resistive heaters, thermoelectric devices (e.g., peltier junctions) and thin- or thick-film resistor heaters. Resistive heating elements 2822 may be embedded or attached to thermal platform base 2814 to permit improved control of thermal uniformity or specific temperature profiles in thermal platform 2810. Different resistive heating elements 2822 may be capable of distributing different quantities of heat (i.e., the power consumption may vary). various resistive heating elements 2822 that have different power consumption may be placed strategically on thermal platform top 2812 and thermal platform base 2814 to promote uniform temperature distribution. A combination of channels for heating/cooling by flow of thermal fluid and resistive heating elements 2822 may also be used. Those skilled in the art will recognize that other methods of heating or cooling thermal platform base 2814 in a controlled manner may also be used.

Another method for heating or cooling the material samples is to subject the samples to a gaseous bath such as that provided by a convection oven. Yet another method is to heat each material sample individually, or in a serial fashion with individual heaters.

Thermal platform 2810 may also have one or more embedded or attached thermal sensors 2820 that can be used in connection with appropriate external equipment (e.g., datalogger, computer, etc.) to monitor the temperature of the platform. These sensors may be in the top or bottom of platform 2810, and may include one or more of the following: thermocouples, resistance temperature detectors (RTD's), or semiconductor-based thermistors. One or more of these sensors may be located either in the top, in the bottom, or in both the top and bottom of thermal platform 2810. Signals obtained from these sensors are preferably connected to a computer (e.g., computer 110 of FIG. 1) to permit automated monitoring and control of the temperature. The sensor signals can be processed using appropriate control software to regulate current in resistive heater elements, if present, or to regulate the temperature and flow rates of thermal fluids in channels, if present, or to provide more accurate control of both heating and cooling rates in thermal platform 2810.

Various sensor arrangements can be used to accurately determine the melting point of crystalline structures. The temperature of each material sample may be individually measured, interpolated from an array of neighboring sensor, or extrapolated from a single sensor. Sensors may be located on thermal platform 2810 or some other heat transfer medium (e.g., convection oven). Sensors may be located directly on the sample substrate such as directly below a well containing a material sample.

Thermal platform 2810 implements a heating system that is capable of raising the temperature of thermal 2810 platform and an enclosed substrate from ambient temperatures to a user defined temperature. at a user defined rate. For example, the user can select the maximum temperature to be about 200° C., 280° C., 300° C., or any other suitable temperature. The rate at which the temperature can be increased or decreased can also be set by the user. For example, a user may set the rate of temperature deviation at about 0.5° C. per minute, 1.0° C. per minute, 2.0° C. per minute, or some other suitable temperature variation. Persons skilled in the art will appreciate that thermal platform 2810 may heat or cool an enclosed substrate to any suitable temperature. In addition, thermal platform 2810 may heat or cool an enclosed substrate at any rate. Moreover, thermal platform 2810 may cycle the temperature to perform re-crystallization studies.

Thermal platform top 2812 is constructed with an array of upper optical holes 2813 that corresponds to an array of lower optical holes 2815 of thermal platform base 2814. Holes 2813 and 2815 are similar to holes 2574 in thermal control chamber 2560 shown in FIG. 25, are located above and below some or all of the regions on a substrate when the substrate is placed in thermal platform 2810. Holes 2813 and 2815 are associated with a region of a substrate are constructed to provide an optical pathway that passes through thermal platform 2810. This optical path is preferably in a direction substantially perpendicular to the enclosed substrate, and intersects at least a portion of the region of the substrate associated with the upper and lower holes.

Opto-mechanical platform 2830 in FIG. 28 includes light source array 2832 and sensor array 2834 arranged on opposite sides of thermal platform 2810. Opto-mechanical platform 2830 may be similar to that taught in U.S. Pat. No. 6,157,449, which is incorporated herein by reference in its entirety. Light source array 2832 may includes one or more laser diodes, light emitting diodes (LEDs), or other controlled light sources 2833. Alternatively this array may comprise one or more light sources that are segregated by mirrors or prisms to form an array of beams. Sensor array 2834 includes a group of sensors 2835 such as photo diodes, charge-coupled devices (CCDs) or other optical sensors, which are preferably positioned on the side of thermal platform 2810 that is opposite light source array 2832. First polarizing sheet 2840, typically a commercially-available polarizing filter or polarizing mirror, is mounted between the light source array and the thermal platform. Second polarizing sheet 2842 is mounted between thermal platform 2810 and sensor array 2834 at a cross-polarizing orientation of approximately 90° with respect to first polarizing sheet 2840.

If desired, the orientation of second polarizing sheet 2842 may not be positioned exactly at 90° with respect to first polarizing sheet 2840. Rather, second polarizing sheet 2842 may be positioned a few degrees (e.g., 1–5 degrees) above or below a perfect 90° cross-polarization. This slight deviation from perfect cross-polarization prevents extinction of unaltered light signals provided by a light source. But this deviation still allows for detecting changes in crystals using a birefringence monitoring technique and/or a light scattering monitoring technique.

Light source array 2832, light sensor array 2834, polarizing sheets 2840 and 2842, and thermal platform 2810 are configured so that optical path 2850 exists between one or more of the light sources and opposing light sensors that passes through polarizing sheet 2840, thermal platform 2810 including a region on the substrate mounted therein, and second polarizing sheet 2842. The orientation of second polarizing sheet 2842 filters or blocks nearly all of the light that originates from light source array 2832 and traverses optical path 2850 without passing through any materials. Thus, if light passing through a material and has its polarization changed, it may pass through second polarizing sheet 2842 and be received by light sensor array 2834. If this occurs, then the birefringence image of the material (e.g., crystal) may be obtained.

The melting point apparatus described above permits detection of phase transitions, including the solid-to-liquid transformation, that may occur on individual wells or regions of a substrate. A substrate containing deposits of candidate salts, neutrals, solid precipitates, or filtrates to be characterized may be located on one or more regions of the substrate. This substrate may be placed into thermal platform 2812, which in turn is placed into opto-mechanical platform 2830 to perform optical scanning. Thermal platform 2810 is configured so upper and lower optical holes 2813 and 2815 align with optical paths 2850. This operation may be performed manually or automatically using robot arms to provide for a more fully automated procedure which reduces the possibility of errors in handling the samples.

The temperature of the thermal platform containing the substrate and one or more material samples is then increased at a defined rate and monitored. In a preferred embodiment, one or more temperature sensors in contact with the substrate are used to provide real-time temperature data to an external data collection and processing device such as computer (e.g., computer 110 of FIG. 1). The computer may also be interfaced to the heating/cooling system described above to provide feedback for better temperature control. In a typical process, the temperature of the thermal platform is raised from ambient temperatures to about 200° C., or from ambient temperatures to about 300° C., at a rate of about 0.5° C. per minute, 1.0° C. per minute, 2.0° C. per minute, or any other suitable rate.

The optical signal received by each light sensor 2835 is monitored by a computer in real time. Transformation of a material candidate or other material on a region of the substrate from a solid to a liquid state will generally cause an abrupt decrease in the amount of light reaching the sensor that lies on the optical path passing through that region or well. This effect arises primarily because amorphous liquids have a much weaker "birefringence polarizing effect" on light than solid crystalline materials. The temperature at which the optical signal associated with a given region or well of the substrate changes can then be detected by the computer and recorded, yielding a measure of the melting point of that particular sample. The entire array of materials on the substrate or any subset thereof may be characterized for melting points during a single thermal ramp-up cycle, as the individual sensor corresponding to each region will provide a distinct signal as the temperature of the entire substrate reaches the melting point associated with the material located at said region.

Slower rates of temperature increase tend to yield more accurate melting point values by reducing transient errors associated with finite heat transfer delays between the thermal platform and the substrate. The actual ramp-up rate chosen for a given measurement set will generally reflect a compromise between accuracy and overall time required to complete the set.

In the case of polymorphs, it is possible to measure more than simple melting points with this test, inter-polymorph transitions may also be observed. Inter-polymorph transitions may include transitions from one polymorph to another (e.g., solid to solid transitions). In this case, a detectable shift in the intensity of filtered light reaching a sensor (where the change may be an increase or a decrease) would indicate a transition from one solid form to another, particularly if the same region of the substrate undergoes a melting transformation at some later time and higher temperature during the set of measurements.

Figure 30:
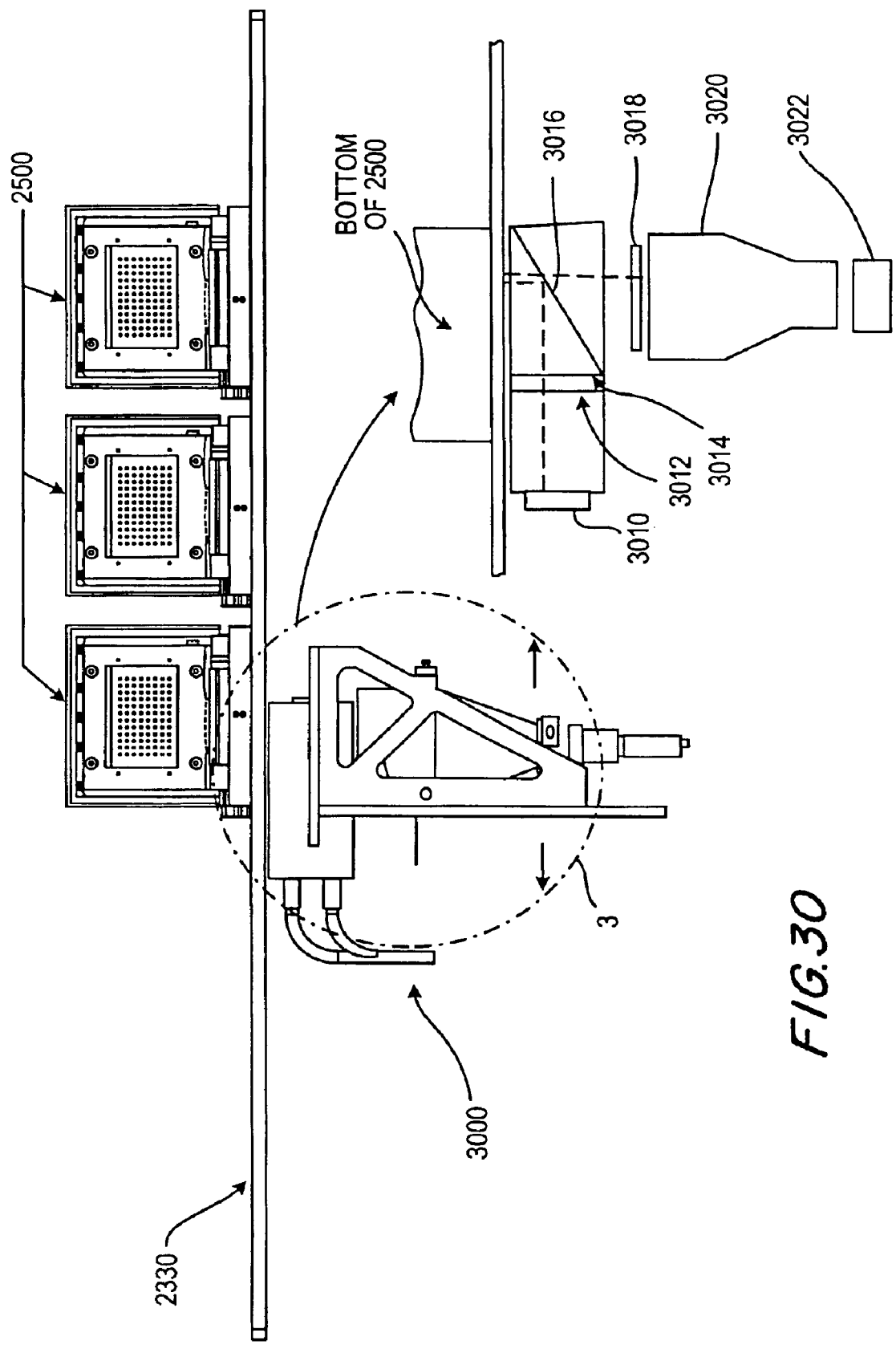
FIG. 30 shows an apparatus for performing in-situ measurement in accordance with the principles of the present invention.

FIG. 30 illustrates an in-situ monitoring assembly 3000, which can be used to observe crystallization of library members in accordance with the principles of the present invention. As shown, in-situ monitoring assembly 3000 is positioned below work surface 2330 of FIG. 23, which provides support for devices such as thermal control chambers 2500. In this configuration, work surface 2330 has optical pathways leading to the regions (or vessels) where materials are being formed so that in-situ monitoring device 3000 can perform measurements. As further shown, assembly 3000 is capable of moving horizontally with respect to work surface 2330 for positioning under various thermal control chambers 2500. Assembly 3000 is positioned beneath one of thermal control chambers 2500 to perform in-situ measurement. If desired, assembly 3000 can be positioned above work surface 2330 or part of work surface 2330. In-situ measurements may provide an advance indication of library members that have formed crystal structures. This information can be provided, for example, as input for determining which library members should be selected for testing when the crystallization step is complete.

Also shown in FIG. 30 is an enlarged cross-sectional view taken from circle 3. The cross-sectional view shows how in-situ monitoring can be accomplished using light source 3010, diffuser 3012, polarizer 3014, light beam splitter 3016, second polarizer 3018, lens 3020, and detector 3022. When assembly 3000 is it preferably positioned such that the crystallization assembly (e.g., crystallization assembly 2100) contained within thermal control chamber 2500 is within full view of lens 3020. This enables assembly 3000 to scan two or more library members simultaneously. If lens 3020 is a telescentric lens, then light received by the lens is able to transmit the light in parallel to detector 3022, thereby reducing image distortion caused by conventional lenses. When detector 3022 captures the light signal, it is able to provide a relatively clear picture of the material samples. Detector 3022 can be, for example, a camera, a digital camera, a television camera, a charge-coupled device.

Assembly 3000 operates on substantially the same principles as that previously described in conjunction with the birefringence testing mechanism of FIG. 28. Instead of a transmission scanning technique, however, assembly 3000 uses a reflective optical scanning technique that detects reflection of light off a crystalline structure. The reflective technique operates generally as follows. Light emitted from light source 3010, as indicated by the dotted line, passes through diffuser 3012 and first polarizer 3014. Then the light signal reaches beam splitter 3016, which redirects a portion of the light signal towards the material samples, as indicated by the change in the illustrative light path. Light reflected from the material samples passes back through beam splitter 3016. If any portion of the light signal has been altered by any of the material samples, then it may pass through second polarizer 3018 that is rotated 90° from the first polarizer. Light that passes through second polarizer 3018 is received by lens 3020 and then captured by detector 3022.

Detector 3022 may capture an image of the entire array of material samples or it may capture a portion. If it captures a portion of the array, assembly 3000 may be moved accordingly so that a complete picture or detection of the array can be obtained.

Use of assemblies 1500, 1600 and 2100 allow for a complete workflow in the formulation of crystals of drug candidates. In one embodiment, the workflow begins with the original drug candidate being dispensed into vials 1516 of reaction assembly 1500, either while vials 1516 are in a separate rack or in reactor base 1514 (e.g., with bottom plate 1510 and shock-absorbent layer 1512 attached to reactor base 1514). The drug candidate can be in a solid state or in solution or suspension, but any solvent present with the original form of the drug candidate is removed, for example, by evaporation, wicking, or other methods known to those of skill in the art. The desired recrystallization solvent or solvent mixtures selected as discussed above are then dispensed into each vial 1516 in the desired amounts (typically with sufficient solvent to form saturated solutions in the vials). Optionally, different acids, bases, or salts are added (as discussed above in the salt selection process). Also optionally, mixing objects are placed in the vials (for example, using device 1402 such as in FIG. 14).

Barrier sheet 1518 and septum 1520 are placed over vials 1516 in reactor base 1514 (with bottom plate 1510 already attached) and reactor cover 1522 is secured to reactor base 1514 with sufficient strength to form seals over vials 1516. Assembled reaction assembly 1500 is then placed in a heater, shown in FIG. 23 (or FIGS. 24 and 25) and optionally placed on a commercially available shaker (available through VWR and made by IKA, MTS, WORKS or Labline). For a desired amount of time (such as 2 hours or more, 4 hours or more or 8 hours or more) and at a desired temperature (such as at least 40° C., at least 60° C. or at least 80° C.), assembly 1500 is heated and optionally stirred or shaken to allow for dissolution and/or reaction.

Afterwards, reaction assembly 1500 is placed on a work surface and a needle or pipette is used to sample the hot liquids in vials 1516. This is accomplished by inserting a needle or cannula through holes 1523, septum 1520 and barrier sheet 1518 and aspirating an aliquot of liquid (such as less than 1000 μL or less than 100 μL). The aliquot can be taken by hand or automatically, such as with the equipment shown in FIG. 23A as described above.

The aliquot of liquid is maintained in the needle or pipette that is moved to filtration assembly 1600, which is in an assembled state. The needle is placed into the first position as shown in FIGS. 20A and 20B, and extended through hole 1625A, septum 1620 and barrier sheet 1618 such that it is in sealing communication with small o-ring 1744. The liquid is dispensed through needle 2020 into opening 2020 and the liquid is filtered through the filter 1634 before entering vials 1616. Filtering can occur at a desired temperature by placing filtration assembly 1600 into a heater such as described above in FIG. 23.

After filtration, the filtrates (typically at a desired temperature) are aspirated by placing needle 2020 through hole 1625B, as shown in FIG. 20C. Needle 2020 extends through hole 1625B, septum 1620, barrier sheet 1618, filter subassembly 1630 and into vials 1616 to aspirate an aliquot of the liquid filtrate (e.g., less than 1000 μL or less than 100 μL of the filtrate). This filtrate is used for solubility at temperature testing, as described herein.

The needle is then moved to crystallization assembly 2100. The needle is extended through holes 2177 in reactor cover 2176 through septum 2174, barrier layer 2172 and into the crystallization receptacle formed by side walls 2169. Liquid filtrate is then dispensed into the receptacle. Liquid filtrate can be dispensed to a number of different crystallization assemblies, such as multiple crystallization assemblies, glass microtiter plates and the like so that crystallization occurs under a number of different conditions or methods. After dispensing into all receptacles, the crystallization assembly is subjected to crystallization conditions, such as by lowering the temperature of the assembly (e.g., below about 35° C. or below about 25° C. or below about 15° C. or below about 5° C.) for a desired amount of time (e.g., two hours or more, four hours or more or eight hours or more).

After the allotted time, reactor cover 2176, septum 2174, and barrier sheet 2172 are removed. In an alternative embodiment, the crystallization assembly can be used without reactor cover 2176, septum 2174 and barrier sheet 2172, with the filtrate being deposited directly into the crystallization chambers; with this embodiment allowing for other crystallization methodologies, such as evaporation. With reactor cover 2176 removed, the mother liquor or supernatant is sampled for solubility testing, as described herein. Thereafter, the remainder of the mother liquor or supernatant is removed by pipetting and/or wicking or other methods and crystallization assembly 2100 is disassembled providing an array of crystals on substrate 2164. This array can then be screened, as described herein. See Example 6 for an illustration of using the assemblies described herein in a crystallization workflow.

Although the above-described invention has been described for drug candidate compounds, this invention may be practiced with any compound of interest, particularly low molecular weight compounds. Thus, the methods, apparatus and systems described herein may be used for any compound for which salt selection and/or polymorph characterization is desired.

The following examples provide illustrative examples on how the present invention can be used to perform the processes described above. These examples are for the purpose of illustration only and are not to be construed as limiting the scope of the invention in any way.

EXAMPLE 1

Caffeine—Salt Selection

A solution of caffeine in dichloromethane (25 mg/mL) was dispensed into ninety-six wells of an eight by twelve microtiter plate reactor having removable vials (shown in FIG. 15) that may be 750 µl in size such that each well contained about 10 mg of caffeine. After removal of the solvent by evaporation, seven different solutions of acids in either dichloromethane or tetrahydrofuran (THF) (the salt reactants) were dispensed, with a different acid solution being dispensed into each of the twelve wells in different rows of the microtiter plate and with the first row having no acid added (only the solvent dichloromethane).

The following acid solutions were added to the twelve wells of each rows two through eight: row two, acetic acid in dicholomethane; row three, benzene sulfonic acid in dicholomethane; row four, hydrochloric acid in dichloromethane; row five, methyl sulfonic acid in dicholomethane; row six, succinic acid in THF; row seven, tartaric acid in THF; and row eight, toluene sulfonic acid in dichloromethane. One equivalent of acid was added to each well and the total volume was 400 µl. The reactor was sealed and shaken at room temperature for four hours. The cover was removed and the solvents evaporated. Twelve different recrystallization solvents were added to the wells, with a different recrystallization solvent being added to the eight wells of each twelve different columns, as follows: column one, ethylacetate; column two, ethanol; column three, methylethylketone; column four, nitromethane; column five, heptane; column six, aectonitrile; column seven, 2-propanol; column eight, p-dioxane; column 9, 2-methoxyethyl ether; column ten, 1-propanol; column eleven, toluene; and column twelve, water.

The reactor was sealed and heated to 60° C. and heated at that temperature for four hours. The cover was removed and aliquots (e.g., 200 µl) of each well were removed by pipette and dispensed to a glass microtiter plate (from Zinsser Analytics). Another aliquot was removed and added to an array of vials and diluted with acetonitrile for further dilution and liquid chromatography analyses, as described above in order to obtain a solubility measurement of the compound at 60° C. The glass microtiter plate was sealed and placed in a Torrey Pines incubator at 70° C. The temperature was ramped over 8 hours to 10° C. After sitting at 10° C. for at least ten hours, aliquots of the mother liquor were removed and diluted with acetonitrile for LC analysis, as described above. The concentration of the caffeine in the mother liquor is considered to be the solubility, with the results shown in Table 4, below:

TABLE 4

| | | | | | | | | | | | |
|---|---|---|---|---|---|---|---|---|---|---|---|
| 0.00 | 4.88 | 14.54 | 25.96 | 0.00 | 17.36 | 3.98 | 18.57 | 10.88 | 4.45 | 4.74 | 26.72 |
| 0.00 | 4.77 | 12.77 | 25.67 | 0.00 | 16.58 | 4.03 | 18.43 | 10.26 | 4.55 | 5.85 | 26.14 |
| 8.13 | 4.82 | 14.54 | 25.21 | 0.00 | 18.82 | 3.97 | 19.94 | 11.12 | 4.28 | 5.21 | 25.38 |
| 7.65 | 5.25 | 14.88 | 18.74 | 0.00 | 12.96 | 3.90 | 13.70 | 11.13 | 4.19 | 4.96 | 25.04 |
| 4.17 | 5.19 | 9.26 | 24.28 | 0.00 | 16.33 | 3.58 | 3.34 | 2.88 | 4.22 | 2.65 | 25.21 |
| 5.29 | 4.96 | 14.37 | 25.58 | 0.00 | 16.72 | 4.07 | 21.53 | 11.31 | 4.45 | 4.54 | 24.49 |
| 2.96 | 5.58 | 11.35 | 18.35 | 0.00 | 5.63 | 5.05 | 25.40 | 12.45 | 5.19 | 4.53 | 25.16 |
| 0.17 | 5.38 | 7.50 | 25.90 | 0.00 | 3.52 | 3.78 | 3.71 | 0.94 | 4.48 | 0.47 | 25.66 |

Note that the solubility measurements at 60° C. and 10° C. can be compared to obtain the mass of the crystals obtained, which was obtained in this case.

The glass plate was then placed between cross polarizing filters and scanned for wet birefringence. The remaining mother liquor was removed by pipette and residual solvent was removed by wicking with filter paper. Another image was taken between cross polarizing filter, giving dry birefringence. Birefringence images of the solids in wells were obtained under a microscope equipped with crossed polarized filters. Raman spectra were obtained on individual crystals in each of the wells, in accord with the procedures described above.

EXAMPLE 2

Naproxen—Salt Selection

A set of experiments, similar to Example 1, was carried out using naproxen to form salts by reaction with bases. The experimental set up was the same as in Example 1, using a solution of naproxen in dichloromethane (25 mg/mL) dispensed into 96 wells such that each well contained 10 mg of naproxen. After removal of the solvent by evaporation, seven different solutions of bases in either methanol or water (the salt reactants) were dispensed, with a different basic solution being dispensed the twelve wells of different rows of the microtiter plate and with the first row having no base added (only the solvent methanol).

The following basic solutions were added to the twelve wells of each row: row two, sodium hydroxide in methanol; row three, potassium hydroxide in methanol; row four, calcium carbonate in water; row five, ammonium hydroxide in methanol; row six, ethylenediamine in methanol; row seven, L-arginine in methanol; and row eight, pyridine in methanol. One equivalent of base was added to each well and the total volume was 400 µl.

The reactor was sealed and shaken at room temperature for four hours. The cover was removed and the solvents evaporated. Twelve different recrystallization solvents were added to the wells, with a different recrystallization solvent being added to the each of the eight wells of each different column, as follows: column one, isopropyl acetate; column two, ethanol; column three, heptane; column four, acetonitrile; column five, 1-octanol; column six, anhydrous p-dioxane; column seven, toluene; column eight, 2-butanone; column nine, water; column ten, nitromethane; column eleven, 1,2-dichloroethane; and column twelve, triethylamine. The reactor was sealed and heated to 60° C. for four hours. The cover was removed and aliquots (e.g., 200 µl) were removed by pipette and dispensed to a glass microtiter plate (from Zinsser Analytics).

Another aliquot was removed and added to an array of vials and diluted with acetonitrile for further dilution and liquid chromatography analyses, as described above in order to obtain a solubility measurement of the compound at 60° C. The glass microtiter plate was sealed and placed in a Torrey Pines incubator at 70° C. The temperature was ramped over eight hours to 10° C. After sitting at 10° C. overnight, aliquots of the mother liquor were removed and diluted with acetonitrile for solubility at 10° C. by liquid chromatography analysis, as described above. The solubility of each of the salts in 1-octanol and water at both 10° C. and 60° C. were obtained using LC and plotted and used to calculate the partition coefficient, which is expressed as log P and shown below in Table 5 (pH values were not obtained):

TABLE 5

| log P Values | Temperature 10° C. | Temperature 60° C. |
|---|---|---|
| Cation | | |
| None | 1.51 | 1.64 |
| Sodium | −0.94 | −0.77 |
| Potassium | −0.28 | −0.22 |
| Calcium | 0.68 | 0.78 |
| Ammonium | −0.57 | −0.50 |
| Ethylenediamine | −1.05 | −0.84 |
| L-Arginine | −0.74 | −0.85 |
| Pyridine | 0.82 | 1.45 |

The values of this experiment in Table 5 can be compared to the Log P value published in the Physicians Desk Reference for Naproxen of 1.6–1.8 at pH of 7.4. This experiment demonstrates that clearly different salt forms of Naproxen were created during this example.

The glass plate was placed between crossed polarizing filters and scanned for wet birefringence. The remaining mother liquor was removed by pipette and residual solvent was removed by wicking with filter paper. Another image was taken between crossed polarizing filters for dry birefringence.

EXAMPLE 3

Phenylbutazone—Polymorph Study

A solution of phenylbutazone in dichloromethane (25 mg/mL) was dispensed into wells of a microtiter plate having removable vials (shown in FIG. 3) that were 750 µl in size such that each well contained 10 mg of phenylbutazone. After removal of the solvent by evaporation, 16 recrystallization solvents were dispensed into the wells in the ratios shown below in Table 6, such that the total volume was 600 µl of solvent generating a library that included 84 unique solvent compositions. For mixtures of solvents, pure solvents were dispensed prior to mixing and mixed in the wells. The ratios shown in Table 6 are v/v ratios, thus for example 80/20 means 80 parts of the first listed solvent and 20 parts of the second listed solvent (i.e., 480 µl/120 µl). The recrystallization solvents were water (W), heptane (H), ethanol (E), dichloroethane (D), acetonitrile (A), methylethylketone (K), toluene (T), dimethylsulfoxide (S), 1-propanol (IP), nitromethane (NM), α, α, α-trifluorotoluene (FT), 2-propanol (2P), p-dioxane (I), 1-octanol (1O), propylacetate (PA), and cyclohexane (CH):

TABLE 6

| 1 | 2 | 3 | 4 | 5 | 6 | 7 | 8 | 9 | 10 | 11 | 12 |
|---|---|---|---|---|---|---|---|---|---|---|---|
| 100 | 80/20 | 60/40 | 40/60 | 20/80 | 100 | 100 | 80/20 | 60/40 | 40/60 | 20/80 | 100 |
| E | E/W | E/W | E/W | E/W | W | H | D/T | D/T | D/T | D/T | T |
| A | A/W | A/W | A/W | A/W | W | H | H/FT | H/FT | H/FT | H/FT | FT |
| 1P | 1P/W | 1P/W | 1P/W | 1P/W | W | H | H/D | H/D | H/D | H/D | D |
| I | I/W | I/W | I/W | I/W | W | H | H/PA | H/PA | H/PA | H/PA | PA |
| K | K/E | K/E | K/E | K/E | E | D | D/A | D/A | D/A | D/A | A |
| NM | NM/E | NM/E | NM/E | NM/E | E | D | D/S | D/S | D/S | D/S | S |
| H | H/E | H/E | H/E | H/E | E | D | D/2P | D/2P | D/2P | D/2P | 2P |
| 1O | 1O/E | 1O/E | 1O/E | 1O/E | E | D | D/CH | D/CH | D/CH | D/CH | CH |

The reactor was sealed and heated to 60° C. for four hours. The cover was removed and aliquots (e.g., 200 µl) were removed by pipette and dispensed into individual regions of a glass microtiter plate (from Zinsser Analytics), creating an array of ninety-six liquids. The Zinsser plate was sealed in the crystallizer and placed in a Torrey Pines incubator at 70° C. The temperature was decreased to 10° C. over an eight hour time period. After sitting at 10° C. overnight, aliquots of the mother liquor were removed and diluted with acetonitrile to determine the solubility of phenylbutazone in the various solvents at 10° C. by LC analysis.

The remainders of the solvents were removed by pipette and any residual solvent was removed by wicking with filter. The glass plate was then placed between cross polarizing filters and scanned for dry birefringence were obtained under a microscope at 5× equipped with crossed polarized filters. Raman spectra were obtained on individual crystals in each of the wells in an automated manner, as described above. Selected spectra that show the differences between polymorphs are shown in FIG. 9. All of the Raman spectra collected were correlated and grouped using the software described herein. FIG. 11 shows the spectra by well in array format 2008 as well as the user inputs into the software of minimum grouping correlation coefficient (with suggested parameters in parentheses) 2002 and whether to use a fixed reference (input of 1) or to use the first well as the reference (input of 0) 2004. FIG. 11 also shows the ability of the user to change the width and height of the spectra images 2006. FIG. 12 shows the output of the software with the spectra grouped by similarity into twelve families.

The entire recrystallization process was repeated with a different glass plate in the crystallizer, this time dispensing the hot solutions for recrystallization directly into the crystallizer subassembly (shown in FIG. 21, as described herein) in the same well format. The crystallizer subassembly was sealed and placed in a Torrey Pines incubator at 70° C. The temperature was decreased to 10° C. over an eight hour time period. After sitting at 10° C. overnight, aliquots of the mother liquor were removed and diluted with acetonitrile to determine the solubility of phenylbutazone in the various solvents at 10° C. by LC analysis. The remainders of the solvents were removed by pipette and any residual solvent was removed by wicking with filter paper. Disassembly of the crystallizer gave crystals in array format, with each crystal in a separate region on a flat glass substrate. The glass substrate was then mounted vertically on an X-ray diffraction machine, as described above and data was acquired on selected elements. Comparison of the XRD two theta plots clearly shows the presence of three polymorphs, shown in FIG. 10.

EXAMPLE 4

Cimetidine—Polymorph Study

A solution of cimetidine in dichloromethane (25 mg/mL) was dispensed into wells of a microtiter plate having removable vials that were 750 µl in size such that each well contained 10 mg of phenylbutazone. After removal of the solvent by evaporation, sixteen recrystallization solvents were dispensed as described above in Example 3 and in Table 6, above. The reactor was sealed and heated to 60° C. for four hours. The cover was removed and aliquots (e.g., 200 µl) of individual samples were removed by pipette and dispensed to the crystallization assembly (shown in FIG. 21, as described herein) in the same well format. Another aliquot was removed and added to an array of vials and diluted with acetonitrile for further dilution to determine the solubility of cimetidine in the various solvents at 70° C. by LC analysis. The crystallizer assembly was sealed and placed in a Torrey Pines incubator at 70° C. The temperature was ramped over 8 hours to 10° C. After sitting at 10° C. overnight, aliquots of the mother liquor were removed and diluted with acetonitrile for LC analysis. The solvents were removed by pipette and residual solvent was removed by wicking with filter. Removing the cover and disassembly of the crystallizer gave crystals on a flat glass substrate.

The glass plate was then placed between cross polarizing filters and scanned to obtain dry birefringence and birefringence images of selected wells were obtained under a microscope equipped with crossed polarized filter. Raman spectra were obtained on individual crystals in each of the wells as described in the previous example.

EXAMPLE 5

Sample Code for Polymorph Characterization

Various programming languages can be implemented to build software that can perform categorization of crystalline structures in accordance with the principles of the present invention. Listing 1, below, illustrates a portion of Java® code that can be used to implement the categorization process described in conjunction with FIG. 8.

Listing 1

```
package com.symyx.webapp.projects.polymorphs;
import com.symyx.webapp.xydata.filereader.*;
import com.symyx.webapp.xydata.*;
import java.util.*;
import java.io.*;
public class SignalProcessorPolymorphs {
private SignalProcessorResultPolymorphs result_;
    public SignalProcessorResultPolymorphs result( ) {
    return result_; }
    public void result(SignalProcessorResultPolymorphs
    theResult) { result_=
    theResult; }
    private SignalProcessorParametersPolymorphs
    parameters_;
    public SignalProcessorParametersPolymorphs
    parameters( ) { return parameters_; }
    public void
    parameters(SignalProcessorParametersPolymorphs params)
    {
    parameters_= params; }
public Signal ProcessorPolymorphs( ) {
    this. initialize( );
}
    private void initialize( ) {
        this.result(new
        SignalProcessorResultpolymorphs( ));
        this.parameters(new
        SignalProcessorParametersPolymorphs( ));
    }
public void sort(Vector items, Vector baskets) {
    if (items == null) {
        return;
    }
    int itemCount = 0;
    float cc;
    int i = 0;
    int j = 0;
    XyDataSet theSet = null;
    XyDataSet[] xySets = new XyDataSet[2];
    Vector stdItems = null;
    Vector stdBaskets = null;
    Vector ccScores = new Vector( );
    Float score = null;
    Float topScore = null;
    int scoreIndex = 0;
    int topScoreIndex = 0;
    Vector. theForm = null;
    int formCount = 0;
    float minCC = this.parameters( ).minGroupCC( );
    boolean useFixedReference =
    this.parameters( ).useFixedReference( );
    // standardize items to be sorted
    itemCount = items.size( );
    stditems = this.standardize(items);
    //System.out.println("made stditems");
    // standardize the known forms
    if (baskets != null) { // input not empty
        stdBaskets = this.standardize(baskets);
    }
    else {
    // no known forms yet,
    // so create new vector and put the first item in
    // there
    stdBaskets = new Vector( );
    stdBaskets.add(stditems.elementAt(0) );
}
//System.out.println("made stdBaskets");
// make form baskets
for (j=0; j<stdBaskets.size( ); j++) {
    theForm = this.result( ).addNewForm( );
    theForm.add(stdBaskets.elementAt(j) );
}
for (i=0; i<itemCount; i++) {
// clean out the old data
ccScores.clear( );
// get the next item to be classified
theSet = (XyDataset)stdItems.elementAt(i);
```

Listing 1

```
xySets[0] = theSet;
//System.out.println("sorting item: " + i + " " + theSet);
//System.out.println("xySets[0]: " + xySets[0] );
// get the forms
formCount = this.result( ).formCount( );
//System.out.println("formCount=" + formCount);
for (j=0; j<formCount; j++) {
    xySets[1] = (XyDataset)this.result( ).getFormData(j,
    useFixedReference);
    //System.out.println("xySets[1]: " + xySets[1] );
    // align the data sets
    XyDataMath.alignX (xySets);
    //System.out.println("xySets[0]: " + xySets[0] );
    //System.out.println("xySets[1]: " + xySets[1] );
    // run correlation
    cc = XyDataMath.corrcoef(xySets[0], xySets[1] );
    xySets[1].fitness(cc);
    //System.out.println("cc=" + cc);
    // add to the vector
    ccScores.add(j, new Float(cc) );
}
// find out which is the best
topScoreIndex = 0;
topScore = (Float)ccScores.elementAt(topScoreIndex);
for (j=0; j<formCount; j++)
    score = (Float)ccScores.elementAt(j);
        if (topScore.floatValue( ) < score.floatValue( ) ){
            topScore = score;
            topScoreIndex = j;
        }
        //System.out.println("topScoreIndex=" +
        topScoreIndex);
}
//System. out. println("top score: "
//+ topScore.floatValue( ) );
// qualified for one of the classified forms
if (Math.abs(topScore.floatValue( )–1.0f) <
java.lang.Float.MIN_VALUE) {
continue; // the same data set
}
else if (topScore.floatValue( ) >= minCC) {
    theForm = this.result( ).getForm(topScoreIndex);
    theForm.add(theSet);
    //System.out.println("old Form");
}
else { // found a new form
    theForm = this.result( ).addNewForm( );
    theForm.add(theSet);
    //System.out.println("newForm added");
}
}
}
}
/**
* standardize the data sets by removing the slope from the
    data sets,
* and perform normalization on them
*/
private Vector standardize(Vector theSets) {
    if (theSets == null) {
        return null;
    }
    Vector stdSets = new Vector( );
    XyDataSet theSet = null;
    String fileName = null;
    int count = theSets.size( );
    for (int i =0; i<count; i++) {
        //System.out.println("i:" + i);
        theSet = (XyDataSet)theSets.elementAt(i);
        //System.out.println("theSet:" +
        //theSet.header( ).getPath( ) );
        fileName = theSet.header( ).getDataName( );
        theSet = XyDataMath.removeSlope(theSet);
        theSet = XyDataMath.normalize(theSet);
        theSet.header( ).setDataName(fileName);
        stdSets.add(theSet);
    }
    return stdSets;
}
public Vector loadData( ) {
    String baseDir = "D:/raman_data/sorted_forms/";
    String listFileName = "Z_all_forms.txt";
    String fileName = null;
    String filePath = null;
    Vector fv = new Vector( );
    TextFileReader dataReader = new
    TextFileReaderPolymorphsRaman( );
    filePath = baseDir + listFileName;
    FileReader fileReader = null;
    LineNumberReader reader = null;
    try {
        fileReader = new FileReader(filePath);
        reader = new LineNumberReader(fileReader);
    }
    catch (IOException e) {
        e.printStackTrace( );
    }
    XyDataSet xyData = null;
    int i=0;
    try {
    while ( (fileName = reader.readLine( ) ) != null) {
        try {
            if (fileName.indexOf ("%") >= 0) {
                continue;
            }
            i++;
            filePath = baseDir + fileName;
            System.out.println("loading... "
            +.filePath);
            xyData = new XyDataSet( );
            dataReader.readFile(filePath, xyData);
            fv.add(xyData);
            //System.out.println(xyData.header( ).getDa
            //taName( ) );
        }catch (Exception e) {
            e.printStackTrace( );
        }
    }
}
catch (Exception e1) {
    e1.printStackTrace( );
}
finally {
    if (reader != null) {
        try {
            reader.close( );
            }catch (IOException e) {
            }
        }
    }
return fv;
}
public static void main (String[] args) {
    SignalProcessorPolymorphs spp =
    new SignalProcessorPolymorphs( );
    if (args.length > 0) {
        spp.parameters( ).minGroupCC(java.lang.Float.pars
        eFloat(args[0] ) );
        spp.parameters( ).useFixedReference(true);
    }
    Vector unknowns = spp.loadData( );
    System.out.println("..........");
    System.out.println("sorting...");
    spp.sort(unknowns, null);
    spp.result( ).printForms( );
}
}
```

EXAMPLE 6

Crystallization Workflow

Figure 31:
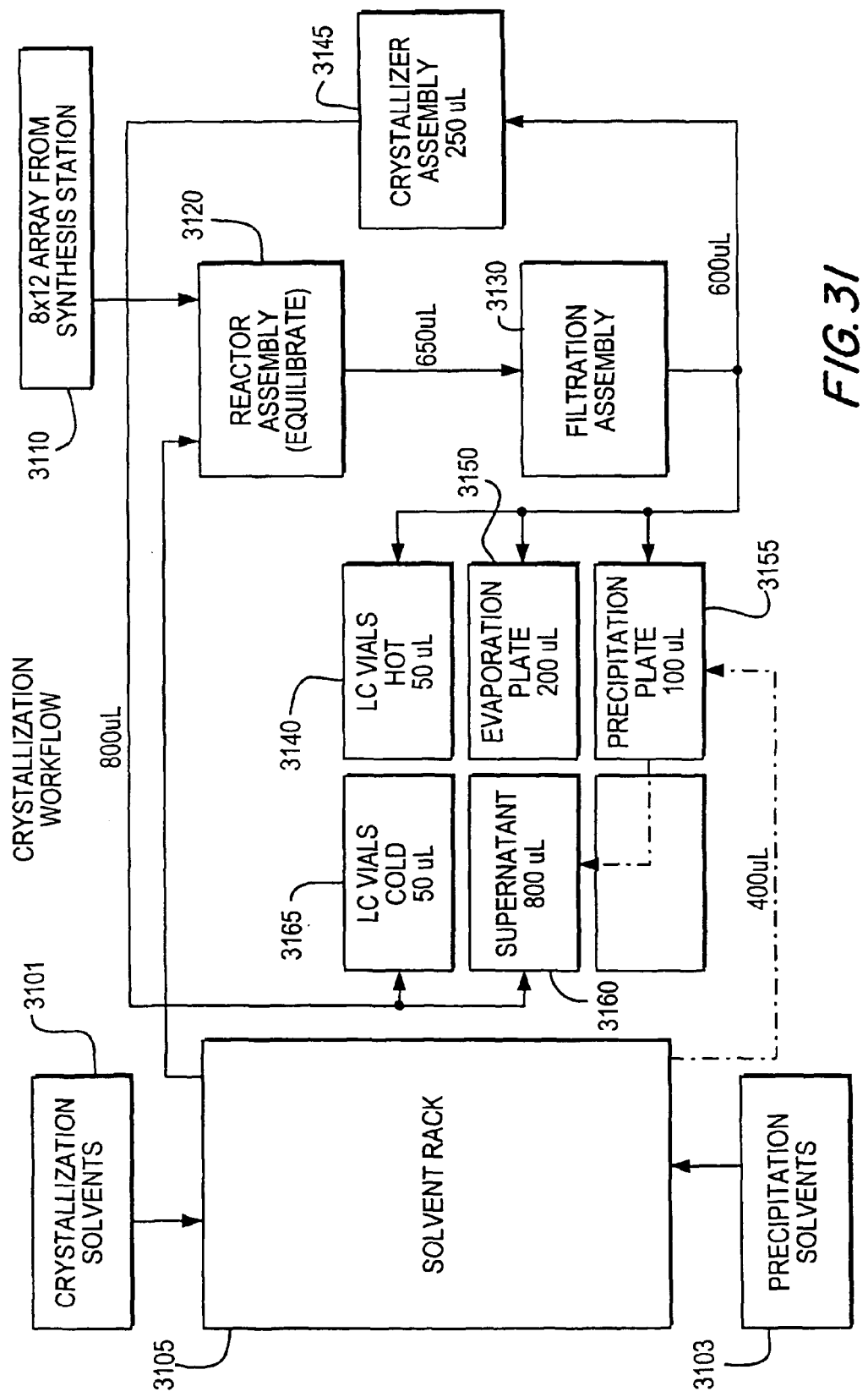
FIG. 31 shows an exemplary crystallization workflow using the methods and apparatus of the invention.

An exemplary crystallization workflow is shown in FIG. 31. In the workflow, the crystallization solvents 3101 and precipitation solvents 3103 of interest are placed in solvent rack 3105 for use in the workflow. Array 3110 comprising the drug candidate of interest (a salt or a neutral compound) from the reaction station is placed in reactor assembly 3120. The array can be an 8×12 array (e.g., a 96-well plate) or any other array known in the art (e.g., a 384-well plate). Crystallization solvents from the solvent rack are deposited into the wells of the array and the array is equilibrated to at least partially dissolve the drug candidate in the solvent. In one embodiment, 800 µL of the crystallization solvents are added to each well, although any volume of solvent may be used in accordance with this invention.

After the drug candidates have been equilibrated with the crystallization solvents to form solution, the solutions are filtered in filtration assembly 3130. In one non-limiting embodiment, 650 µL is taken from each well of the reactor assembly and filtered in the filtration assembly and a 600 µL aliquot of each sample is removed after filtration. The aliquots may then be daughtered for crystallization analysis and other analyses into one or more different apparatus. In one embodiment, 50 µL of each sample is aliquoted into liquid chromatography (LC) vials 3140 for determination of solubility at a high temperature; 250 µL from each sample is aliquoted into crystallizer assembly 3145 to investigate crystallization by cooling; 200 µL from each sample is aliquoted into evaporation plate 3150 to investigate crystallization by evaporation; and 100 µL of each sample is aliquoted into precipitation plate 3155 along with 400 µL of a precipitation solvent to investigate crystallization by precipitation.

After crystallization, supernatants from the samples subjected to crystallization in the crystallizer assembly and precipitation plate are collected. The supernatant from the crystallization assembly may be aliquoted into LC vials 3165 for determination of the solubility of the drug candidate at a cold temperature (e.g., room temperature or below). The supernatant may be collected at station 3160 for any purpose desired, such as recycling or discarding the drug candidate.

One having ordinary skill in the art following the teachings of this invention would recognize that one could use different combinations of crystallization apparatus and/or methods. For instance, one could provide a number of crystallizer assemblies that use different crystallization temperatures, or could use crystallizer assemblies to perform precipitation or evaporation crystallization. Further, one having ordinary skill in the art would recognize that one could perform different non-crystallization analyses using this workflow, such as log P analyses.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A filtration assembly for filtering an array of solutions, comprising:
   a reactor base having a plurality of receptacles:
   a filtration subassembly having a plurality of first and second channels that are respectively associated with one of said plurality of receptacles, wherein at least one of the plurality of first channels includes at least one filter element, the filtration subassembly including a plurality of sealing elements, the plurality of sealing elements including a plurality of first sealing elements associated with the first channels, the first sealing elements being configured to form a seal with a sample dispensing device while a sample is being introduced from the sample dispensing device into the at least one of the plurality of first channels for filtration, the filtration subassembly further including a plurality of second sealing elements associated with pairs of the first and second channels, the second sealing elements being configured to isolate the pairs of channels from other pairs of channels, the first sealing elements being disposed within a region defined by a corresponding ones of the second sealing elements, and wherein said plurality of second channels has no filter element and provides access to said associated receptacles; and
   a filter cover that secures said filtration subassembly to said reactor base, said filter cover having a plurality of pairs of holes that align to said plurality of first and second channels.

2. The filtration assembly according to claim 1, wherein said filtration subassembly comprises:
   a bottom layer that supports said at least one filter element, wherein said bottom layer has a pair of holes respectively associated with each one of said plurality of receptacles;
   a sealing layer that secures said at least one filter element to said bottom layer, said sealing layer having pairs of holes that align with said pairs of the holes in said bottom layer, said sealing layer further configured to house a plurality of o-rings; and
   a top layer that secures said plurality of o-rings to said sealing layer to form a substantially airtight seal that isolates each pair of said plurality of first an second channels from other said pairs of first and second channnels, said top lay having pairs of holes that align with said pairs of holes in said sealing layer such that aid plurality of first and second channels are provided.

3. The filtration assembly according to claim 2, wherein said plurality of first sealing elements includes a plurality of small o-rings that align with said plurality of first channels; and
   said plurality of second sealing elements includes a plurality of large o-rings connected to said small o-rings, each of said plurality of large o-rings surrounding one pair of said plurality of first and second crannels.

4. The filtration assembly according to claim 2, wherein said plurality of o-rings comprises:
   interconnected rows and columns of large o-ring, wherein each said large o-ring is coupled to a small o-ring.

5. The filtration assembly according to claim 4, wherein said small o-ring is coupled to an inner diameter of said large o-ring.

6. The filtration assembly according to claim 1, wherein said filtration subassembly comprises:
   at least two filtration plates coupled to said reactor base, said at least two filtration plates having a plurality of pairs of holes that form a portion of said plurality of first and second channels; and a filtration layer that includes said at least one filter element, said filtration layer is positioned between said at least two filtration plates.

7. The filtration assembly according to claim 1, herein said filtration layer comprises a sheet of gasket material that is coupled to said at least one filter element.

8. The filtration assembly according to claim 1 further comprising a filtration barrier sheet positioned between paid reactor base and said filtration subassembly, wherein said filtration barrier sheet has a plurality holes aligned with said plurality of receptacles.

9. The filtration assembly according to claim 1, further comprising a knife-edge ring associated with each of said first plurality of first channels, wherein each said knife-edge ring cuts each of said at least one filter element to a fixed size.

10. The filtration assembly according to claim 1, wherein said filtration assembly is further configured to fit into a heating assembly that subjects said filtration assembly to a thermal profile.

11. The filtration assembly of claim 1, wherein the first sealing elements isolate one or more of the at least one of the plurality of first channels from the corresponding second channel while the sample is being introduced into the first channel for filtration.

12. The filtration assembly of claim 11, wherein the plurality of pairs of holes in the filter cover includes a first hole aligning with the first channel, the first hole being configured to guide a sample dispensing device into operable engagement with the corresponding first sealing element while the sample is being introduced into the first channel for filtration.

13. The filtration assembly of claim 1, further comprising a heating assembly enclosing at least a portion of said filtration subassembly, said heating assembly being operable to heat said at least a portion of said filtration subassembly during a filtration process.

14. A filtration assembly for filtering an array of solutions, comprising:

a reactor base having a plurality of receptades;

a filtration subassembly having a plurality of pairs of channels, each of the plurality of pairs of channels being associated with one of the plurality of receptacles, each of the plurality of pairs of channels including a first channel having filter element, and a second channel having no filter element and providing access to the associated receptacle, the filtration subassembly including an o-ring layer, the o-ring layer including a plurality of small o-rings aligned with the first channels and a plurality of large o-rings aligned with the pairs of channels, the small o-rings being configured to form a seal with a sample dispensing device while a sample is being introduced from the sample dispensing device into the first channels for filtration, the large o-rings being configured to isolate the pairs of channels from other pairs of channels, each of the small o-rings being disposed within a region defined by a corresponding one of the large o-rings;

a filter cover that secures said filtration subassembly to said reactor base, said filter cover having a plurality of pairs of holes that align said plurality of first and second channels.

15. The filtration assembly of claim 1, further comprising:

a sample dispensing device for delivering samples to the first channels for filtration, the sample dispensing device being configured to engage with the first sealing element while a sample is being introduced into the first channel for filtration.

16. A method of filtering one or more liquid samples, the method comprising:

providing a filtration assembly comprising a reactor base having a plurality of receptacles, and a filtration subassembly having a plurality of first and second channels, pairs of the first and second channels being associated with respective ones of the plurality of receptacles, at least one of the plurality of first channels including at least one filter element, the plurality of second channels having no filter element and providing access to the associated receptacles, the filtration subassembly including a plurality of sealing elements, the plurality of sealing a elements include a first sealing element associated with the at least one of the plurality of first channels and a second sealing element associated with the at least one of the plurality of first channels and the corresponding one of the plurality of second channels, the first sealing element being disposed within a region defined by the second sealing element;

introducing a sample into the at least one of the plurality of first channels for filtration using a sample dispensing device, the sample dispensing device engaging with the first sealing element to form a seal in the at least one of the plurality of first channels during the introduction of the sample; and accessing the receptacle associated with the at least one of the plurality of first channels with a sample collecting device to collect a filtrate resulting from filtration of the sample.

* * * * *

UNITED STATES PATENT AND TRADEMARK OFFICE
CERTIFICATE OF CORRECTION

PATENT NO. : 6,939,515 B2 Page 1 of 1
DATED : September 6, 2005
INVENTOR(S) : Carlson et al.

It is certified that error appears in the above-identified patent and that said Letters Patent is hereby corrected as shown below:

<u>Title page,</u>
Item [75], Inventors, should read -- Eric D. Carlson, Cupertino, CA (US); William H. Chandler, Jr., Milpitas, CA (US); Peter J. Desrosiers, Santa Clara, CA (US) --.

Signed and Sealed this

Twenty-fifth Day of April, 2006

JON W. DUDAS
*Director of the United States Patent and Trademark Office*